US007005275B2

(12) United States Patent
Renner et al.

(10) Patent No.: US 7,005,275 B2
(45) Date of Patent: Feb. 28, 2006

(54) INDUCIBLE ALPHAVIRAL GENE EXPRESSION SYSTEM

(75) Inventors: Wolfgang A. Renner, Zurich (CH); Lars Nieba, Winterthur (CH); Marco Boorsma, Leeu Warden (NL)

(73) Assignee: Cytos Biotechnology AG, Zurich-Schlieren (CH)

( * ) Notice: Subject to any disclaimer, the term of this patent is extended or adjusted under 35 U.S.C. 154(b) by 32 days.

(21) Appl. No.: 09/275,883

(22) Filed: Mar. 25, 1999

(65) Prior Publication Data

US 2003/0053988 A1 Mar. 20, 2003

Related U.S. Application Data

(60) Provisional application No. 60/079,562, filed on Mar. 27, 1998.

(51) Int. Cl.
*C12P 21/06* (2006.01)
*C12N 15/00* (2006.01)
*C12N 5/00* (2006.01)

(52) U.S. Cl. .................... 435/69.1; 435/320.1; 435/325; 435/252.3; 424/218.1; 536/23.5; 536/23.51; 536/23.7; 536/24.1

(58) Field of Classification Search .............. 435/69.1, 435/320.1, 252.3, 325; 424/218.1; 536/23.7, 536/24.1, 23.5, 23.51; 514/44
See application file for complete search history.

(56) References Cited

U.S. PATENT DOCUMENTS

| 5,091,309 | A | 2/1992 | Schlesinger et al. ........ 435/69.1 |
| 5,217,879 | A | 6/1993 | Huang et al. .............. 435/69.1 |
| 5,532,154 | A | 7/1996 | Brown .................... 435/235.1 |
| 5,578,473 | A | 11/1996 | Palese et al. ............. 435/172.3 |
| 5,580,859 | A | 12/1996 | Felgner et al. ................ 514/44 |
| 5,705,163 | A | 1/1998 | Pastan et al. ............. 424/260.1 |
| 5,756,349 | A | 5/1998 | Lin ............................ 435/325 |
| 5,766,602 | A | 6/1998 | Xiong et al. ............. 424/218.1 |
| 5,789,245 | A | 8/1998 | Dubensky, Jr. et al. .. 435/320.1 |
| 5,792,462 | A | 8/1998 | Johnston et al. ......... 424/199.1 |
| 5,814,482 | A | 9/1998 | Dubensky, Jr. et al. .... 435/69.3 |
| 5,843,723 | A | 12/1998 | Dubensky, Jr. et al. .... 435/69.3 |

FOREIGN PATENT DOCUMENTS

| EP | 0 716 148 A2 | 6/1996 |
| WO | WO 94/17813 | 8/1994 |
| WO | WO 96/17072 | 6/1996 |
| WO | WO 97/38087 | 10/1997 |
| WO | WO 98/36779 | 8/1998 |
| WO | WO 99/18226 | 4/1999 |

OTHER PUBLICATIONS

Shirako et al (J. Virol. 72(3):2310–2315, Mar. 1998).*
Suopanki et al. (J. Gen. Virol. (79:309–319, 1998).*
Frolov et al al (J. Virol. 73(5):3854–3865, 1999).*
Shirako et al (Virology 177:54–64, 1990).*
Schnizer et. al., Mutations at Histidine 211 of the Yeast F1–ATPase B–Submit Affect the Stability and Assembly of the ATPase and the Structure of the Active Site, 1996; Archives of Biochemistry . . . , vol. 326: 126–136.*
Rudinger (In Peptide Hormones, J.A. Parsons Ed. University Park press, 1996:1–7).*
Hardy et al (Virology 177: 199–208, 1990).*
Perri et al (J. Virol. 74(20): 9802–9807, 2000).*
Agapov et al, Proc. Nat. Acad. Sci. USA 95: 12989–12994, se entire document, especially p. 12994, col. 1, first full paragraph, Oct. 1998.
Verma et al. Nature 389: 239–242, especially p. 239, Sep. 1997.
Anderson et al. Nature 392: 25–30, especially pp. 25 and 30, Apr. 1997.
Altman–Hamamdzic, S. et al.,"Expression of β–galactosidase in mouse brain: utilization of a novel nonreplicative Sindbis virus vector as a neuronal gene delivery system." *Gene Therapy* 4:815–822 (Aug. 1997).
Artelt, P. et al., "Vectors for efficient expression in mammalian fibroblastoid, myeloid and lymphoid cells via transfection or infection," *Gene* 68:213–219 (1988).
Artuc, M. et al., "Differential promoter activity in benign and malignant human cells of skin origin," *Exp. Dermatol.* 4:317–321 (1995).
Barton, D. J. et al., "Demonstration In Vitro of Temperature–Sensitive Elongation of RNA in Sindbis Virus Mutant ts6," *J. Virol.* 62:3597–3602 (1988).
Bechler, K., "Influence of Capping and Polyadenylation on mRNA Expression and on Antisense RNA Mediated Inhibition of Gene Expression," *Biochem. Biophys. Res. Comm.* 241:193–199 (Dec. 1997).
Berglund, P. et al., "Alphaviruses as vectors for gene delivery," *TIBTECH* 14:130–134 (Apr. 1996).

(Continued)

*Primary Examiner*—Dave Trong Nguyen
*Assistant Examiner*—Richard Schnizer
(74) *Attorney, Agent, or Firm*—Sterne, Kessler, Goldstein & Fox P.L.L.C.

(57) ABSTRACT

The present invention provides novel expression vectors which permit tight regulation of gene expression in eucaryotic cells. More specifically, the invention provides DNA vectors comprising nucleotide sequences that are transcribed to form RNA molecules which are then replicated by a temperature-sensitive replicase to form additional RNA molecules. The RNA molecules produced by replication contain a nucleotide sequence which may be translated to produce a protein of interest or which encode one or more untranslated RNA molecules. Also provided are methods for producing heterologous proteins and untranslated RNA molecules. Further provided are methods for administering heterologous proteins and untranslated RNA molecules to individuals. In addition, pharmaceutical compositions are provided comprising the DNA and RNA molecules of the invention and a pharmaceutically acceptable carrier.

46 Claims, 17 Drawing Sheets

OTHER PUBLICATIONS

Bohl, D. et al., "Long–term control of erythropoietin secretion by doxycycline in mice transplanted with engineered primary myoblasts," *Nature Med.* 3:299–305 (Mar. 1997).

Bredenbeek, P. J. and C. M. Rice, "Animal RNA virus expression systems," *Seminars in Virol.* 3:297–310 (1992).

Bredenbeek, P. J. et al., "Sindbis Virus Expression Vectors: Packaging of RNA Replicons by Using Defective Helper RNAs," *J. Virol.* 67:6439–6446 (1993).

Burge, B. W. and E. R. Pfefferkorn, "Isolation and Characterization of Conditional–Lethal Mutants of Sindbis Virus," *Virol.* 30:204–213 (1966).

Burge, B. W. and E. R. Pfefferkorn, "Complementation Between Temperature–sensitive Mutants of Sindbis Virus," *Virol.* 30:214–223 (1966).

Chapman, K. B. and J. W. Szostak, "Isolation of a ribozyme with 5'–5' Ligate activity," *Chem. & Biol.* 2:325–333 (1995).

Crameri, A. et al., "Improved Green Fluorescent Protein by Molecular Evolution Using DNA Shuffling," *Nature Biotech.* 14:315–319 (Mar. 1996).

Davis, N. L. et al., "In Vitro Synthesis of Infectious Venezuelan Equine Encephalitis Virus RNA from a cDNA Clone: Analysis of a Viable Deletion Mutant," *Virol.* 171:189–204 (1989).

De Groot, R. J. et al., "Sindbis virus RNA polymerase is degraded by the N–end rule pathway," *Proc. Natl. Acad. Sci. USA* 88:8967–8971 (1991).

Doedens, J. R. et al., "Inhibition of Endoplasmic Reticulum–to–Golgi Traffic by Poliovirus Protein 3A: Genetic and Ultrastructural Analysis," *J. Virol.* 71:9054–9064 (Dec. 1997).

Dryga, S. A. et al., "Identification of Mutations in a Sindbis Virus Variant Able to Establish Persistent Infection in BHK Cells: The Importance of a Mutation in the nsP2 Gene," *Virol.* 228:74–83 (Feb. 1997).

Dubensky, Jr., T. W. et al., "Sindbis Virus DNA–Based Expression Vectors: Utility for In Vitro and In Vivo Gene Transfer," *J. Virol.* 70:508–519 (Jan. 1996).

Dubuisson, J. et al., "Formation and Intracellular Localization of Hepatitis C Virus Envelope Glycoprotein Complexes Expressed by Recombinant Vaccinia and Sindbis Viruses," *J. Virol.* 68:6147–6160 (1994).

Frolov, I. et al., "Alphavirus–based expression vectors: Strategies and applications," *Proc. Natl. Acad. Sci. USA* 93:11371–11377 (Oct. 1996).

Früh, K. et al., "Displacement of housekeeping proteasome subunits by MHC–encoded LMPs: a newly discovered mechanism for modulating the multicatalytic proteinase complex," *EMBO J.* 13:3236–3244 (1994).

Furth, P. A. et al., "Temporal control of gene expression in transgenic mice by a tetracycline–responsive promoter," *Proc. Natl. Acad. Sci. USA* 91:9302–9306 (1994).

Gossen, M. and H. Bujard, "Tight control of gene expression in mammalian cells by tetracycline–responsive promoters," *Proc. Natl. Acad. Sci. USA* 89:5547–5551 (1992).

Hahn, C. S. et al., "Infectious Sindbis virus transient expression vectors for studying antigen processing and presentation," *Proc. Natl. Acad. Sci. USA* 89:2679–2683 (1992).

Hakimi, J. and P. H. Atkinson, "Glycosylation of Intracellular Sindbis Virus Glycoproteins," *Biochem.* 21:2140–2145 (1982).

Hariharan, M. J. et al., "DNA Immunization against Herpes Simplex Virus: Enhanced Efficacy Using a Sindbis Virus–Based Vector," *J. Virol.* 72:950–958 (Feb. 1998).

Hennighausen, L. et al., "Conditional Gene Expression in Secretory Tissues and Skin of Transgenic Mice Using the MMTV–LTR and the Tetracycline Responsive System," *J. Cell. Biochem.* 59:463–472 (1995).

Herweijer, H. et al., "A Plasmid–Based Self–Amplifying Sindbis Virus Vector," *Human Gene Ther.* 6:1161–1167 (1995).

Hoffmann, A. et al., "A novel tetracycline–dependent expression vector with low basal expression and potent regulatory properties in various mammalian cell lines," *Nucl. Acids Res.* 25:1078–1079 (Mar. 1997).

Howe, J. R. et al., "The Responsiveness of a Tetracycline–sensitive Expression System Differs in Different Cell Lines," *J. Biol. Chem.* 270:14168–14174 (1995).

Huang, H. V., "Sindbis virus vectors for expression in animal cells," *Curr. Opin. Biotech.* 7:531–535 (Oct. 1996).

Jeng, S.-Y. et al., "Characterization and Partial Purification of Bovine α–Lactalbumin and β–Casein Produced in Milk of Transgenic Mice," *J. Dairy Sci.* 80:3167–3175 (Dec. 1997).

Johanning, F. W. et al., "A sindbis virus mRNA polynucleotide vector achieves prolonged and high level heterologous gene expression in vivo," *Nucl. Acids Res.* 23:1495–1501 (1995).

Kawamata, H. et al., "Induction of TSC–22 by treatment with a new anti–cancer drug, vesnarinone, in a human salivary gland cancer cell," *Brit. J. Cancer* 77:71–78 (Jan. 1998).

Keränen, S. and L. Kääriäinen, "Functional Defects of RNA–Negative Temperature–Sensitive Mutants of Sindbis and Semliki Forest Viruses," *J. Virol.* 32:19–29 (1979).

Kerr, D. E. et al., "The bladder as a bioreactor: Urothelium production and secretion of growth hormone into urine," *Nature Biotech.* 16:75–79 (Jan. 1998).

Kistner, A. et al., "Doxycycline–mediated quantitative and tissue–specific control of gene expression in transgenic mice," *Proc. Natl. Acad. Sci. USA* 93:10933–10938 (Oct. 1996).

Lavrovsky, Y. et al., "Therapeutic Potential and Mechanism of Action of Oligonucleotides and Ribozymes," *Biochem. Mol. Med.* 62:11–22 (Oct. 1997).

Leake, C. J. et al., "Cytopathic Effect and Plaque Formation by Arboviruses in a Continuous Cell Line (XTC–2) from the Toad *Xenopus laevis*," *J. gen. Virol.* 35:335–339 (1977).

Lee, K. H. et al., "Two–Dimensional Electrophoresis of Proteins as a Tool in the Metabolic Engineering of Cell Cycle Regulation," *Biotech. Bioengin.* 50:336–340 (May 1996).

Lee, A. H. et al., "Comparison of Various Expression Plasmids for the Induction of Immune Response by DNA Immunization," *Mol. Cells* 7:495–501 (Aug. 1997).

Lemm, J. A. et al., "Mutations Which Alter the Level or Structure of nsP4 Can Affect the Efficiency of Sindbis Virus Replication in a Host–Dependent Manner," *J. Virol.* 64:3001–3011 (1990).

Lemm, J. A. and C. M. Rice, "Assembly of Functional Sindbis Virus RNA Replication Complexes: Requirement for Coexpression of P123 and P34," *J. Virol.* 67:1905–1915 (1993).

Liljeström, P. and H. Garoff, "A New Generation of Animal Cell Expression Vectors Based on the Semliki Forest Virus Replicon," *Bio/Technology* 9:1356–1361 (1991).

Liljeström, P., "Alphavirus expression systems," *Curr. Opin. Biotech.* 5:495–500 (1994).

Limonta, J. et al., "Production of active anti–CD6 mouse/human chimeric antibodies in the milk of transgenic mice," *Immunotech.* 1:107–113 (1995).

Lundstrom, K., "Alphaviruses as expression vectors," *Curr. Opin. Biotech.* 8:578–582 (Oct. 1997).

Mangelsdorf, D. J., "The Nuclear Receptor Superfamily: The Second Decade," *Cell* 83:835–839 (1995).

Máthé, E. et al., "The *Tomaj* mutant alleles of α*Tubulin67C* reveal a requirement for the encoded maternal specific tubulin isoform in the sperm aster, the cleavage spindle apparatus and neurogenesis during embryonic development in *Drosophila*," *J. Cell Sci.* 111:887–896 (Apr. 1998).

Meade, H. and C. Ziomek, "Urine as a substitute for milk?" *Nature Biotech* 16:21–22 (Jan. 1998).

Miki, T., "Heterogeneity of Sindbis Virus Glycoprotein $E_1$ and its Modification by Host Cell Transformation," *J. gen. Virol.* 65:343–354 (1984).

Minch, S. L. et al., "Tissue Plasminogen Activator Coexpressed in Chinese Hamster Ovary Cells with α(2,6)-Sialytransferase Contains NeuAcα(2,6)Galβ(1,4)Glc–N–AcR Linkages," *Biotechnol. Prog.* 11:348–351 (1995).

Olkkonen, V. H. et al., "Expression of Exogenous Proteins in Mammalian Cells with the Semliki Forest Virus Vector," *Meth. Cell Biol.* 43:43–53 (1994).

Palese, P. et al., "Negative–strand RNA viruses: Genetic engineering and applications," *Proc. Natl. Acad. Sci. USA* 93:11354–11358 (Oct. 1996).

Patterson, B. et al., "Cold–sensitive Mutants G680V and G691C of *Dictyostelium* Myosin II Confer Dramatically Different Biochemical Defects," *J. Biol. Chem.* 272:27612–27617 (Oct. 1997).

Paul, N. L. et al., "Expression of HIV–1 Envelope Glycoproteins by Semliki Forest Virus Vectors," *AIDS Res. and Hum. Retrovir.* 9:963–970 (1993).

Peng, L. et al., "Construction of Recombinant Adeno–Associated Virus Vector Containing the Rat Preproinsulin II Gene," *J. Surg. Res.* 69:193–198 (Apr. 1997).

Piper, R. C. et al., "Recombinant Sindbis Virus as an Expression System for Cell Biology," *Meth. Cell Biol.* 43:55–78 (1994).

Prodromou, C. and L. H. Pearl, "Recursive PCR: a novel technique for total gene synthesis," *Protein Engin.* 5:827–829 (1992).

Qing, K. et al., "Adeno–Associated Virus Type 2–Mediated Transfer of Ecotropic Retrovirus Receptor cDNA Allows Ecotropic Retroviral Transduction of Established and Primary Human Cells," *J. Virol.* 71:5663–5667 (Jul. 1997).

Renner, W. A. et al., "Recombinant Cyclin E Expression Activates Proliferation and Obviates Surface Attachment of Chinese Hamster Ovary (CHO) Cells in Protein–Free Medium," *Biotech. Bioeng.* 47:476–482 (1995).

Saez, E. et al., "Inducible gene expression in mammalian cells and transgenic mice," *Curr. Opin. Biotech.* 8:608–616 (Oct. 1997).

Schlesinger, M. J. and S. Schlesinger, "Formation and Assembly of Alphavirus Glycoproteins," in *The Togaviridae and Flaviviridae*, Plenum Press, New York, NY, pp. 121–148 (1986).

Schlesinger, S., "Alphaviruses—vectors for the expression of heterologous genes," *TIBTECH* 11:18–22 (1993).

Shockett, P. et al., "A modified tetracycline–regulated system provides autoregulatory, inducible gene expression in cultured cells and transgenic mice," *Proc. Natl. Acad. Sci. USA* 92:6522–6526 (1995).

Shockett, P. E. and D. G. Schatz, "Diverse strategies for tetracycline–regulated inducible gene expression," *Proc. Natl. Acad. Sci. USA* 93:5173–5176 (May 1996).

Schwer, B. et al., "Effects of deletion mutations in the yeast Ces1 protein on cell growth and morphology and on high copy suppression of mutations in mRNA capping enzyme and translation initiation factor 4A," *Nucl. Acids Res.* 26:803–809 (Feb. 1998).

Smith, S. M. et al., "Efficient Expression by an Alphavirus Replicon of a Functional Ribozyme Targeted to Human Immunodeficiency Virus Type 1," *J. Virol.* 71:9713–9721 (Dec. 1997).

Stanley, P., "Glycosylation engineering," *Glycobiology* 2:99–107 (1992).

Strauss, E. G. and J. H. Strauss, "Mutants of Alphaviruses: Genetics and Physiology," in *The Togaviruses*, Schlesinger, R. W., ed., Academic Press, New York, NY, pp. 393–426 (1980).

Strauss, J. H. and E. G. Strauss, "The Alphaviruses: Gene Expression, Replication and Evolution," *Microbiol. Rev.* 58:491–562 (1994).

Urakami, S. et al., "Overexpression of Members of the AP–1 Transcriptional Factor Family from an Early Stage of Renal Carcinogenesis and Inhibition of Cell Growth by AP–1 Gene Antisense Oligonucleotides in the *Tsc2* Gene Mutant (Eker) Rat Model," *Biochem. and Biophys. Res. Comm.* 241:24–30 (Dec. 1997).

Wang, Y. et al., "A regulatory system for use in gene transfer," *Proc. Natl. Acad. Sci. USA* 91:8180–8184 (1994).

Wang, Y. et al., "Ligand–inducible and liver–specific target gene expression in transgenic mice," *Nature Biotech.* 15:239–243 (Mar. 1997).

Watson, E. et al., "Structure determination of the intact major sialylated oligosaccharide chains of recombinant human erythropoietin expressed in Chinese hamster ovary cells," *Glycobiology* 4:227–237 (1994).

Weiss, B. et al., "Establishment and Maintenance of Persistent Infection by Sindbis Virus in BHK Cells," *J. Virol.* 33:463–474 (1980).

Wimmel, A. et al., "Inducible acceleration of $G_1$ progression through tetracycline–regulated expression of human cyclin E," *Oncogene* 9:995–997 (1994).

Wu, A. M. "In vivo veritas: Live phage display panning," *Nature Biotech.* 14:429–431 (Apr. 1996).

Xie, Y. et al., "A ribozyme–mediated, gene "knockdown" strategy for the identification of gene function in zebrafish," *Proc. Natl. Acad. Sci. USA* 94:13777–13781 (Dec. 1997).

Xiong, C. et al., "Sindbis Virus: An Efficient, Broad Host Range Vector for Gene Expression in Animal Cells," *Science* 243:1188–1191 (1988).

Yu, H. et al., "Inducible Human Immunodeficiency Virus Type 1 Packaging Cell Lines," *J. Virol.* 70:4530–4537 (Jul. 1996).

Zang, M. et al., "Production of Recombinant Proteins in Chinese Hamster Ovary Cells Using a Protein–Free Cell Culture Medium," *Biotech.* 13:389–392 (1995).

Invitrogen Manual, "Sindbis Expression System, Version C," from internet web page http://www.invitrogen.com/manuels.html, Catalog No. K750–01 (1996).

Dé, I. et al., "Sindbis Virus RNA–Negative Mutants That Fail to Convert from Minus–Strand to Plus–Strand Synthesis: Role of the nsP2 Protein," *J. Virol.* 70:2706–2719 (1996).

DiCiommo, D.P. and R. Bremner, "Rapid, High Level Protein Production Using DNA–based Semliki Forest Virus Vectors," *J. Biol. Chem.* 273:18060–18066 (Jul. 1998).

Shirako, Y. and J.H. Strauss, "Regulation of Sindbis Virus RNA Replication: Uncleaved P123 and nsP4 Function in Minus–Strand RNA Synthesis, whereas Cleaved Products from P123 Are Required for Efficient Plus–Strand RNA Synthesis," *J. Virol.* 68:1874–1885 (1994).

Suopanki, J. et al., "Regulation of alphavirus 26S mRNA transcription by replicase component nsP2," *J. Gen. Virol.* 79:309–319 (Feb. 1998).

Younker, D.R. and S.G. Sawicki, "Negative Strand RNA Synthesis by Temperature–Sensitive Mutants of Mouse Hepatitis Virus," in *Coronaviruses and Arteriviruses*, Enjuanes et al., eds., Plenum Press, New York, pp. 221–226 (1998).

Caley, I.J. et al., "Humoral, Nucosal, and Cellular Immunity in Response to a Human Immunodeficiency Virus Type 1 Immunogen Expressed by a Venezuelan Equine Encephalitis Virus Vaccine Vector," *J. Virology* 71:3031–3038, American Society for Microbiology (Apr. 1997).

Ciccarone, V. et al., "pSFV1 Eukaryotic Expression Vector: A Novel Protein Expression System," *Focus* 15:103–105, Life Technologies, Inc. (1993).

Arias, C., et al., "Sequence Analaysis of Two Mutants of Sindbis Virus Defective in the Intracellular Transport of Their Glycoproteins," *J. Mol. Biol.* 168:87–102 (Jul. 1983).

Carleton, M., and Brown, D.T., "Events in the Endoplasmic Reticulum Abrogate the Temperature Sensitivity of Sindbis Virus Mutant *ts*23," *J. Virol.* 70:952–959 (Feb. 1996).

Lindqvist, B.H., et al., "Sindbis Virus Mutant *ts*20 of Complementation Group E Contains a Lesion in Glycoprotein E2," *Virol.* 151:10–20 (May 1986).

Davis, N.L. et al., "A Viral Vaccine Vector That Expresses Foreign Genes in Lymph Nodes and Protects against Mucosal Challenge," *J. Virology* 70:3781–3787, American Society for Microbiology (1996).

DiCiommo, D.P. and R. Bremner, "Rapid, High Level Protein Production Using DNA–based Semliki Forest Virus Vectors," *J. Biol. Chem.* 273:18060–18066, The American Society for Biochemistry and Molecular Biology, Inc. (Jul. 1998).

Grakoui, A. et al., "A *cis*–Acting Mutation in the Sindbis Virus Junction Region Which Affects Subgenomic RNA Synthesis," *J. Virology* 63:5216–5227, American Society for Microbiology (1989).

Guan, H. et al., "RNA promoters located on (–)–strands of a subviral RNA associated with turnip crinkle virus," *RNA* 3:1401–1412, Cambridge University Press (Dec. 1997).

Khromykh, A.A. and E.G. Westaway, "Subgenomic Replicons of the Flavivirus Kunjin: Construction and Applications," *J. Virology* 71:1497–1505, American Society for Microbiology (Feb. 1997).

Khromykh, A.A. et al., "*trans*–Complementation of Flavivirus RNA Polymerase Gene NS5 by Using Kunjin Virus Replicon–Expressing BHK Cells," *J. Virology* 72:7270–7279, American Society for Microbiology (Sep. 1998).

Khromykh, A.A. et al., "Efficient *trans*–Complementation of the Flavivirus Kunjin NS5 Protein but Not of the NS1 Protein Requires Its Coexpression with Other Components of the Viral Replicase," *J. Virology* 73:10272–10280, American Society for Microbiology (Dec. 1999).

Kohno, A. et al., "Semliki Forest Virus–based DNA expression vector: transient protein production followed by cell death," *Gene Therapy* 5:415–418, Stockton Press (Mar. 1998).

Kuhn, R.J. et al., "Mutagenesis of the 3' Nontranslated Region of Sindbis Virus RNA," *J. Virology* 64:1465–1476, American Society for Microbiology (1990).

Kujala, P. et al., "Monoclonal antibodies specific for Semliki Forest virus replicase protein nsP2," *J. Gen. Virology* 78:343–351, Society for General Microbiology (Feb. 1997).

Laakkonen, P. et al., "Alphavirus Replicase Protein NSP1 Induces Filopodia and Rearrangement of Actin Filaments," *J. Virology* 72:10265–10269, American Society for Microbiology (Dec. 1998).

Lama, J. et al., "Genetic analysis of poliovirus protein 3A: characterization of a non–cytopathic mutant virus defective in killing Vero cells," *J. Gen. Virology* 79:1911–1921, Society for General Microbiology (Aug. 1998).

Landis, H. et al., "Human MxA Protein Confers Resistance to Semliki Forest Virus and Inhibits the Amplification of a Semliki Forest Virus–Basd Replicon in the Absence of Viral Structural Proteins," *J. Virology* 72:1516–1522, American Society for Microbiology (Feb. 1998).

Levis, R. et al., "Promoter for Sindbis Virus RNA–Dependent Subgenomic RNA Transcription," *J. Virology* 64:1726–1733, American Society for Microbiology (1990).

O'Reilly, E.K. et al., "Interactions between the Structural Domains of the RNA Replication Proteins of Plant–Infecting RNA Viruses," *J. Virology* 72:7160–7169, American Society for Microbiology (Sep. 1998).

Polo, J.M. et al., "Stable alphavirus packaging cell lines for Sindbis virus– and Semliki Forest virus–derived vectors," *Proc. Natl. Acad. Sci. USA* 96:4598–4603, The National Academy of Sciences of the USA (Apr. 1999).

Pugachev, K.V. and T.K. Frey, "Effects of Defined Mutations in the 5' Nontranslated Region of Rubella Virus Genomic RNA on Virus Viability and Macromolecule Synthesis," *J. Virology* 72:641–650, American Society for Microbiology (Jan. 1998).

Pushko, P. et al., "Replicon–Helper Systems from Attenuated Venezuelan Equine Encephalitis Virus: Expression of Heterologous Genes in Vitro and Immunization against Heterologous Pathogens in Vivo," *Virology* 239:389–401, Academic Press (Dec. 1997).

Rikkonen, M., "Functional Significance of the Nuclear–Targeting and NTP–Binding Motifs of Semliki Forest Virus Nonstructural Protein nsP2," *Virology* 218:352–361, Academic Press (1996).

Roks, A.J.M. et al., "Vectors based on Semliki Forest virus for rapid and efficient gene transfer into non–endothelial cardiovascular cells: comparison to adenovirus," *Cardiovascular Res.* 35:498–504, Elsevier Science B.V. (Sep. 1997).

Scallan, M.F. et al., "*bcl*–2 Acts Early To Restrict Semliki Forest Virus Replication and Delays. Virus–Induced Programmed Cell Death," *J. Virology* 71:1583–1590, American Society for Microbiology (Feb. 1997).

Schneider–Schaulies, S. et al., "Cell Type–Specific MxA–Mediated Inhibition of Measles Virus Transcription in Human Brain Cells," *J. Virology* 68:6910–6917, American Society for Microbiology (1994).

Schnorr, J.–J. et al., "MxA–Dependent Inhibition of Measles Virus Glycoprotein Synthesis in a Stably Transfected Human Monocytic Cell Line," *J. Virology 67*:4760–4768, American Society for Microbiology (1993).

Siegel, R.W. et al., "Sequence–specific recognition of a subgenomic RNA promoter by a viral RNA polymerase," *Proc. Natl. Acad. Sci. USA 94*:11238–11243, The National Academy of Sciences of the USA (Oct. 1997).

Turina, M. et al., "Nucleotide Sequence and Infectivity of a Full–Length cDNA Clone of Panicum Mosaic Virus," *Virology 241*:141–155, Academic Press (Feb. 1998).

Van Dinten, L.C. et al., "An infectious arterivirus cDNA clone: Identification of a replicase point mutation that abolishes discontinuous mRNA transcription," *Proc. Natl. Acad. Sci. USA 94*:991–996, The National Academy of Sciences of the USA (Feb. 1997).

Wang, J. and A.E. Simon, "Analysis of the Two Subgenomic RNA Promoters for Turnip Crinkle Virus in Vivo and in Vitro," *Virology 232*:174–186, Academic Press (May 1997).

Wengler, G., "Chapter 16. Effects of Alphaviruses on Host Cell Macromolecular Synthesis," in *The Togaviruses. Biology Structure. Replication*, R.W. Schlesinger, ed., Academic Press, New York, NY, pp. 459–472 (1980).

Zhang, J. et al., "Cloning of human IL–12 p40 and p35 DNA into the Semliki Forest virus vector: expression of IL–12 in human tumor cells," *Gene Therapy 4*:367–374, Stockton Press (Apr. 1997).

* cited by examiner

```
CTGACGCGCCCTGTAGCGGCGCATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCCCGTCAAGCTCTAAATCGGGG
GCTCCCTTTAGGGTTCCGATTTAGTGCTTTACGGCACCTCGACCCCAAAAAACTTGATTAGGGTGATGGTTCACGTAGTG
GGCCATCGCCCTGATAGACGGTTTTTCGCCCTTTGACGTTGGAGTCCACGTTCTTTAATAGTGGACTCTTGTTCCAAACT
GGAACAACACTCAACCCTATCTCGGTCTATTCTTTTGATTTATAAGGGATTTTGCCGATTTCGGCCTATTGGTTAAAAAA
TGAGCTGATTTAACAAAAATTTAACGCGAATTTTAACAAAATATTAACGCTTACAATTTCCATTCGCCATTCAGGCTGCG
CAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTGAgcgcgcaattaaccctcactaa
agggaacaaaagctggctagtgGATCCAGTCTTATGCAATACTCTTGTAGTCTTGCAACATGGTAACGATGAGTTAGCAA
CATGCCTTACAAGGAGAGAAAAAGCACCGTGCATGCCGATTGGTGGAAGTAAGGTGGTACGATCGTGCCTTATTAGGAAG
GCAACAGACGGGTCTGACATGGATTGGACGAACCACTGAATTCCGCATTGCAGAGATATTGTATTTAAGTGCCCTACCTc
gataccgTCGAGATTGACGGCGTAGTACACACTATTGAATCAAACAGCCGACCAATTGCACTACCATCACAATGGAGAAG
CCAGTAGTAAACGTAGACGTAGACCCCCAGAGTCCGTTTGTCGTGCAACTGCAAAAAAGCTTCCCGCAATTTGAGGTAGT
AGCACAGCAGGTCACTCCAAATGACCATGCTAATGCCAGAGCATTTTCGCATCTGGCCAGTAAACTAATCGAGCTGGAGG
TTCCTACCACAGCGACGATCTTGGACATAGGCAGCGCACCGGCTCGTAGAATGTTTTCCGAGCACCAGTATCATTGTGTC
TGCCCCATGCGTAGTCCAGAAGACCCGGACCGCATGATGAAATACGCCAGTAAACTGGCGGAAAAAGCGTGCAAGATTAC
AAACAAGAACTTGCATGAGAAGATTAAGGATCTCCGGACCGTACTTGATACGCCGGATGCTGAAACACCATCGCTCTGCT
TTCACAACGATGTTACCTGCAACATGCGTGCCGAATATTCCGTCATGCAGGACGTGTATATCAACGCTCCCGGAACTATC
TATCATCAGGCTATGAAAGGCGTGCGGACCCTGTACTGGATTGGCTTCGACACCACCCAGTTCATGTTCTCGGCTATGGC
AGGTTCGTACCCTGCGTACAACACCAACTGGGCCGACGAGAAAGTCCTTGAAGCGCGTAACATCGGACTTTGCAGCACAA
AGCTGAGTGAAGGTAGGACAGGAAAATTGTCGATAATGAGGAAGAAGGAGTTGAAGCCCGGGTCGCGGGTTTATTTCTCC
GTAGGATCGACACTTTATCCAGAACACAGAGCCAGCTTGCAGAGCTGGCATCTTCCATCGGTGTTCCACTTGAATGGAAA
GCAGTCGTACACTTGCCGCTGTGATACAGTGGTGAGTTGCGAAGGCTACGTAGTGAAGAAAATCACCATCAGTCCCGGGA
TCACGGGAGAAACCGTGGGATACGCGGTTACACACAATAGCGAGGGCTTCTTGCTATGCAAAGTTACTGACACAGTAAAA
GGAGAACGGGTATCGTTCCCTGTGTGCACGTACATCCCGGCCACCATATGCGATCAGATGACTGGTATAATGGCCACGGA
TATATCACCTGACGATGCACAAAAACTTCTGGTTGGGCTCAACCAGCGAATTGTCATTAACGGTAGGACTAACAGGAACA
CCAACACCATGCAAAATTACCTTCTGCCGATCATAGCACAAGGGTTCAGCAAATGGGCTAAGGAGCGCAAGGATGATCTT
GATAACGAGAAAATGCTGGGTACTAGAGAACGCAAGCTTACGTATGGCTGCTTGTGGGCGTTTCGCACTAAGAAAGTACA
TTCGTTTTATCGCCCACCTGGAACGCAGACCTGCGTAAAAGTCCCAGCCTCTTTTAGCGCTTTTCCCATGTCGTCCGTAT
GGACGACCTCTTTGCCCATGTCGCTGAGGCAGAAATTGAAACTGGCATTGCAACCAAAGAAGGAGGAAAAACTGCTGCAG
GTCTCGGAGGAATTAGTCATGGAGGCCAAGGCTGCTTTTGAGGATGCTCAGGAGGAAGCCAGAGCGGAGAAGCTCCGAGA
AGCACTTCCACCATTAGTGGCAGACAAAGGCATCGAGGCAGCCGCAGAAGTTGTCTGCGAAGTGGAGGGGCTCCAGGCGG
ACATCGGAGCAGCATTAGTTGAAACCCCGCGCGGTCACGTAAGGATAATACCTCAAGCAAATGACCGTATGATCGGACAG
TATATCGTTGTCTCGCCAAACTCTGTGCTGAAGAATGCCAAACTCGCACCAGCGCACCCGCTAGCAGATCAGGTTAAGAT
CATAACACACTCCGGAAGATCAGGAAGGTACGCGGTCGAACCATACGACGCTAAAGTACTGATGCCAGCAGGAGGTGCCG
TACCATGGCCAGAATTCCTAGCACTGAGTGAGAGCGCCACGTTAGTGTACAACGAAAGAGAGTTTGTGAACCGCAAACTA
TACCACATTGCCATGCATGGCCCCGCCAAGAATACAGAAGAGGAGCAGTACAAGGTTACAAAGGCAGAGCTTGCAGAAAC
AGAGTACGTGTTTGACGTGGACAAGAAGCGTTGCGTTAAGAAGGAAGAAGCCTCAGGTCTGGTCCTCTCGGGAGAACTGA
CCAACCCTCCCTATCATGAGCTAGCTCTGGAGGGACTGAAGACCCGACCTGCGGTCCCGTACAAGGTCGAAACAATAGGA
GTGATAGGCACACCGGGGTCGGGCAAGTCAGCTATTATCAAGTCAACTGTCACGGCACGAGATCTTGTTACCAGCGGAAA
GAAAGAAAATTGTCGCGAAATTGAGGCCGACGTGCTAAGACTGAGGGGTATGCAGATTACGTCGAAGACAGTAGATTCGG
TTATGCTCAACGGATGCCACAAAGCCGTAGAAGTGCTGTACGTTGACGAAGCGTTCGCGTGCCACGCAGGAGCACTACTT
GCCTTGATTGCTATCGTCAGGCCCCGCAAGAAGGTAGTACTATGCGGAGACCCCATGCAATGCGGATTCTTCAACATGAT
GCAACTAAAGGTACATTTCAATCACCCTGAAAAAGACATATGCACCAAGACATTCTACAAGTATATCTCCCGGCGTTGCA
```

FIG.3A

```
CACAGCCAGTTACAGCTATTGTATCGACACTGCATTACGATGGAAAGATGAAAACCACGAACCCGTGCAAGAAGAACATT
GAAATCGATATTACAGGGGGCCACAAAGCCGAAGCCAGGGGATATCATCCTGACATGTTTCCGCGGGTGGGTTAAGCAATT
GCAAATCGACTATCCCGGACATGAAGTAATGACAGCCGCGGCCTCACAAGGGCTAACCAGAAAAGGAGTGTATGCCGTCC
GGCAAAAAGTCAATGAAAACCCACTGTACGCGATCACATCAGAGCATGTGAACGTGTTGCTCACCCGCACTGAGGACAGG
CTAGTGTGGAAAACCTTGCAGGGCGACCCATGGATTAAGCAGCCCACTAACATACCTAAAGGAAACTTTCAGGCTACTAT
AGAGGACTGGGAAGCTGAACACAAGGGAATAATTGCTGCAATAAACAGCCCCACTCCCCGTGCCAATCCGTTCAGCTGCA
AGACCAACGTTTGCTGGGCGAAAGCATTGGAACCGATACTAGCCACGGCCGGTATCGTACTTACCGGTTGCCAGTGGAGC
GAACTGTTCCCACAGTTTGCGGATGACAAACCACATTCGGCCATTTACGCCTTAGACGTAATTTGCATTAAGTTTTTCGG
CATGGACTTGACAAGCGGACTGTTTTCTAAACAGAGCATCCCACTAACGTACCATCCCGCCGATTCAGCGAGGCCGGTAG
CTCATTGGGACAACAGCCCAGGAACCCGCAAGTATGGGTACGATCACGCCATTGCCGCCGAACTCTCCCGTAGATTTCCG
GTGTTCCAGCTAGCTGGGAAGGGCACACAACTTGATTTGCAGACGGGGAGAACCAGAGTTATCTCTGCACAGCATAACCT
GGTCCCGGTGAACCGCAATCTTCCTCACGCCTTAGTCCCCGAGTACAAGGAGAAGCAACCCGGCCCGGTCAAAAAATTCT
TGAACCAGTTCAAACACCACTCAGTACTTGTGGTATCAGAGGAAAAAATTGAAGCTCCCCGTAAGAGAATCGAATGGATC
GCCCCGATTGGCATAGCCGGTGCAGATAAGAACTACAACCTGGCTTTCGGGTTTCCGCCGCAGGCACGGTACGACCTGGT
GTTCATCAACATTGGAACTAAATACAGAAACCACCACTTTCAGCAGTGCGAAGACCATGCGGCGACCTTAAAAACCCTTT
CGCGTTCGGCCCTgaattgTTtAaacTcaggaggcacCCTCGTGGTGAAGTCCTATGGCTACGCCGACCGCAACAGTGAG
GACGTAGTCACCGCTCTTGCCAGAAAGTTTGTCAGGGTGTCTGCAGCGAGACCAGATTGTGTCTCAAGCAATACAGAAAT
GTACCTGATTTTCCGACAACTAGACAACAGCCGTACACGGCAATTCACCCCGCACCATCTGAATTGCGTGATTTCGTCCG
TGTATGAGGGTACAAGAGATGGAGTTGGAGCCGCGCCGTCATACCGCACCAAAAGGGAGAATATTGCTGACTGTCAAGAG
GAAGCAGTTGTCAACGCAGCCAATCCGCTGGGTAGACCAGGCGAAGGAGTCTGCCGTGCCATCTATAAACGTTGGCCGAC
CAGTTTTACCGATTCAGCCACGGAGACAGGCACCGCAAGAATGACTGTGTGCCTAGGAAAGAAAGTGATCCACGCGGTCG
GCCCTGATTTCCGGAAGCACCCAGAAGCAGAAGCCTTGAAATTGCTACAAAACGCCTACCATGCAGTGGCAGACTTAGTA
AATGAACATAACATCAAGTCTGTCGCCATTCCACTGCTATCTACAGGCATTTACGCAGCCGGAAAAGACCGCCTTGAAGT
ATCACTTAACTGCTTGACAACCGCGCTAGACAGAACTGACGCGGACGTAACCATCTATTGCCTGGATAAGAAGTGGAAGG
AAAGAATCGACGCGGCACTCCAACTTAAGGAGTCTGTAACAGAGCTGAAGGATGAAGATATGGAGATCGACGATGAGTTA
GTATGGAtTcATCCAGACAGTTGCTTGAAGGGAAGAAAGGGATTCAGTACTACAAAAGGAAAATTGTATTCGTACTTCGA
AGGCACCAAATTCCATCAAGCAGCAAAAGACATGGCGGAGATAAAGGTCCTGTTCCCTAATGACCAGGAAAGTAATGAAC
AACTGTGTGCCTACATATTGGGTGAGACCATGGAAGCAATCCGCGAAAAGTGCCCGGTCGACCATAACCCGTCGTCTAGC
CCGCCCAAAACGTTGCCGTGCCTTTGCATGTATGCCATGACGCCAGAAAGGGTCCACAGACTTAGAAGCAATAACGTCAA
AGAAGTTACAGTATGCTCCTCCACCCCCCTTCCTAAGCACAAAATTAAGAATGTTCAGAAGGTTCAGTGCACGAAAGTAG
TCCTGTTTAATCCGCACACTCCCGCATTCGTTCCCGCCCGTAAGTACATAGAAGTGCCAGAACAGCCTACCGCTCCTCCT
GCACAGGCCGAGGAGGCCCCCGAAGTTGTAGCGACACCGTCACCATCTACAGCTGATAACACCTCGCTTGATGTCACAGA
CATCTCACTGGATATGGATGACAGTAGCGAAGGCTCACTTTTTTCGAGCTTTAGCGGATCGGACAACTCTATTACTAGTA
TGGACAGTTGGTCGTCAGGACCTAGTTCACTAGAGATAGTAGACCGAAGGCAGGTGGTGGTGGCTGACGTTCATGCCGTC
CAAGAGCCTGCCCCTATTCCACCGCCAAGGCTAAAGAAGATGGCCCGCCTGGCAGCGGCAAGAAAAGAGCCCACTCCACC
GGCAAGCAATAGCTCTGAGTCCCTCCACCTCTCTTTTGGTGGGGTATCCATGTCCCTCGGATCAATTTTCGACGGAGAGA
CGGCCCGCCAGGCAGCGGTACAACCCCTGGCAACAGGCCCCACGGATGTGCCTATGTCTTTCGGATCGTTTTCCGACGGA
GAGATTGATGAGCTGAGCCGCAGAGTAACTGAGTCCGAACCCGTCCTGTTTGGATCATTTGAACCGGGCGAAGTGAACTC
AATTATATCGTCCCGATCAGCCGTATCTTTTCCACTACGCAAGCAGAGACGTAGACGCAGGAGCAGGAGGACTGAATACT
GACTAACCGGGGTAGGTGGGTACATATTTTCGACGGACACAGGCCCTGGGCACTTGCAAAAGAAGTCCGTTCTGCAGAAC
CAGCTTACAGAACCGACCTTGGAGCGCAATGTCCTGGAAAGAATTCATGCCCCGGTGCTCGACACGTCGAAAGAGGAACA
ACTCAAACTCAGGTACCAGATGATGCCCACCGAAGCCAACAAAAGTAGGTACCAGTCTCGTAAAGTAGAAAATCAGAAAG
CCATAACCACTGAGCGACTACTGTCAGGACTACGACTGTATAACTCTGCCACAGATCAGCCAGAATGCTATAAGATCACC
TATCCGAAACCATTGTACTCCAGTAGCGTACCGGCGAACTACTCCGATCCACAGTTCGCTGTAGCTGTCTGTAACAACTA
```

FIG. 3B

TCTGCATGAGAACTATCCGACAGTAGCATCTTATCAGATTACTGACGAGTACGATGCTTACTTGGATATGGTAGACGaGA
CAGTCGCaTGCCTGGATACTGCAACCTTCTGCCCCGCTAAGCTTAGAAGTTACCCGAAAAAACATGAGTATAGAGCCCCG
AATATCCGCAGTGCGGTTCCATCAGCGATGCAGAACACGCTACAAAATGTGCTCATTGCCGCAACTAAAAGAAATTGCAA
CGTCACGCAGATGCGTGAACTGCCAACACTGGACTCAGCGACATTCAATGTCGAATGCTTTCGAAAATATGCATGTAATG
ACGAGTATTGGGAGGAGTTCGCTCGGAAGCCAATTAGGATTACCACTGAGTTTGTCACCGCATATGTAGCTAGACTGAAA
GGCCCTAAGGCCGCCGCACTATTTGCAAAGACGTATAATTTGGTCCCATTGCAAGAAGTGCCTATGGATAGATTCGTCAT
GGACATGAAAAGAGACGTGAAAGTTACACCAGGCACGAAACACACAGAAGAAAGACCGAAAGTACAAGTGATACAAGCCG
CAGAACCCCTGGCGACTGCTTACTTATGCGGGATTCACCGGGAATTAGTGCGTAGGCTTACGGCCGTCTTGCTTCCAAAC
ATTCACACGCTTTTTGACATGTCGGCGGAGGATTTTGATGCAATCATAGCAGAACACTTCAAGCAAGGCGACCCGGTACT
GGAGACGGATATCGCATCATTCGACAAAAGCCAAGACGACGCTATGGCGTTAACCGGTCTGATGATCTTGGAGGACCTGG
GTGTGGATCAACCACTACTCGACTTGATCGAGTGCGCCTTTGGAGAAATATCATCCACCCATCTACCTACGGGTACTCGT
TTTAAATTCGGGGCGATGATGAAATCCGGAATGTTCCTCACACTTTTTGTCAACACAGTTTTGAATGTCGTTATCGCCAG
CAGAGTACTAGAAGAGCGGCTTAAAACGTCCAGATGTGCAGCGTTCATTGGCGACGACAACATCATACATGGAGTAGTAT
CTGACAAAGAAATGGCTGAGAGGTGCGCCACCTGGCTCAACATGGAGGTTAAGATCATCGACGCAGTCATCGGTGAGAGA
CCACCTTACTTCTGCGGCGGATTTATCTTGCAAGATTCGGTTACTTCCACAGCGTGCCGCGTGGCGGATCCCCTGAAAAG
GCTGTTTAAGTTGGGTAAACCGCTCCCAGCCGACGACGAGCAAGACGAAGACAGAAGACGCGCTCTGCTAGATGAAACAA
AGGCGTGGTTTAGAGTAGGTATAACAGGCACTTTAGCAGTGGCCGTGACGACCCGGTATGAGGTAGACAATATTACACCT
GTCCTACTGGCATTGAGAACTTTTGCCCAGAGCAAAAGAGCATTCCAAGCCATCAGAGGGGAAATAAAGCATCTCTACGG
TGGTCCTAAATAGTCAGCATAGTACATTTCATCTGACTAATACTACAACACCACCACCtctagaCGCGTAGAtctcacgt
gagcatgcaggccttgggCCCAATGATCCGACCAGCAAAACTCGATGTACTTCCGAGGAACTGATGTGCATAATGCATCA
GGCTGGTACATTAGATCCCCGCTTACCGCGGGCAATATAGCAACACTAAAAACTCGATGTACTTCCGAGGAAGCGCAGTG
CATAATGCTGCGCAGTGTTGCCACATAACCACTATATTAACCATTTATCTAGCGGACGCCAAAAACTCAATGTATTTCTG
AGGAAGCGTGGTGCATAATGCCACGCAGCGTCTGCATAACTTTTATTATTTCTTTTATTAATCAACAAAATTTTGTTTTT
AACATTTCAAAAAAAAAAAAAAAAAAAAAAAAAAAAAAAAAAAAAAAAAGGGAATTCCCAACTTGTTTATTGCAGCTTATAATG
GTTACAAATAAAGCAATAGCATCACAAATTTCACAAATAAAGCATTTTTTTCACTGCATTCTAGTTGTGGTTTGTCCAAA
CTCATCAATGTATCTTATCATGTCTGGATCCGTCGAGACGCGTccaattcgccctatagtgagtcgtattacgcgcgcTT
GGCGTAATCATGGTCATAGCTGTTTCCTGTGTGAAATTGTTATCCGCTCACAATTCCACACAACATACGAGCCGGAAGCA
TAAAGTGTAAAGCCTGGGGTGCCTAATGAGTGAGCTAACTCACATTAATTGCGTTGCGCTCACTGCCCGCTTTCCAGTCG
GGAAACCTGTCGTGCCAGCTGCATTAATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCAGCTCACTCAAAGGCGGTAATACGGT
TATCCACAGAATCAGGGGATAACGCAGGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCAATGCTCACGCTGTAGGTATCTCAGTTCGGTG
TAGGTCGTTCGCTCCAAGCTGGGCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAGGACAGTATTTGGTATCTGCGCTCTG
CTGAAGCCAGTTACCTTCGGAAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAAGGATCTTCACCTAGATCCTTTTAAATTAA
AAATGAAGTTTTAAATCAATCTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCCGCCTCCATCCAGTCTATTAATTGTTGCCGGGAAGCTAG

FIG.3C

```
AGTAAGTAGTTCGCCAGTTAATAGTTTGCGCAACGTTGTTGCCATTGCTACAGGCATCGTGGTGTCACGCTCGTCGTTTG
GTATGGCTTCATTCAGCTCCGGTTCCCAACGATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTCTGAGAATAGTGTATGC
GGCGACCGAGTTGCTCTTGCCCGGCGTCAATACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGTAACCCACTCGTGCACC
CAACTGATCTTCAGCATCTTTTACTTTCACCAGCGTTTCTGGGTGAGCAAAAACAGGAAGGCAAAATGCCGCAAAAAAGG
GAATAAGGGCGACACGGAAATGTTGAATACTCATACTCTTCCTTTTTCAATATTATTGAAGCATTTATCAGGGTTATTGT
CTCATGAGCGGATACATATTTGAATGTATTTAGAAAAATAAACAAATAGGGGTTCCGCGCACATTTCCCCGAAAAGTGCC
AC
```

FIG.3D

INDUCIBLE ALPHAVIRAL GENE EXPRESSION SYSTEM

This application claims the benefit of the filing date of provisional application 60/079,562 filed on Mar. 27, 1998, which is herein incorporated by reference.

BACKGROUND OF THE INVENTION

1. Field of the Invention

The present invention relates to novel expression vectors which permit tight regulation of gene expression in eucaryotic cells. The invention also relates to methods for producing proteins and RNA molecules and methods for administering proteins and RNA molecules to a plant or animal.

2. Related Art

The ability to precisely control the expression of genes introduced into animal or human cells, or in whole organisms, will enable significant progress in many areas of biology and medicine. For instance, methods that allow the intentional manipulation of gene expression will facilitate the analysis of genes whose expression cannot be tolerated constitutively or at a certain stage of development. These methods will also be valuable for clinical applications such as gene therapy, where the expression of a therapeutic gene must be regulated in accordance with the needs of the patient.

To be of broad benefit, gene regulation techniques must allow for rapid, robust, precise and reversible induction of gene activity. As reviewed in Saez, E. et al., (Curr. Opin. Biotechnol. 8:608–616(1997)), an ideal system should fulfill the following requirements:

1. Specificity—The system must be indifferent to endogenous factors and activated only by exogenous stimuli.
2. Non-interference—The components of the system should not affect unintended cellular pathways.
3. Inducibility—In the inactive state, the basal activity of the system should be minimal, while in the active state high levels of gene expression should be rapidly inducible.
4. Bioavailability of the inducer—Inducing stimuli should rapidly penetrate to the site of interest.
5. Reversibility—Inducing stimuli should clear swiftly to allow the system to rapidly return to the inactive state.

Early methods for controlling gene expression in mammals were based on endogenous elements, such as cytokine response elements or heat-shock proteins. Due to a high level of basal expression in the uninduced state, and pleiotropic effects brought about by general inducing agents, these systems lacked the specificity required to regulate genes in mammalian cells and organisms.

More advance schemes have sought to avoid these problems by constructing switching mechanisms that rely on non-mammalian elements. The fundamental principle of these systems is based on the existence of a small molecule (the inducer) that modifies the activity of a synthetic transcription factor which regulates the expression of the target gene through a heterologous promoter Increased specificity is achieved by selecting inducers that do not affect mammalian physiology, and by assembling chimeric transactivators with minimal homology to natural transcription factors which do not interact with endogenous mammalian promoters.

The most common system currently in use for the regulation of gene expression is the tetracycline-based system (Gossen and Bujard, Proc. Natl. Acad Sci. USA 89:5547 (1992)). This system is based on the continuous expression of a fusion protein where the tetracycline repressor protein (tetR) is converted into an activator by fusion to the transcriptional activation domain of the VP16 protein. In the absence of tetracycline, this chimeric tetracycline transactivator (tTA) activates gene expression through binding to a multimer of the natural tetR binding site (tetO) placed upstream of a minimal promoter. In the presence of tetracycline, the tTA undergoes a conformational change that prevents it from binding to the tetO site, thereby arresting expression of the target gene. Because of its significant advantages over the existing approaches, the tTA system is highly useful for inducible gene expression and this system has been successfully used for the production of a number of proteins (Wimmel et al., Oncogene 9:995 (1994); Fruh et al., EMBO J. 13:3236 (1994); Yu et al., J. Virol. 70:4530 (1996)).

However, serious problems resulting from the toxicity of the tTA protein have been reported with the tTA system, and several cell types have been shown to be unable to tolerate expression of the tTA protein (Schocket et al., Proc. Natl. Acad. Sci. USA 92:6522 (1995); Howe et al., J Biol. Chem. 23:14168 (1995); Schocket and Schatz, Proc. Natl. Acad. Sci. USA 93:5173 (1996); Bohl et al., Nat. Med. 3:299 (1997)). While the toxicity of tTA in cultured cells encumbers the establishment of stable clones with proper tetracycline regulation, this tTA toxicity is a more significant problem in gene therapy and may prevent the use of the tTA system in gene therapy altogether.

A further problem of the tTA system is its notable degree of basal expression. Basal expression can result from the activation of the reporter constructs in the absence of bound transactivator, and/or the inability of tetracycline to completely quell tTA transactivation. High basal expression limits the inducibility of the system, and prevents the conductance of experiments with highly toxic proteins (Furth et al., Proc. Natl. Acad. Sci. USA 91:9302 (1994); Hennighausen et al., J. Cell. Biochem. 59:463 (1995) Kistner et al., Proc. Natl. Acad. Sci. USA 93:10933 (1996); Hoffmann et al., Nucleic Acids Res. 25:1078 (1997)).

In the case of stable clones or transgenic animals, some of this basal expression can be attributed to interference from chromosomal regions into which the foreign DNA integrates. While all inducible systems are equally susceptible to integration effects, it is possible that the basal activity of the tTA system is due to the fact that this system requires the constant presence of tetracycline to efficiently suppress transcription, something that may not always be attainable, particularly in vivo. Basal expression and the requirement that tetracycline be present to suppress gene expression are reasons why the tTA system is not used in gene therapy.

Two gene control systems based on components of mammalian steroid hormone receptors are known (Saez, E. et al., Curr. Opin. Biotechnol. 8:608–616 (1997)). Both combine a truncated form of the progesterone receptor hormone-binding domain with the yeast GAL4 DNA-binding moiety, and the transactivation domain of VP16 protein. The mutated progesterone receptor moiety fails to bind progesterone, but it retains the ability to bind the progesterone and glucocorticoid antagonist mifepristone (RU486), such that, in the presence of RU486, the fusion protein (called GVLP or TAXI) activates transcription through a multimer of the GAL4 DNA binding site placed upstream of a minimal promoter.

An important advantage of the systems described immediately above is that they appear to have more favorable kinetics than tetracycline approaches because lipophilic hormones are quickly metabolized and have short half-lives in vivo. Further, such hormones may also penetrate less accessible tissues more efficiently than tetracycline. However, the main disadvantage of the hormone receptor systems is their very high level of basal expression. In transient and stable transfections of various cell types, a high level a basal activity dampens the inducibility of theses approaches, resulting in induction ratios that are rarely over 20-fold (Wang et al., *Proc. Natl. Acad. Sci. USA* 91:8180 (1994); Mangelsdorf et al., *Cell* 83:835 (1995); Wang et al., *Nat. Biotech.* 15:239 (1997)).

Another approach to regulating gene expression relies on a method of inducing protein dimerization derived from studies on the mechanism of action of immunosuppressive agents (Saez, E. et al., *Curr. Opin. Biotechnol.* 8:608–616 (1997)). Using a synthetic homodimer of FK506, a general strategy was devised to bring together any two peptides simply by endowing them with the domain of FKBP12 to which FK506 binds. Since immunosuppressive drugs, such as cyclosporin A or rapamycin must be used in this approach, the in vivo application of this protein dimerization approach is very limited.

All of the above mentioned strategies regulate expression by controlling the level of transcription of mRNA. Since this mRNA transcription mechanism is always influenced to some extent by the chromosomal region into which the foreign DNA is inserted, precise regulation fails due to the lack of control over the integration mechanism. Although techniques are available for the site-specific insertion of DNA by homologous recombination, insertion frequencies are far too low to allow this strategy to succeed for gene therapy on a general basis.

Another gene expression system is based on alphaviruses (Lundstrom, K., *Curr. Opin. Biotechnol.* 8:578–582 (1997)). Several members of the alphavirus family, Sindbis (Xiong, C. et al, *Science* 243:1188–1191 (1989); Schlesinger, S., *Trends Biotechnol.* 11:18–22 (1993)), SFV (Liljeström, P. & Garoff, H., *Bio/Technology* 9:1356–1361 (1991)) and others (Davis, N. L. et al., *Virology* 171:189–204 (1989)), have received considerable attention for the use as virus-based expression vectors for a variety of different proteins (Lundstrom, K., *Curr. Opin. Biotechnol.* 8:578–582 (1997); Liljeström, P., *Curr. Opin. Biotechnol.* 5:495–500 (1994)).

Alphaviruses are positive stranded RNA viruses which replicate their genomic RNA entirely in the cytoplasm of the infected cell and without a DNA intermediate (Strauss, J. and Strauss, E., *Microbiol. Rev.* 58:491–562 (1994)). The concept that alphaviruses can be developed as expression vectors was first established nearly ten years ago (Xiong, C. et al., *Science* 243:1188–1191 (1989)). Since then, several improvements have made the use of these RNA replicons as expression vectors more practical (Lundstrom, K., *Curr. Opin. Biotechnol.* 8:578–582 (1997)).

DNA vectors have been developed for both Sindbis (Herweijer, H. et al., *Hum. Gene Ther.* 6:1495–1501 (1995); Dubensky, T. W. et al., *J. Virol.* 70:508–519 (1996)) and SFV (Berglund, P. et al., *Trends Biotechnol.* 14:130–134 (1996)). Eukaryotic promoters are introduced in these vectors upstream from the alphavirus replicase gene (consisting of the four non-structural protein genes (nsP1–4)) which are translated as one or two polyproteins which are then proteolytically cleaved (Strauss, J. and Strauss, E., *Microbiol. Rev.* 58:491–562 (1994)). DNA is transcribed to RNA from the recombinant eukaryotic promoter in the nucleus and transported to the cytoplasm, where the replicase catalyzes the replication of the alphavirus RNA molecule as during normal replication of the alphavirus RNA molecule (Strauss, J. and Strauss, E., *Microbiol. Rev.* 58:491–562 (1994)). Only transient expression of heterologous sequences has been possible until recently due to the cytopathogenicity of the alphavirus replicase (Lundstrom, K., *Curr. Opin. Biotechnol.* 8:578–582 (1997)).

About 20 years ago Weiss et al. (Weiss, B. et al., *J. Virol.* 33:463–474 (1980)) established a persistently infected culture of BHK cells. The mutation responsible for this phenotype has been recently identified (Dryga, S. A. et al., *Virology* 228:74–83 (1997)). Another mutation allowing the regulation of the mRNA transcription via temperature shifts was identified by Burge and Pfefferkorn (Burge, B. W. & Pfefferkorn, E. R., *Virology* 30:203–214 (1966)) and described in more detail by Xiong et al. (Xiong, C. et al., *Science* 243:1188–1191 (1989)).

Vectors containing alphaviral sequences have been developed which show promise for use in DNA immunizations (Hariharan, M. et al, *J. Virol.* 72:950–958 (1998)), ribozyme expression (Smith S. et al., *J. Virol.* 71:9713–9721 (1997)), and in vivo expression of heterologous proteins in mammalian tissues (Altman-Hamamdzic S. et al., *Gene Ther.* 4:815–822 (1997)).

SUMMARY OF THE INVENTION

The present invention provides compositions and methods for regulated expression of proteins or untranslated RNA molecules in recombinant host cells. More specifically, the present invention provides polynucleotides and methods which allow precise regulation of the amount of specific RNA molecules produced in stably transfected recombinant host cells. This precise regulation results from the use of a temperature-sensitive RNA-dependent RNA polymerase (i.e., a replicase) which only replicates RNA molecules, to form new RNA molecules, at permissive temperatures.

In one general aspect, the DNA expression vectors of the invention comprise a 5' promoter which is capable of initiating transcription in vivo, 5' and/or 3' sequences enabling replication of the RNA molecule (cis-acting sequence elements), and a subgenomic promoter 5' to the gene of interest, as well as a sequence of interest which is translatable only after one or more RNA-dependent RNA replication events. These RNA-dependent RNA replication events are catalyzed by a regulatable RNA-dependent RNA polymerase which may be encoded by the same mRNA molecule that is produced by transcription of the DNA vector or by a different mRNA molecule.

In another aspect, the invention provides DNA molecules comprising polynucleotides which encode RNA molecules comprising (a) at least one cis-acting sequence element, (b) a first open reading frame having a nucleotide sequence encoding a non-cytopathic, temperature-sensitive RNA-dependent RNA polymerase, and (c) at least one second nucleotide sequence which encodes one of the following:

(i) a second open reading frame encoding a protein, or portion thereof, wherein the second open reading frame is in a translatable format after one or more RNA-dependent RNA replication events;

(ii) a sequence complementary to all or part of the second open reading frame of (i); and (iii) a sequence encoding an untranslated RNA molecule (e.g., an antisense RNA molecule, tRNA molecule, rRNA molecule, or ribozyme), or complement thereof.

The invention further provides single- and multiple-vector systems for expressing a second nucleotide sequence described above. In a single-vector system, sequences encoding the first open reading frame and the second nucleotide sequence are present on the same nucleic acid molecule. In a multiple-vector system, sequences encoding the first open reading frame, or sub-portions thereof, and the second nucleotide sequence are present on one or more separate nucleic acid molecules.

When sequences encoding the first and second open reading frame are present either on the same nucleic acid molecule or in the same vector (i.e., in a single-vector system), a region will be present 5' to the second open reading frame which inhibits translation of this open reading frame.

The temperature-sensitive replicase may be "cold" or "hot" sensitive and thus will only efficiently catalyze RNA-dependent RNA replication at temperatures either above or below the restrictive temperature. In one embodiment, the DNA molecules of the invention encode an RNA-dependent RNA polymerase that has replicase activity at temperatures below 34° C. and has low or undetectable replicase activity at temperatures of 34° C. and above.

Further provided are RNA transcription products of the DNA molecules of the invention and alphaviral particles containing packaged RNA molecules of the invention. When packaged RNA molecules are produced, the second open reading frame may encode one or more proteins required for such packaging (e.g., Sindbis structural proteins).

In another aspect, the nucleic acid molecules of the invention encode one or more cytokine, lymphokine, tumor necrosis factor, interferon, toxic protein, prodrug converting enzyme, or other protein.

In yet another aspect, the nucleic acid molecules of the invention encode an untranslated RNA molecule, such as an antisense RNA molecule, tRNA molecule, rRNA molecule, or ribozyme.

The invention also provides methods for making recombinant host cells comprising introducing nucleic acid molecules of the invention into host cells. Further provided are recombinant host cells produced by the introduction of nucleic acid molecules of the invention. In one embodiment, some or all of these recombinant host cells contain one or more DNA molecules of the invention which are stably maintained.

The invention further provides the pCYTts vector of SEQ ID NO:1, as well as isolated nucleic acid molecules comprising polynucleotides having the nucleotide sequence of SEQ ID NO:1.

The present invention also provides methods for producing proteins and untranslated RNA molecules in recombinant host cells comprising growing host cells under suitable culture conditions, introducing nucleic acid molecules of the invention into host cells, and recovering the proteins or untranslated RNA molecules produced by the recombinant host cells.

Methods are also provided for the regulated expression of heterologous polypeptides, including cytokines, lymphokines, tumor necrosis factors, interferons, toxic proteins, and prodrug converting enzymes.

Further provided are proteins and untranslated RNA molecules produced by the methods of the invention.

The invention also provides methods for regulating the expression of heterologous proteins in recombinant host cells comprising growing host cells under suitable culture conditions, introducing nucleic acid molecules of the invention into the host cells, and changing the temperature of the host cell culture from either a permissive temperature to a restrictive temperature or a restrictive temperature to a permissive temperature In one embodiment, the nucleic acid molecules of the invention are introduced into prokaryotic or eukaryotic host cells which are then cultured in vitro. In related embodiments, these host cells are cultured in a serum-free or protein-free medium.

Additionally provided are methods for producing proteins in recombinant host cells comprising growing host cells under suitable culture conditions, infecting said host cells with alphaviral particles containing RNA molecules of the invention, and recovering the protein.

Also provided are methods for the introduction and expression of nucleic acid molecules of the invention in recombinant host cells within an individual. When these recombinant host cells are intended to express polypeptide or untranslated RNA sequences in an individual, the nucleic acid molecules of the present invention may be introduced into host cells either in vivo or ex vivo. When the nucleic acid molecules are introduced into host cells ex vivo, the recombinant host cells can either be administered to the individual from which they were obtained or to a different individual. In certain embodiments, the host cells are mammalian keratinocytes, epithelial cells, or fibroblasts which are reintroduced into the same mammal from which they were obtained.

The invention further provides methods for regulating the expression of proteins or untranslated RNA molecules in individuals comprising administering nucleic acid molecules of the invention to individuals and changing the temperature of at least a portion of these individuals from either a permissive temperature to a restrictive temperature or a restrictive temperature to a permissive temperature.

The invention also provides methods for administering proteins and untranslated RNA molecules to individuals comprising administering nucleic acid molecules of the invention to individuals and changing the temperature of at least a portion of the individuals from a restrictive temperature to a permissive temperature.

The invention additionally provides methods for regulating the expression of proteins and untranslated RNA molecules in individuals comprising administering recombinant host cells of the invention to these individuals and changing the temperature of at least a portion of these individuals from either a permissive temperature to a restrictive temperature or a restrictive temperature to a permissive temperature.

In one embodiment, the host cells are obtained from the same individual into which the recombinant host cells are administered. In another embodiment, the recombinant host cells are keratinocytes.

The present invention also provides pharmaceutical compositions comprising nucleic acid molecules of the invention and a pharmaceutically acceptable carrier.

The present invention further provides genetically engineered, non-human animals which contain nucleic acid molecules of the invention in at least some of their cells. Also provided are genetically engineered, non-human animals which contain DNA molecules of the invention stably integrated into the genome of some or all the animal's cells. The invention also provides methods for producing genetically engineered, non-human animals comprising introducing cells containing nucleic acid molecules of the invention into these animals, introducing nucleic acid molecules of the invention into the cells of these animals in vivo, or introducing DNA molecules of the invention into germ line cells to produce transgenic animals containing the sequence of interest in their somatic and germ line cells.

Figure 1:
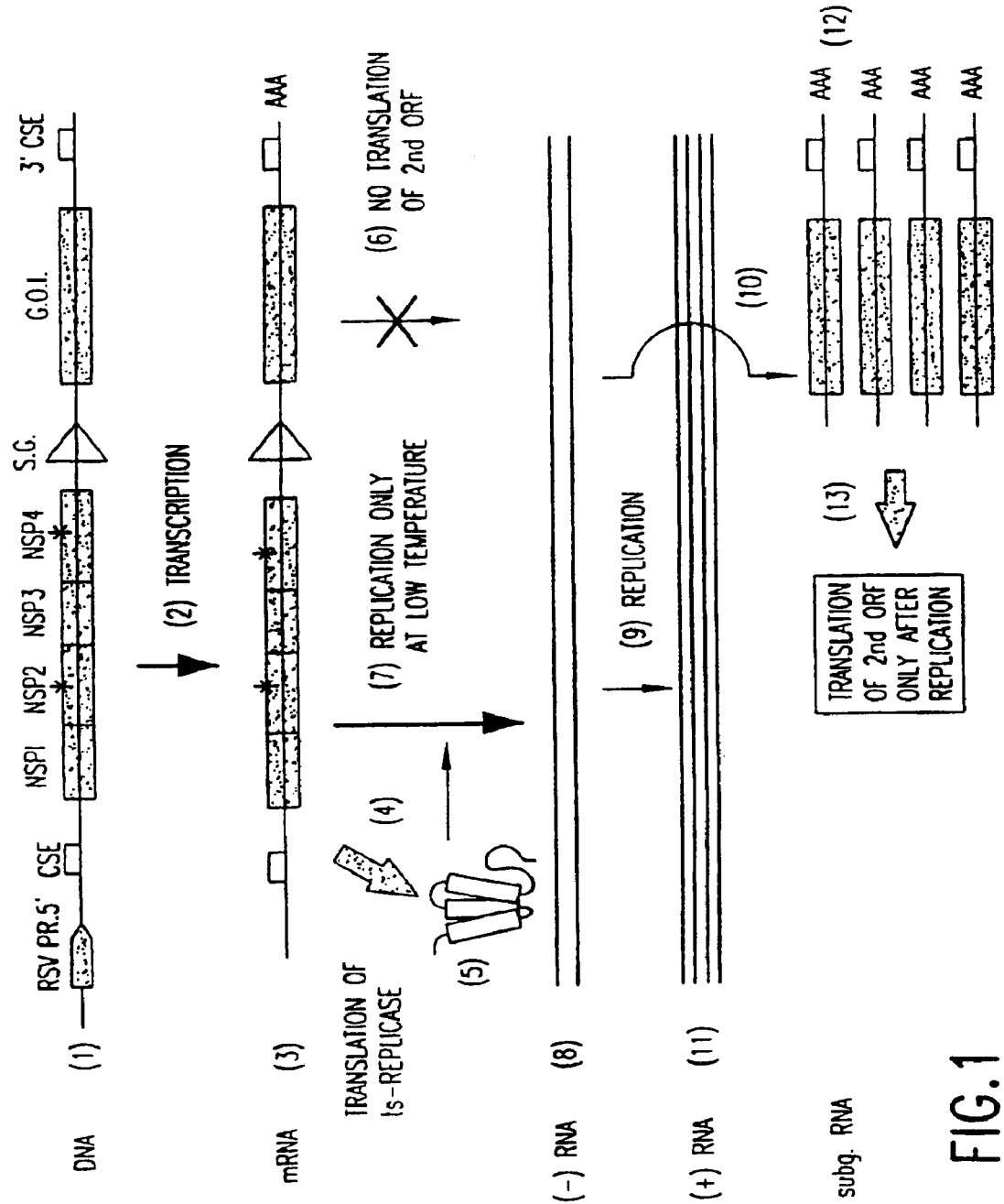
FIG. 1. The DNA of pCYTts (1) is inserted into the nucleus. The eukaryotic promoter (solid horizontal arrow)

drives transcription (2) into mRNA (3). Translation (4) of the first open reading frame (ORF) of the mRNA results in the production of a temperature-sensitive replicase (ts-replicase protein) (5). The second open ORF encoding the gene of interest is not accessible to ribosomes. Thus no translation (6) of the gene of interest occurs. At low temperature the ts-replicase catalyzes replication (7) of the mRNA (3) into full-length (−) strand RNA (8). The ts-replicase also catalyzes subsequent replications (9, 10) into full-length (+) strand RNA (11) and subgenomic RNA (12). The subgenomic RNA (12) is then translated (13) into the protein of interest (not shown). The combination of amplification and qualitative change of the RNA results in unprecedented tightness and regulatability of the expression of the gene of interest.

Abbreviations in FIG. 1 are as follows: Rous Sarcoma Virus promoter (RSV pr.), cis-acting sequence elements (CSE), non-structural proteins 1–4 (nsP1, nsP2, nsP3, nsP4), gene of interest (G.O.I.), and subgenomic promoter (S.G.)

Figure 2:
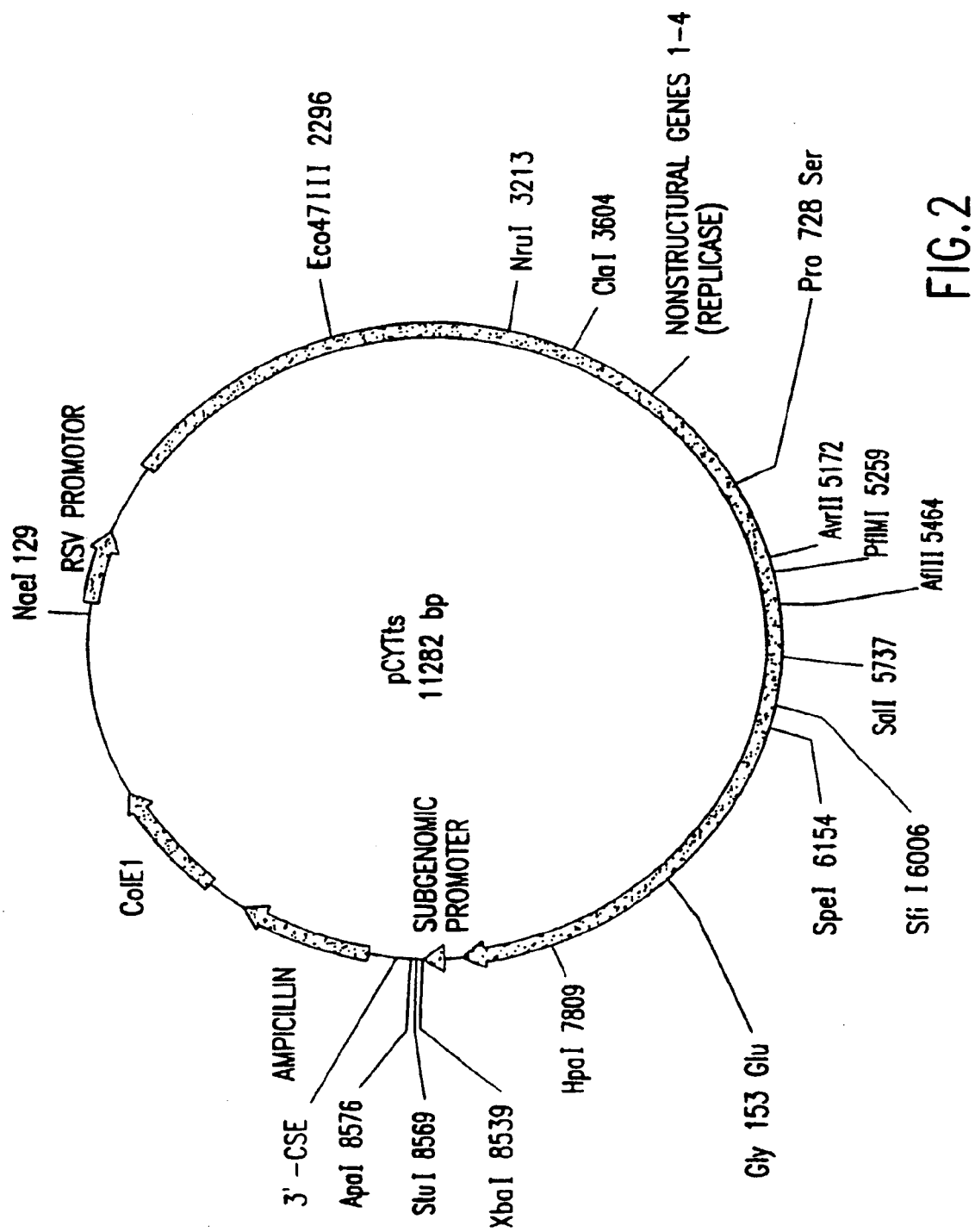

FIG. 2 is a schematic representation of the pCYTts vector. The pCYTts vector contains, in addition to the elements shown in FIG. 1, an ampicillin resistance marker for selection in bacterial cells and a ColE1 sequence which directs high copy number bacterial amplification. The pCYTts vector was prepared as described in Example 1.

FIG. 3A–3D shows the complete cDNA sequence of pCYTts (SEQ ID NO:1).

Figure 4A:
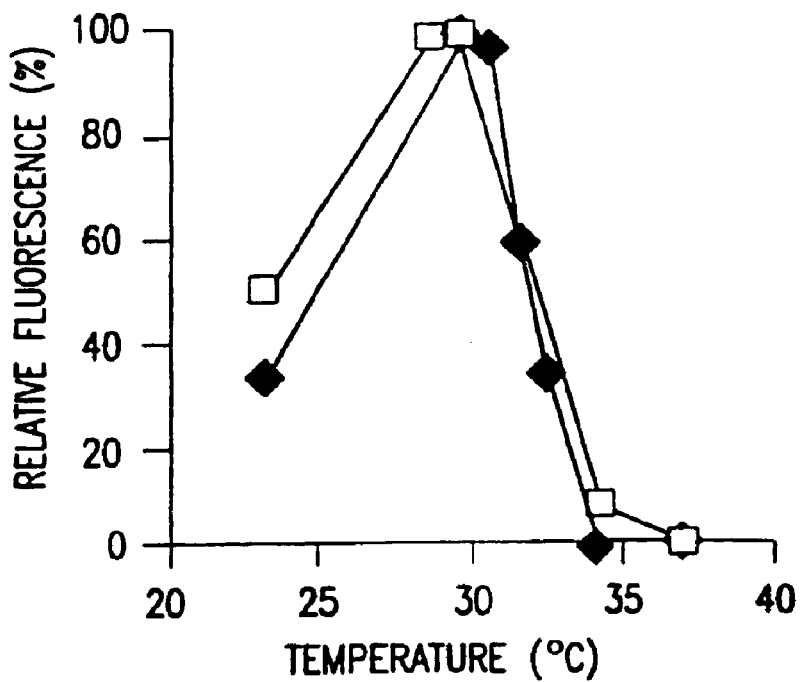
Figure 4B:
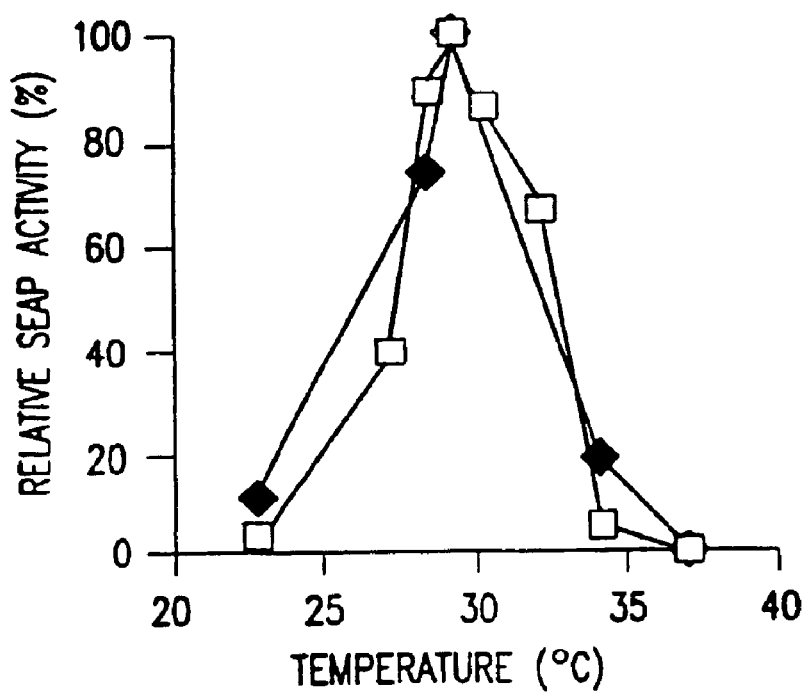

FIG. 4A–4B. GFP (FIG. 4A) and SEAP (FIG. 4B) production at different temperatures. Cells stably transfected with pCYTtsGFP or pCYTtsSEAP were grown for 48 hours at the indicated temperatures (closed diamonds and open squares). Two independent experiments are shown in each of FIG. 4A and FIG. 4B. GFP fluorescence (FIG. 4A) was determined as described in Example 2. SEAP activity (FIG. 4B) was determined colorimetrically as described in Example 3. The maximal protein expression was determined for both proteins to be 29° C. The activities of the proteins were calculated relative to the maximal value at 29° C.

Figure 5A:
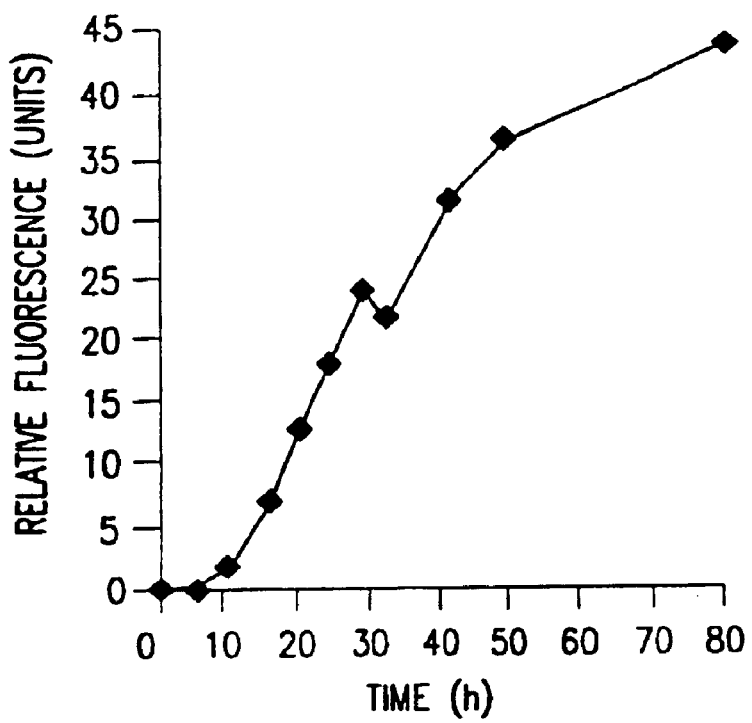
Figure 5B:
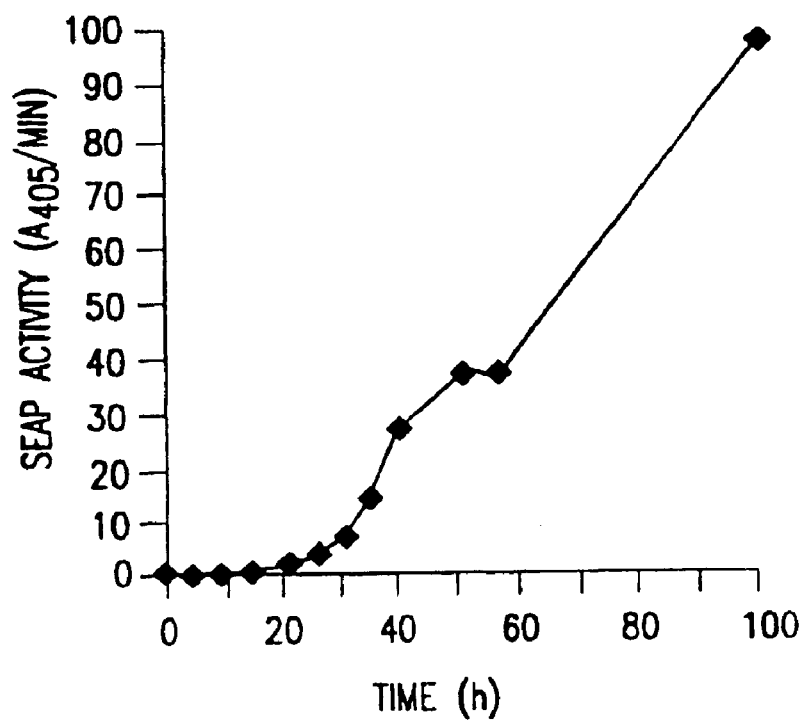

FIG. 5A–5B. Time course of GFP (FIG. 5A) and SEAP (FIG. 5B) production in BHK cells stably transfected with pCYTtsGFP (FIG. 5A) and pCYTtsSEAP (FIG. 5B) at 30° C. GFP production was measured by spectrofluorophotometry and quantified in fluorescence units per $10^6$ cells, as described in Example 2. SEAP production per $10^6$ cells was determined as described in Example 3 by measuring enzymatic activity using p-nitrophenylphosphate as a substrate. The amount of SEAP produced after 80 hours was estimated to be over $10^7$ molecules per cell.

Figure 6A:
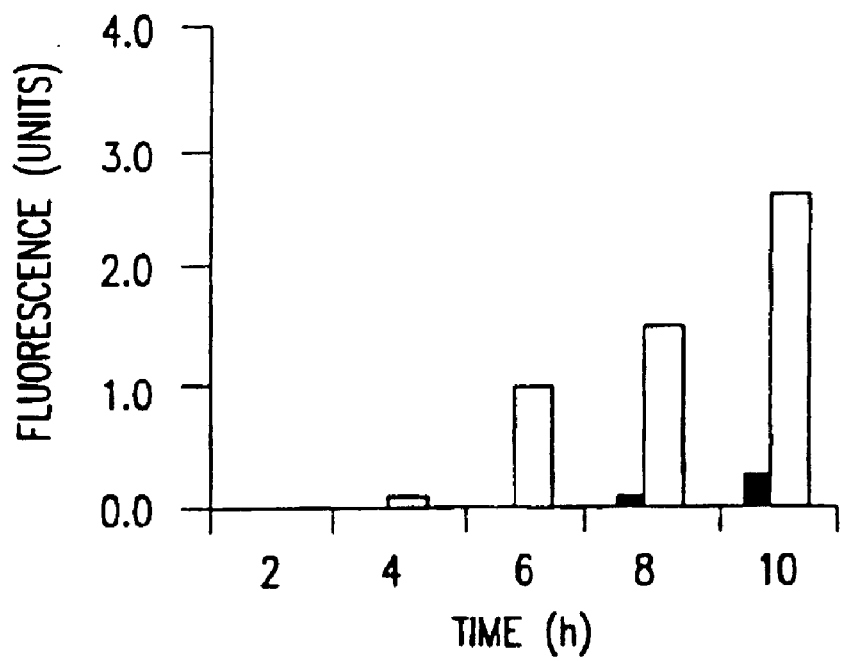
Figure 6B:
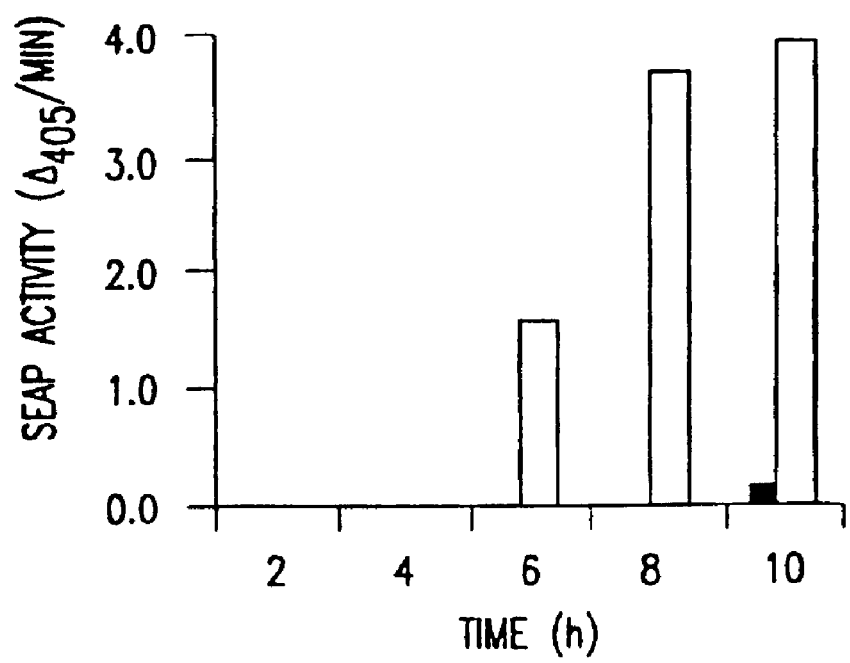

FIG. 6A–6B. The start of GFP (FIG. 6A) or SEAP (FIG. 6B) mRNA transcription in a mixed population of BHK cells stably transfected with pCYTtsGFP or pCYTtsSEAP was determined by measuring the amount of GFP or SEAP produced (see Examples 2 and 3). Cells were incubated for 2, 4, 6, 8 and 10 hours at 29° C. (black boxes), and then grown for another 24 hours at 37° C. (open boxes).

Figure 7A:
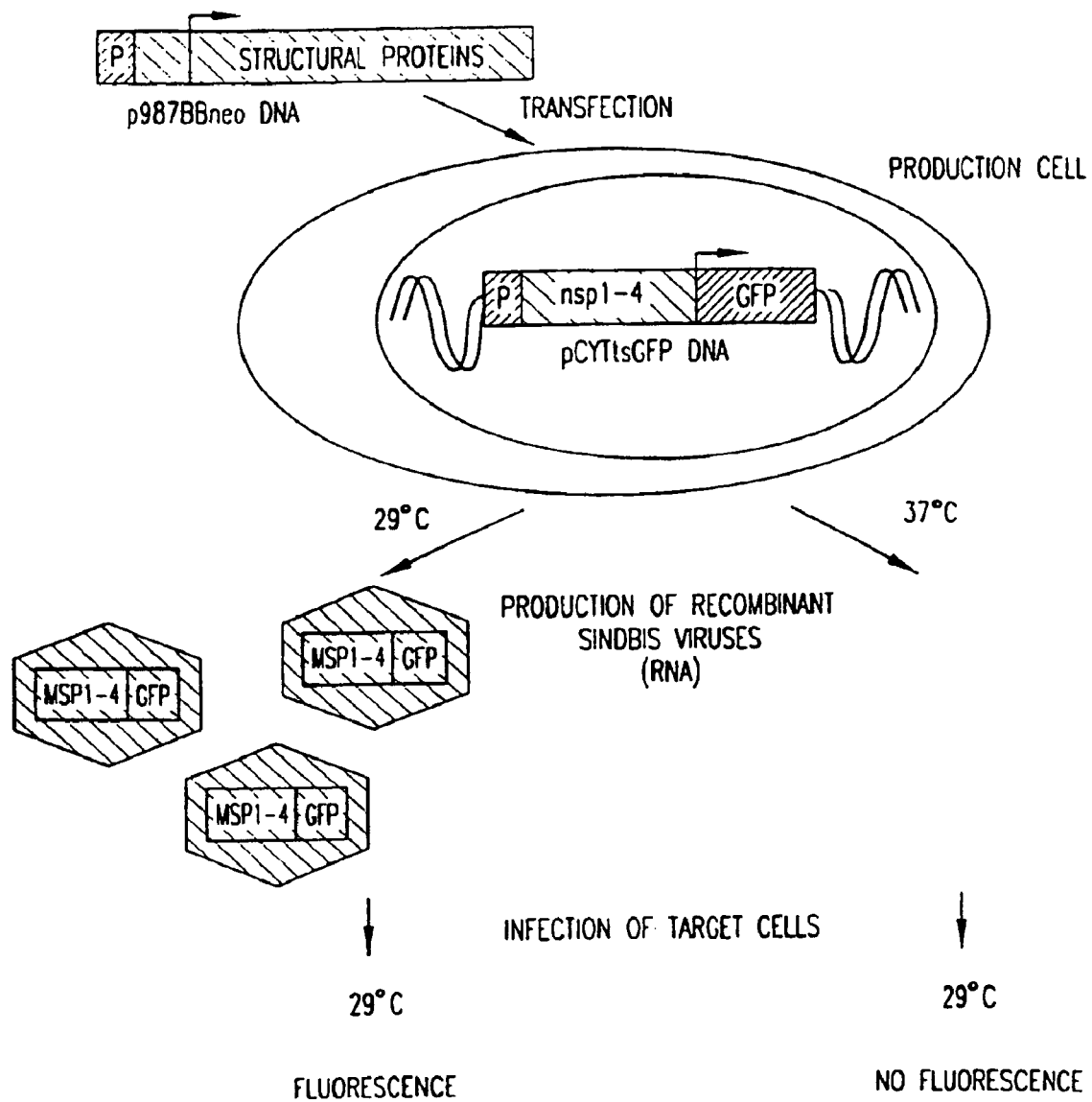
Figure 7B:
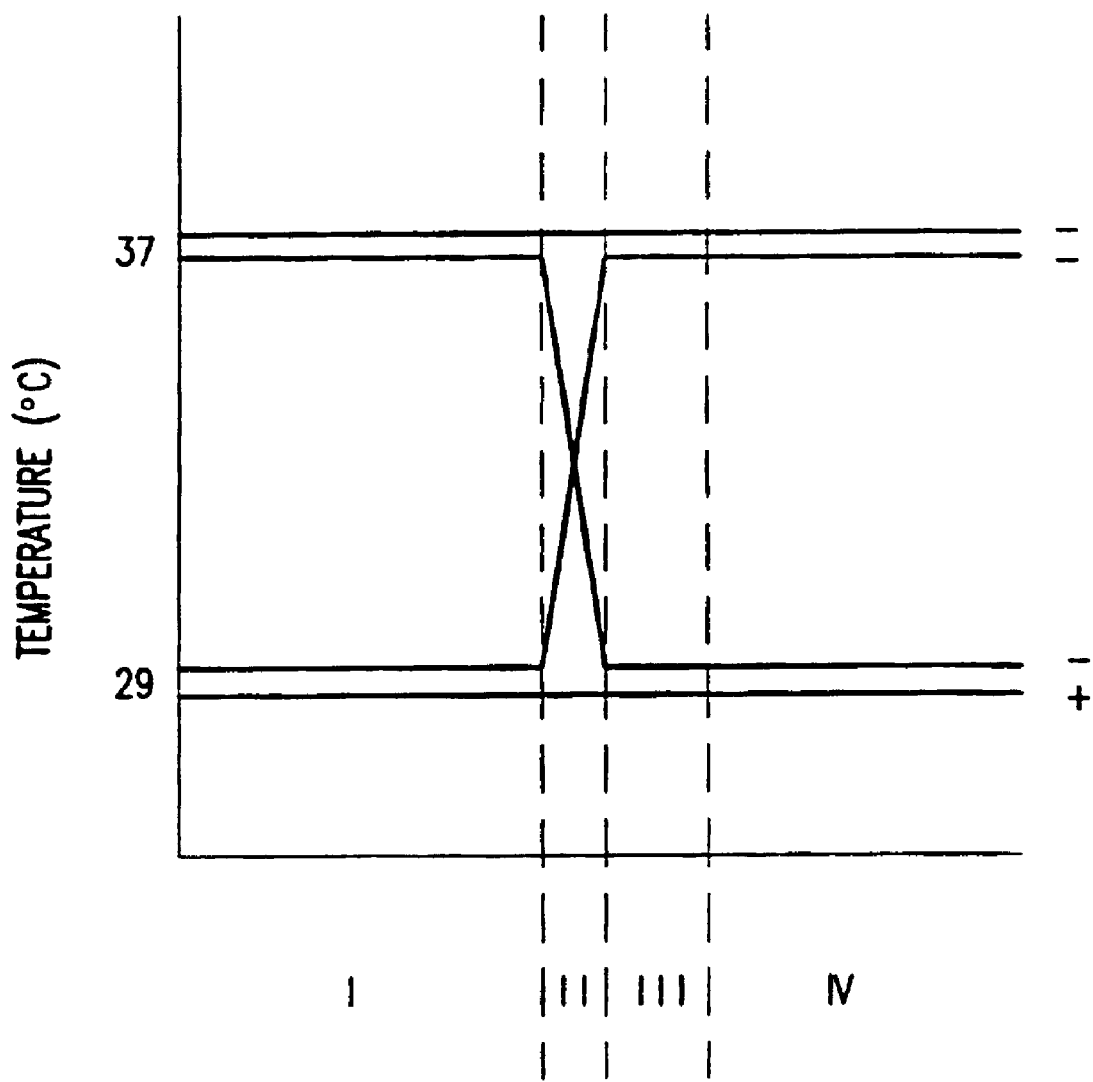

FIG. 7A–7B. These figures show the results of the experiments obtained using stable pCYTtsGFP transfected-BHK cells which were transiently transfected with a plasmid coding for the structural proteins of Sindbis virus. The conditions of the experiments were as follows: (I) incubation phase of transfected BHK cells at 29° C. or 37° C. for 48 hours; (II) the supernatant of the cells was put onto a new BHK cell layer and the cells were shifted to the indicated temperatures; (III) incubation at either 29° C. or 37° C. of the new BHK cell layer for 6 hours; and (IV) washing of the cells and final incubation at 29° C. or 37° C. for 48 hours. Infection events were visualized by the expression of the marker gene GFP as described in Example 2. FIG. 7A shows the result of two separate experiments performed as described above. Fluorescence indicates GFP expression, whereas no fluorescence indicates no detectable GFP expression. FIG. 7B shows the results of four separate experiments performed as described above. The + and − symbols indicate whether GFP expression was detected.

Figure 8A:
Figure 8B:
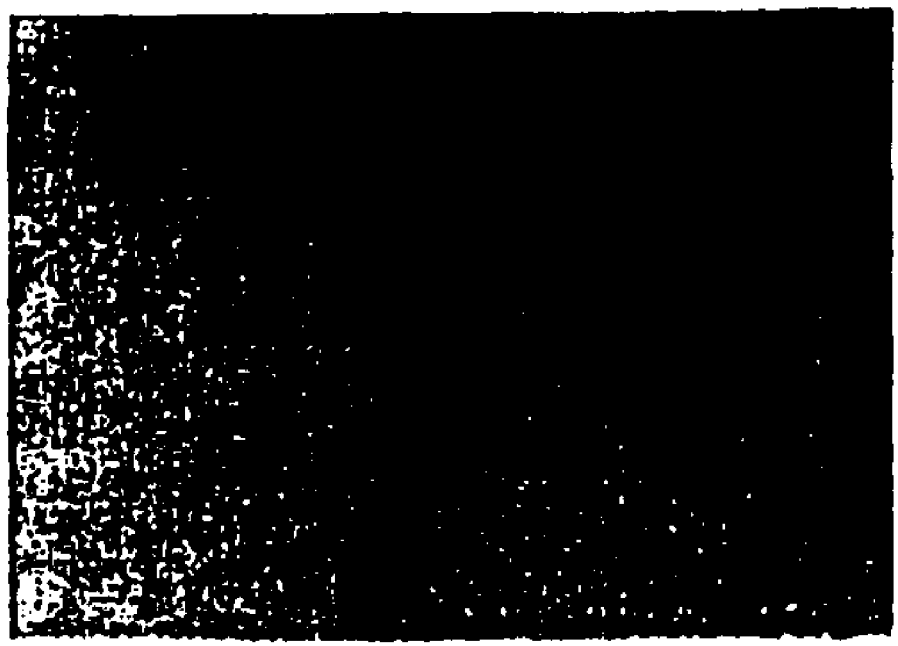

FIG. 8A–8B. Western blot of β-interferon (β-INF) (FIG. 8A) and erythropoietin (EPO) (FIG. 8B) expressed in the pCYTts system. FIG. 8A shows in lane 1 marker, lane 2 positive control, lane 3 supernatant of β-INF expressing cells following incubation at 37° C. for 3 days, lane 4 supernatant of β-INF expressing BHK cells (transient transfection) following incubation at 29° C. for 3 days, lane 5 supernatant of GFP expressing BHK cells, lane 6 marker, lane 7 supernatant of β-INF expressing BHK cells (mixed population) following incubation at 29° C. for 3 days, and lane 8 marker. FIG. 8B shows in lane 1 marker, lane 2 supernatant of EPO expressing cells (transient transfection) following incubation at 29° C. for 5 days, lane 3 supernatant of EPO expressing cells following incubation at 37° C. for 5 days, lane 4 supernatant of GFP expressing BHK cells, and lane 5 marker.

Figure 9:

FIG. 9 shows a Western Blot of EPO. The samples in each lane are as follows: lane 1 EPO standard; lane 2 supernatant of stably pCYTts504-Epo transfected cells at 37° C. for 4 days; lane 3 supernatant of stably pCYTts504-Epo transfected cells at 29° C. for 4 days; lane 4 marker.

Figure 10:
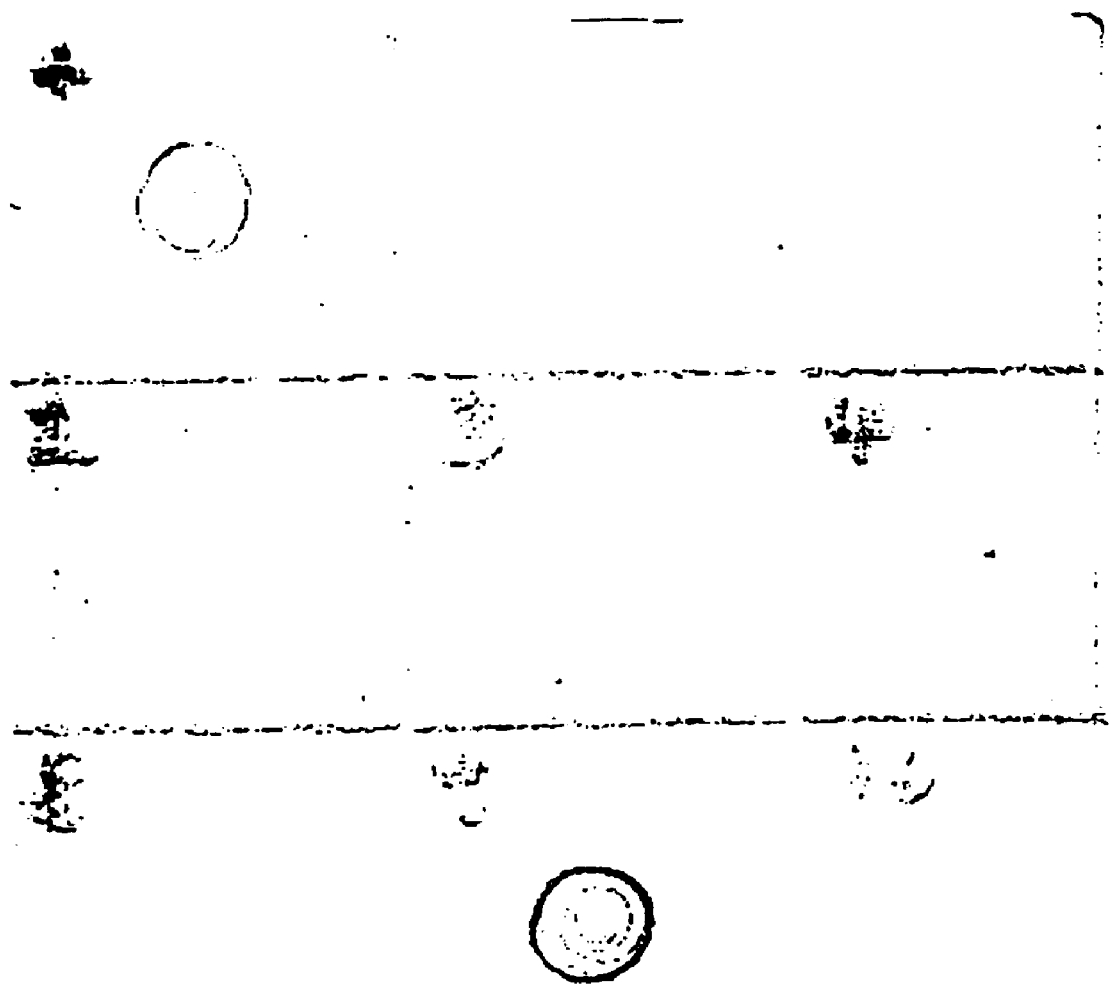

FIG. 10 shows a dot blot of EPO. Spot + shows EPO standard, spots 2 and 10 supernatant of BHK cells (2), spot 3 GFP expressing BHK cells incubated at 30° C., spot 4 1C4 cells incubated at 37° C., spot 8 supernatant of the BHK cells infected with CYTts504 Epo RNA containing viral particles incubated at 37° C. after 2 days, spot 9 supernatant of BHK cell infected with CYTts504Epo RNA containing viral particles incubated at 30° C. for 2 days.

Figure 11:
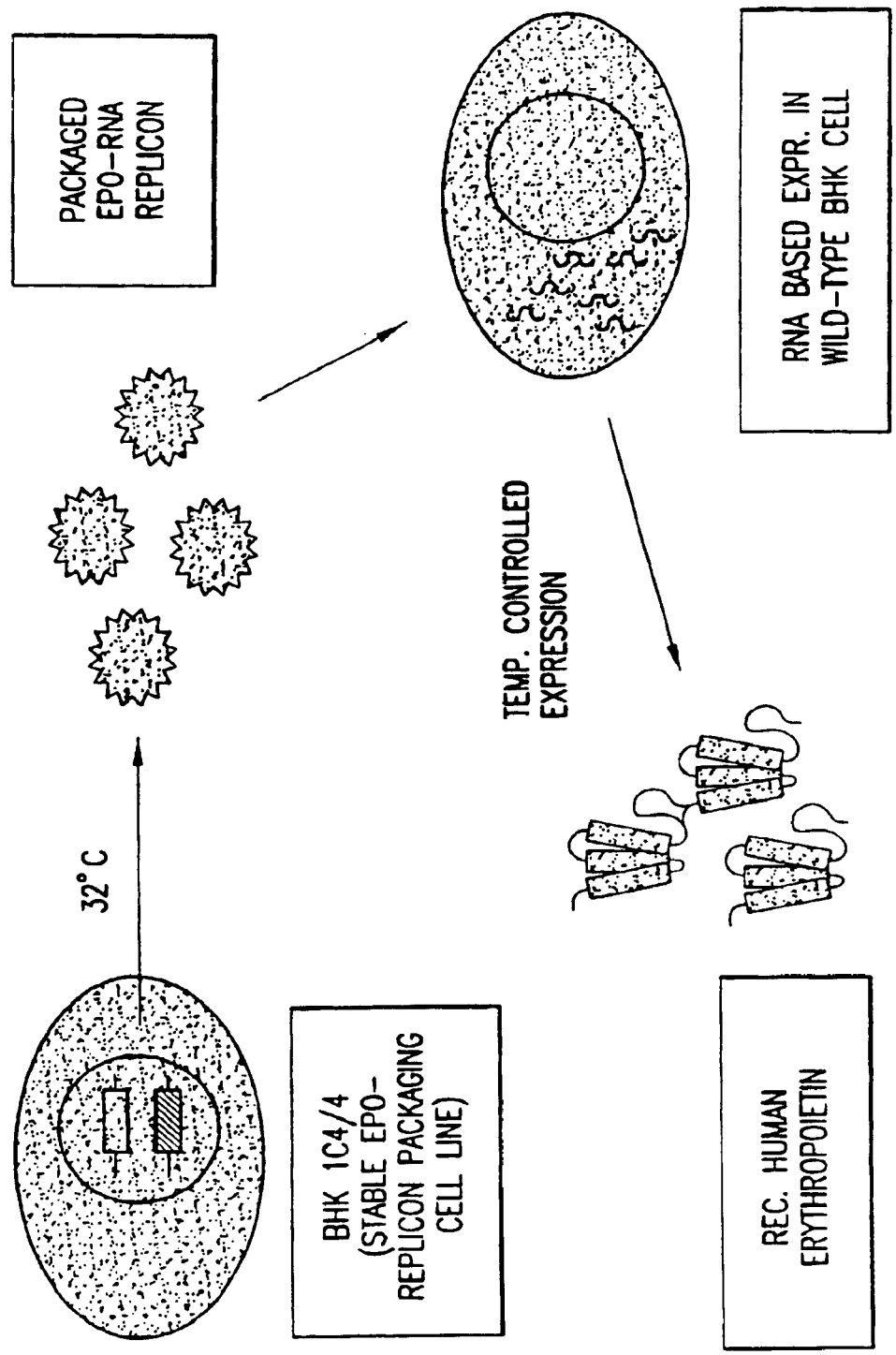

FIG. 11 shows an overview of one embodiment of the invention. This embodiment is directed to the production of recombinant human EPO using host cell infected with packaged RNA replicons produced by baby hamster kidney (BHK) cell line 1C4/4. This BHK cell line was produced as described below in Example 6.

Figure 12:
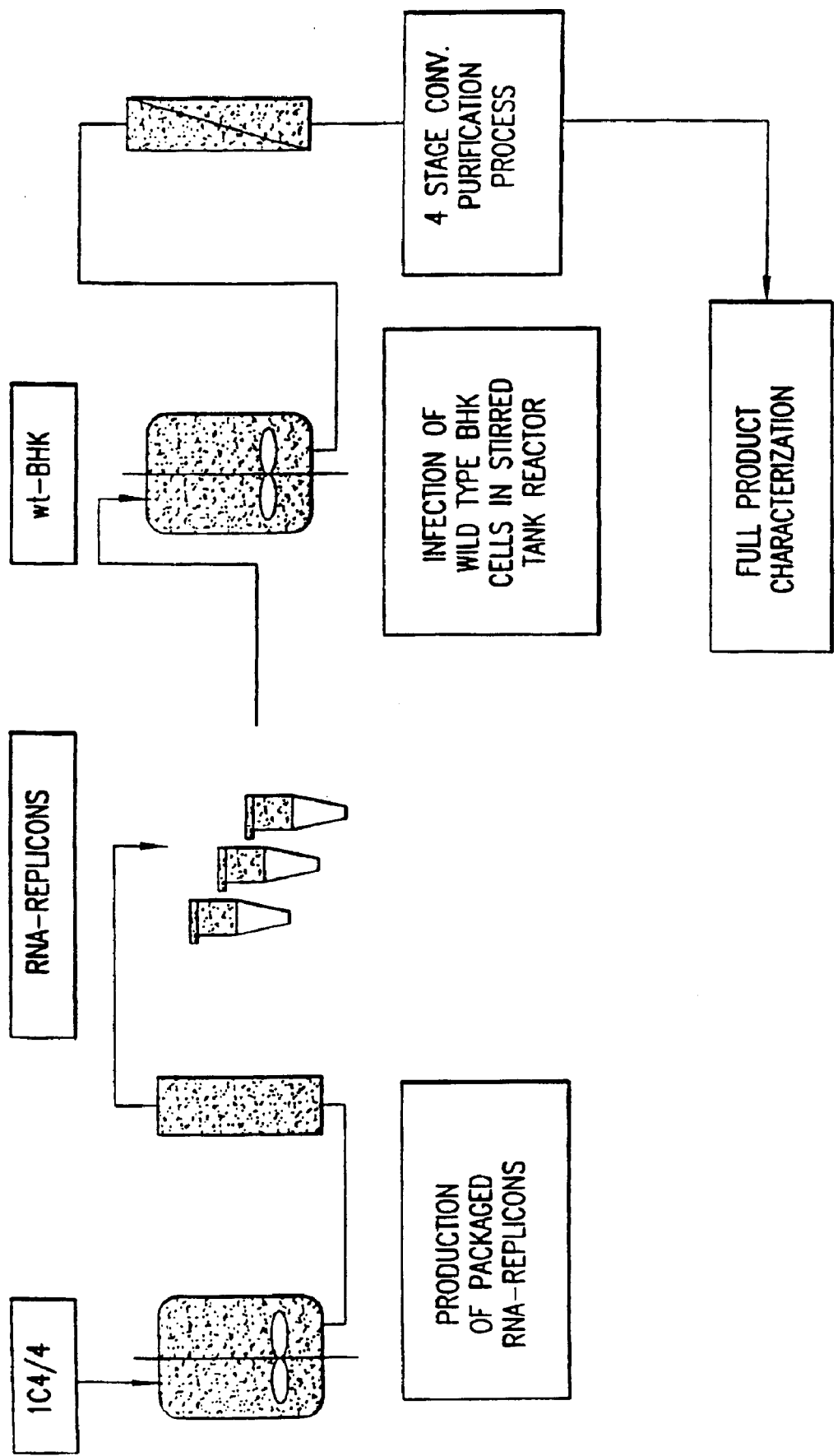

FIG. 12 shows a flow chart of one embodiment of the invention. According to the process described in this figure, RNA replicons are produced by the stable EPO-packaging BHK cell line 1C4/4 and isolated from the culture medium. Wild-type BHK cells, which may be cultured in either serum- or protein-free culture media, are then infected with the replicons. The protein produced by the infected cells is then purified by conventional processes. The process outlined in this figure can be readily scaled up for production of large quantities of human EPO or other proteins.

DETAILED DESCRIPTION OF THE PREFERRED EMBODIMENTS

The present invention is directed to improved expression vectors that are regulatable and non-cytopathic, as well as methods for using these vectors to produce proteins and RNA molecules of interest.

The invention provides polynucleotides and methods which allow the precise regulation of the amount of specific RNA molecules produced in host cells. This precise regulation results from the use of a temperature-sensitive RNA-dependent RNA polymerase which will only replicate RNA molecules, to form additional RNA molecules, at permissive temperatures.

The invention is further directed to inducible gene expression systems employing alphavirus DNA vectors to create stable cell lines carrying genes encoding a non-cytopathic, temperature-sensitive, viral non-structural replicase protein. For example, the activity of the temperature-sensitive replicase used in the Examples, set out below, is switched on by reducing the temperature of the transfected cells from a temperature of 37° C. to a temperature lower than 34° C. Host cell expression at 37° C. is below the level of detection and the induction profile is independent of the chromosomal integration site.

Definitions

The following definitions are provided to clarify the subject matter which the inventors consider to be the present invention.

As used herein, the term "alphavirus" refers to any of the RNA viruses included within the genus Alphavirus. Descriptions of the members of this genus are contained in Strauss and Strauss, *Microbiol. Rev.*, 58:491–562 (1994). Examples of alphaviruses include Aura virus, Bebaru virus, Cabassou virus, Chikungunya virus, Eastern equine encephalomyelitis virus, Fort morgan virus, Getah virus, Kyzylagach virus, Mayoaro virus, Middleburg virus, Mucambo virus, Ndumu virus, Pixuna virus, Tonate virus, Triniti virus, Una virus, Western equine encephalomyelitis virus, Whataroa virus, Sindbis virus (SIN), Semliki forest virus (SFV), Venezuelan equine encephalomyelitis virus (VEE), and Ross River virus.

As used herein, when the term "purified" is used in reference to a molecule, it means that the concentration of the molecule being purified has been increased relative to molecules associated with it in its natural environment. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules.

As used herein, when the term "isolated" is used in reference to a molecule, the term means that the molecule has been removed from its native environment. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

As used herein, the phrase "low or undetectable," when used in reference to gene expression level, refers to a level of expression which is either significantly lower than that seen when the gene is maximally induced (e.g., at least five fold lower) or is not readily detectable by the methods used in the following examples section.

As used herein, the phrase "individual" refers to multicellular organisms and includes both plants and animals. Preferred multicellular organisms are animals, more preferred are vertebrates, even more preferred are mammals, and most preferred are humans.

As used herein, the phrase "cis-acting" sequence refers to nucleic acid sequences to which a replicase binds to catalyze the RNA-dependent replication of RNA molecules. These replication events result in the replication of the full-length and partial RNA molecules and, thus, the alpahvirus subgenomic promoter is also a "cis-acting" sequence. Cis-acting sequences may be located at or near the 5' end, 3' end, or both ends of a nucleic acid molecule, as well as internally.

As used herein, the phrase "RNA-Dependent RNA polymerase" refers to a polymerase which catalyzes the production of an RNA molecule from another RNA molecule. This term is used herein synonymously with the term "replicase."

As used herein, the phrase "non-infective packaged RNA molecules" refers to packaged RNA molecules which will essentially undergo only one round of host cell infection and are not pathogenic. These molecules are thus "infective" but only for a single infectious entry into a host cell and are not capable of reproducing to form additional infectious particles.

As used herein, the term "transcription" refers to the production of RNA molecules from DNA templates catalyzed by RNA polymerases.

As used herein, the phrase "RNA-dependent RNA replication event" refers to processes which result in the formation of an RNA molecule using an RNA molecule as a template.

As used herein, the term "vector" refers to an agent (e.g., a plasmid or virus) used to transmit genetic material to a host cell. A vector may be composed of either DNA or RNA.

As used herein, the term "heterologous sequence" refers to a second nucleotide sequence present in a vector of the invention. The term "heterologous sequence" also refers to any amino acid or RNA sequence encoded by a heterologous DNA sequence contained in a vector of the invention. Heterologous nucleotide sequences can encode proteins or RNA molecules normally expressed in the cell type in which they are present or molecules not normally expressed therein (e.g., Sindbis structural proteins).

As used herein, the phrase "untranslated RNA" refers to an RNA sequence or molecule which does not encode an open reading frame or encodes an open reading frame, or portion thereof, but in a format in which an amino acid sequence will not be produced (e.g., no initiation codon is present). Examples of such molecules are tRNA molecules, rRNA molecules, and ribozymes. Antisense RNA may be untranslated but, in some instances (see Example 11), antisense sequences can be converted to a translatable sense strand from which a polypeptide is produced.

As used herein the phrase "gene therapy" refers to the transfer of heterologous genetic information into cells for the therapeutic treatment of diseases or disorders. The heterologous nucleotide sequence is transferred into a cell and is expressed to produce a polypeptide or untranslated RNA molecule.

As used herein, the phrase "temperature-sensitive" refers to an enzyme which readily catalyzes a reaction at one temperature but catalyzes the same reaction slowly or not at all at another temperature. An example of a temperature-sensitive enzyme is the replicase protein encoded by the pCYTts vector, which has readily detectable replicase activity at temperatures below 34° C. and has low or undetectable activity at 37° C.

As used herein, the phrase "permissive temperature" refers to temperatures at which an enzyme has relatively high levels of catalytic activity.

As used herein, the phrase "restrictive temperature" refers to temperatures at which an enzyme has low or undetectable levels of catalytic activity. Both "hot" and "cold" sensitive mutants are known and, thus, a restrictive temperature may be higher or lower than a permissive temperature.

As used herein, the term "recombinant host cell" refers to a host cell into which one or more nucleic acid molecules of the invention have been introduced.

When the terms "one," "a," or "an" are used in this disclosure, they mean "at least one" or "one or more," unless otherwise indicated.

Alphaviral Vectors of the Invention

The DNA vectors of the present invention are constitutively transcribed in host cells to produce mRNA molecules having two open reading frames. These open reading frames, which may or may not be produced from the same nucleic acid molecule, encode a temperature-sensitive replicase and a heterologous gene of interest. The first open reading frame is translated to produce a temperature-dependent RNA-dependent RNA polymerase. The second open reading frame, encoding all or part of one or more polypeptides of interest, is not translated until after at least one RNA-dependent RNA replication event.

The DNA expression vectors comprise a 5' promoter which is capable of initiating synthesis of RNA in vivo, 5' and/or 3' sequences enabling replication of the RNA molecule (5' and 3' cis acting sequence elements), as well as a sequence of interest which is translatable only after at least one replication event.

Replication is catalyzed by a regulatable RNA-dependent RNA polymerase which is encoded alternatively on the same or on a different mRNA molecule. The sequence of interest may be encoded in sense, plus (+) orientation downstream of a viral RNA promoter. Translation of the coding sequence of the gene of interest is inhibited by a 5' sequence which, in the case of the single-vector system, will generally be the replicase sequence. In the multiple-vector system, a 5' sequence can inhibit translation by having one or more short open reading frames with associated stop codons which lead to the detachment of ribosomes. Similarly, any sequence which inhibits the traveling or binding of ribosomes to the sequence of interest can be used as a 5' sequence which inhibits translation (Voet and Voet, BIOCHEMISTRY, John Wiley & Sons, Inc. (1990)).

Another method for preventing translation of nucleotide sequences in most biological systems involves the insertion of the sequence in an antisense direction. This method of inhibiting translation is based on the principle that translation will generally only occur after the replication of this minus (−) strand RNA into a plus strand having an open reading frame in a sense orientation. The translated sense strand is formed by RNA replication and serves as a template for ribosomes and protein synthesis. As shown in Example 11, production of amino acid sequences can occur even when the gene of interest is inserted into the DNA molecule in an orientation which will result in the formation of antisense RNA sequence 3' to the subgenomic promoter. Thus, the second open reading frame may also comprise a sequence complementary to all or part of the second open reading frame described above and expression of the encoded amino acid sequence will still occur. When the production of an untranslated antisense RNA sequence is desired, the RNA molecule can be designed so that it will not serve as a template for protein synthesis. For example, the RNA can be designed so that an initiation codon is not present.

Untranslated antisense RNA molecules can be used to inhibit translation of mRNA expressed in recombinant host cells. The use of antisense nucleic acid molecules to regulate gene expression is known in the art (see, e.g., Kawamata, H. et al., *Br. J. Cancer* 77:71–78 (1998); Bechler, K., *Biochem. Biophys. Res. Commun.* 241:193–199 (1997); Urakami, S. et al., *Biochem. Biophys. Res. Commun.* 241:24–30 (1997)) and the use of the present vectors to deliver such molecules to host cells is within the scope of the invention.

In addition, instead of a second open reading frame, RNA molecules directly produced by transcription of a DNA sequence of the invention may encode RNA sequences which are neither translated nor present in an antisense orientation. Examples of such untranslated RNA molecules include tRNA molecules, rRNA molecules, and ribozymes. A considerable number of ribozyme sequences with defined catalytic activities are known in the art (see, e.g., Brown, J., *Nucleic Acids Res.* 26:353–354 (1998); Xie, Y. et al., *Proc. Natl. Acad. Sci. USA* 94:13777–13781 (1997); Lavrovsky, Y et al., *Biochem. Mol. Med.* 62:11–22 (1997); Chapman, K. and Szostak, J., *Chem. Biol.* 2:325–333 (1995)). Further, ribozymes have been used to "knockout" the expression of a specific gene in eucaryotic cells as part of a ribozyme-mediated, message deletion strategy (Xie, Y. et al., *Proc. Natl. Acad. Sci. USA* 94:13777–13781 (1997)). Additionally, alphaviral replicons have been used to express a functional ribozyme in mammalian cells (Smith S. et al., *J. Virol.* 71:9713–9721 (1997)). The regulated expression of such ribozymes, and other untranslated RNA molecules, is thus within the scope of the present invention.

The invention is exemplified by the schematic diagram shown in FIG. 1. These embodiments of the invention are directed to DNA vectors which are transcribed to produce a mRNA molecule having two open reading frames, which encode a replicase and a gene of interest. The DNA vectors contain a promoter sequence which drives transcription of these vectors to produce mRNA molecules having coding sequences of both open reading frames. The mRNA sequences of the first open reading frame are translated to produce a replicase required for the expression of the RNA sequences of the second open reading frame. The second open reading frame encodes one or more proteins of interest.

Further, once the first mRNA molecule has been transcribed from the DNA vector, additional RNA-dependent RNA replication events can occur to amplify the first mRNA sequence and to produce RNA molecules with strand polarity which is the opposite of the first mRNA sequence.

As shown in FIG. 1, sections (7)–(8), (10), and (12)–(13), the second open reading frame of a DNA molecules of the invention will only be expressed after partial replication of a full-length RNA molecule. This partial replication of the full-length RNA molecules is driven by a promoter sequence composed of RNA (e.g., an alphaviral subgenomic promoter sequence).

While the gene of interest may be encoded by the same RNA molecule as the replicase protein, this gene may also be encoded by a separate RNA molecule. Thus, the invention further provides both single- and multiple-vectors systems for expressing a gene of interest.

In a single-vector system of the invention, sequences encoding the first open reading frame and the second nucleotide sequence are components of the same nucleic acid molecule. Thus, all of the components required for regulated expression of the gene of interest are contained in a single nucleic acid molecule (i.e., DNA or RNA).

In a multiple-vector system of the invention, sequences encoding the first open reading frame, or sub-portions thereof, and the second nucleotide sequence are components of different nucleic acid molecules. These multiple-vector systems thus may comprise two or more nucleic acid molecules. For example, nsP2, nsP4, and the gene of interest can each be encoded by different DNA vectors. Further, one or more of these DNA vectors can be designed to stably integrate into the host cell genome. When expression of a gene of interest is desired in a cell type containing one or more stably integrated DNA molecules of the invention, expression of the gene of interest will require the introduction of nucleic acid molecules (DNA or RNA) encoding the components of the system into the cells not present in the integrated molecule(s).

While any functional promoter can be used to drive the transcription of mRNA from the DNA vector, the promoter is preferably a constitutive RNA polymerase II promoter (e.g., Rous Sarcoma Virus (RSV), cytomegalovirus (CMV), simian virus 40 (SV40), myeloproliferative sarcoma virus (MPSV), glucocorticoid, metallothionein, Herpes simplex virus thymidine kinase (HSVTK), human immuno deficiency (HIV), mouse mammary tumor virus (MMTV), human polyomavirus BK (BKV), or Moloney murine leukemia virus (MuLV) promoter). Additional promoters suitable for use in the practice of the present invention are known in the art (see, e.g., Lee, A. et al., *Mol. Cells.* 7:495–501 (1997); Artuc, M. et al., *Exp. Dermatol.* 4:317–321 (1995)).

The vector will generally also contain selection markers for cloning and amplification of the vector sequences in procaryotic and eucaryotic organisms. The pCYTts vector, for example, contains an ampicillin resistance marker for positive selection in bacterial host cells and an *E. coli* origin of replication (i.e., ColE1). A considerable number of sequences encoding additional selection markers and origins of replication are known in the art (see, e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)).

The replicase protein coding sequences, the 5' and 3' cis-acting sequences (when present), and the junction sequences containing the subgenomic promoter will normally be derived from a virus, preferably from an alphavirus, most preferably from Sindbis virus.

When using alphavirus replicase proteins, in most instances, it is desirable to convert the cytopathic phenotype of the replicase protein to a non-cytopathic phenotype. Preferred mutations which confer such a phenotype are in the nsp2 gene (e.g., the proline residue at position 726 is replaced with a serine residue). Mutations are known in the art which render the replicase protein non-cytopathic (Weiss et al., *J. Virol.* 33:463–474 (1980); Dryga et al., *Virology* 228:74–83 (1997)). These mutations may be introduced by a number of means, including site directed mutagenesis.

As noted above, when a non-cytopathic Sindbis virus replicase is used in the practice of the invention, a mutation may be introduced in the nsp2 gene. One such mutation results from the exchange of the proline residue at position 726 to another of the 20 natural occurring amino acids, such as a serine (abbreviated as "Pro 726 Ser"). Alternatively, any other mutation rendering the replicase molecule non-cytopathic is within the scope of the invention. The creation and the identification of mutations which render the Sindbis replicase non-cytopathic are described in more detail elsewhere (Weiss et al., *J. Virol.* 33:463–474 (1980); Dryga et al., *Virology* 228:74–83 (1997); patent application WO 97/38087). Further, methods for inducing such mutations are known in the art (see, e.g., Sambrook, J. et al., eds., MOLECULAR CLONING, A LABORATORY MANUAL, 2nd edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)).

Temperature sensitivity (ts) may be conferred, for example, by the introduction of a mutation in the nsp4 gene of the replicase. Preferably, mutations which confer a temperature-sensitive phenotype upon replicase activities are in a protein in complementation group F (Lemm et al., *J. Virol.* 64:3001–3011 (1990)). For example, a temperature-sensitive phenotype may be conferred by changing Gly 153 of nsp4 to Glu. Additionally, any other mutation which renders replicase activity temperature-sensitive can be used in the practice of the invention. Methods for creating and identifying new temperature-sensitive mutants are described by Pfefferkorn (Burge and Pfefferkorn, *Virol.* 30:204–213 (1966); Burge and Pfefferkorn, *Virol.* 30:214–223 (1966)). Further, any method useful for producing and identifying ts mutants which allow for the temperature-sensitive regulation of replicase activity can be employed to generate and isolate such mutants.

While most temperature-sensitive mutants are "hot" sensitive, "cold" sensitive ones are also known (see, e.g., Schwer, B. et al., *Nucleic Acids Res.* 26:803–809 (1998), Mathe, E. et al, *J. Cell Sci.* 111:887–896 (1998), Doedens, J. et al., *J. Virol.* 71:9054–9064 (1997), Patterson, B. et al., *J. Biol. Chem.* 272:27612–27617 (1997)). The temperature-sensitive replicase may be "cold" or "hot" sensitive and thus will catalyze RNA replication only at temperatures either above or below restrictive temperatures. In one embodiment, RNA replication occurs at detectable levels only at temperatures lower than 34° C. In a related embodiment, the pCYTts vector, or variant thereof, is used to express an inserted gene of interest with expression being induced by reducing the temperature of cells containing the vector from 37° C. to a temperature lower than about 34° C. As shown in FIG. 4A-4B, permissive temperatures for the replicase encoded by the pCYTts vector are below about 34° C. Further, expression of the gene of interest increases when the temperature is increased from about 24° C. until a maximal expression level is reached at about 29° C. Additionally, expression of the gene of interest increases as the temperature decreases from about 34° C. Thus, permissive temperatures for the replicase activity encoded by the pCYTts vector are below 34° C., and include temperatures below 24° C., as well as 24° C., 25° C., 26° C., 27° C., 28° C., 29° C., 30° C., 31° C., 32° C., and 33° C. and intervening fractional temperatures up to about 34° C.

In contrast to all previously known regulatable DNA expression systems, the basal level of expression in recombinant host cells containing the pCYTts vector in the inactive state at 37° C. is below the level of detection using standard methods (e.g., those used in the following examples). This low level of expression is apparent from the data presented in FIG. 4A-4B, FIG. 8A-8B, FIG. 9, and FIG. 10. Further, the temperature-dependent induction profile of gene expression appears to be independent of the chromosomal integration site and copy number.

In another embodiment, the sequence of interest and non-cytopathic, regulatable replicase (e.g., nsp2 carrying the Pro 726 Ser mutation and nsp4 carrying the Gly 153 Glu mutation) are encoded by two separate DNA vectors. In such an instance, the DNA vector carrying the sequence of interest carries both cis-acting sequences and a 5' region which inhibits translation of the sequence of interest. The non-cytopathic, regulatable replicase gene can also be encoded by a DNA molecule which is different than the one carrying the sequence of interest. Replication and translation of the sequence of interest in this multi-vectors system is regulatable by temperature as in the one vector system.

The vectors of the invention can be also used to regulate the expression of more than one gene of interest. For example, recombinant host cells can be transfected with more than one nucleic acid molecule of the invention wherein one nucleic acid molecule encodes both the replicase and a polypeptide of interest and additional nucleic acid molecules could encode additional polypeptides of interest. Similarly, when mutations conferring non-cytopathicity and temperature sensitivity are both used, genes encoding polypeptides having suitable mutations (e.g., Pro 726 Ser in nsp2 and Gly 153 Glu in nsp4) may be on separate nucleic acid molecules. Additional variations would be apparent to those skilled in the art.

As shown in Example 11, the sequence of interest can also be inserted in an antisense direction downstream from a functional promoter (e.g., the myeloproliferative sarcomavirus (MPSV) promoter). This construct is converted to a plus (+) strand with sense polarity as shown by the production of the protein of interest. These data demonstrate that antisense DNA fragments can be used with the present invention to express functional polypeptides, or subportions thereof. These data further indicate that the 5' and 3' CSEs may not be necessary for viral transcription when antisense DNA is used as a template for transcription.

The DNA molecules of the invention can also contain packaging signals which direct the packaging of RNA molecules into viral particles. These RNA molecules can be packaged in the presence of wild-type virus or defective helper virus RNA. A significant improvement was made with the development of defective helper RNA molecules (Bredenbeek, P. et al., *J. Virol.* 67:6439–6446 (1993)). These RNA molecules contain cis-acting sequences, required for replication of the full-length transcription product, and subgenomic RNA promoter sequences which drive the expression of the structural protein genes. For example, in cells containing both RNA molecules with packaging signals and the defective helper virus RNA, alphaviral non-structural proteins allow for replication and amplification of the defective helper virus RNA sequences which are translated to produce virion structural proteins. Since the helper virus RNA lacks packaging signals, these molecules are not packaged into assembled virions. Thus, virion particles produced in this way contain essentially only RNA sequences encoding the gene of interest and, generally, other sequences required for temperature-sensitive regulation of gene expression. These non-infective packaged RNA molecules do not contain sequences encoding virion structural proteins and, thus, undergo only one round of host cell infection and are not pathogenic.

Non-infective packaged RNA molecules can be used to infect a culture of suitable host cells simply by addition of the particles to culture medium containing these cells. The preparation of non-infective alpahviral particles is described in a number of sources, including "Sindbis Expression System", Version C, (Invitrogen Catalog No. K750-1).

One application of this system is directed to the temperature-dependent production of non-infective, packaged RNA molecules. These packaged RNA molecules may be produced by a number of means including using recombinant host cells containing two different DNA molecules (e.g., a DNA molecule of the invention and a DNA molecule encoding a helper virus RNA sequence). For example, one of these DNA molecules will encode an RNA molecule which contains packaging signal sequences, sequences encoding a non-cytopathic, temperature-sensitive replicase, and the gene of interest. The other DNA molecule will contain sequences encoding alphaviral structural proteins downstream from an alphavirus subgenomic promoter. Using such a system, viral particles containing only RNA molecules with packaging signals will be produced at permissive temperatures in recombinant host cells. This is so because alphaviral structural proteins will only be produced at a permissive temperature. Additional variations of the above would be apparent to one skilled in the art.

A wide variety of nucleotide sequences of interest can be expressed by the gene expression system of the invention. These sequences include, but are not limited to, sequences encoding lymphokines, cytokines, toxins, enzymes, prodrug converting enzymes, antigens which stimulate immune responses, single chain antibodies, proteins which stimulate or inhibit immune responses, tumor necrosis factors, and various proteins with therapeutic applications (e.g., growth hormones and regulatory factors).

As demonstrated in Example 5, heterologous sequences expressed by the vectors of the invention can also encode erythropoietin (EPO). EPO is a glycoprotein which belongs to the cytokine family and induces terminal erythrocyte development. This protein also regulates red blood cell production.

Heterologous sequences can also encode a cytokine or lymphokine (e.g., β-interferon). Hematopoiesis is regulated by lymphokines and cytokines which stimulate the proliferation and/or differentiation of various hemopoietic cells. Representative examples of cytokines and lymphokines include interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-16 (IL-16), interleukin-17 (IL-17), granulocyte colony stimulating factor (G-CSF), granulocyte-macrophage colony stimulating factor (GM-CSF), macrophage colony stimulating factor (M-CSF), and interferons.

Heterologous sequences can also encode secreted enzymes (e.g., secreted alkaline phosphatase), cytoplasmic enzymes (e.g., green fluorescent protein), or any number of other proteins with therapeutic applications (e.g., human insulin, human coagulation Factor VIII).

The vectors of the invention can also be used to express heterologous sequence encoding cytotoxic polypeptides. Cytotoxic polypeptides act to directly or indirectly inhibit cellular growth or metabolism. Representative examples of toxins include *Shigella* toxin, ricin, *Diphtheria* toxin, *Cholera* toxin, *Pseudomonas* exotoxin A, and *Herpes simplex* virus thymidine kinase (HSVTK). Within other embodiments of this invention, the heterologous sequence encodes a prodrug converting enzyme. A prodrug converting enzyme activates a compound with little or no cytotoxicity into a toxic product. Representative example are HSVTK, alkaline phosphatase, guanine phosphoribosyl transferase, and penicillin-V amidase. Examples of both cytotoxic polypeptides and prodrug converting enzymes are discussed in numerous sources including PCT/US97/06010, EP 0716148, and WO 96/17072.

Nucleotide sequences which may be used with the vectors of the invention include untranslated RNA molecules, such as antisense sequences, RNase P targeted sequences which induce gene down-regulation, and ribozymes. Smith S. et al. (*J. Virol.* 71:9713–9721 (1997)) describes alphaviral vectors used to express ribozyme sequences.

The nucleic acid molecules of the invention can also be used to express virtually any protein, including ones which have not as yet been identified but are encoded by nucleotide sequences contained in, for example, cDNA libraries or host cell chromosomes. Example of such proteins include secreted proteins and proteins from various cellular compartments. Heterologous sequences expressed by the vectors of the invention can encode proteins and RNA molecules from non-human species (e.g., other mammals, plants, fungi, bacteria or viruses). These heterologous sequence may further encodes viral membrane proteins (e.g., HIV gp160) or viral polyproteins (e.g., Sindbis structural proteins).

Sequences of the above described proteins may be readily obtained from a variety of sources, including for example the American Type Culture Collection (ATCC, Rockville, Md.). Alternatively, cDNA sequences which encode the above-mentioned heterologous sequences may be obtained from cells which express such sequences. Methods for isolating both genomic and cDNA sequences encoding genes of interest are well known in the art (see, e.g., Celis, J., ed., CELL BIOLOGY, Academic Press, $2^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). For example, mRNA can be isolated from a cell which expresses a sequence of interest, after which the sequence of interest is reverse transcribed with reverse transcriptase using oligo dT primers, random primers, specific primers, or combinations of each. The cDNA sequences may then be amplified by PCR using heat stable proof-reading polymerases. Alternatively, synthetic DNA sequences may be constructed and expressed with the vectors of the invention.

Nucleotide sequences may be added to the vectors of the invention which result in the production of a fusion protein. For example, such sequences can encode amino acids sequences which are fused to a protein encoded by a gene of interest and confer one or more functional characteristics upon the expression product. These amino acid sequences include sequences which will target the gene product for export from the cell (e.g., a secretory sequence) or to a subcellular compartment (e.g., the nucleus). Such amino acid sequences further include sequences which facilitate purification (e.g., a six His "tag"). Depending on the amino acid sequence and the function imparted by the fused sequence, the added amino acid sequences may or may not be cleaved from the translation product.

Fusion proteins also include proteins which have domains or regions derived from various different proteins. Examples of such a fusion protein are those containing domain II of *Pseudomonas* exotoxin, a domain or amino acid sequence which has binding affinity for a cell surface receptor associated with a particular cell type, and another amino acid sequence with a preselected biological activity. Domain II of *Pseudomonas* exotoxin will translocate across cell membranes. Using this system, fusion proteins can be designed which will bind to specific cells types, will translocate across the cytoplasmic membranes of these cells, and will catalyze predetermined intracellular biological reactions. A system of this type is described in Pastan et al., U.S. Pat. No. 5,705, 163. Methods for identifying amino acid sequences which bind to specific cell types are described in Wu, A., *Nature Biotech.* 14:429–431 (1996).

The vectors of the invention can also contain genetic elements which confer additional functional characteristics such as selection markers, sequences which result in high copy number host cell amplification, and sequences which allow for chromosomal integration of vector sequences.

Markers for the selection of prokaryotic and eukaryotic cells containing vectors the present invention are well known in the art and include tetracycline, ampicillin, neomycin, and kanamycin resistance. DNA molecules containing such sequences are available from numerous sources including Stratagene (11011 North Torrey Pines Road, La Jolla, Calif. 92037, USA) and Promega (2800 Woods Hollow Road, Madison, Wis. 53711, USA). Nucleotide sequences which result in high copy number amplification are also known in the art and include the ColE1 sequence contained in the pCYTts vector.

Recombinant Host Cells

A variety of different recombinant host cells can be produced which contain the vectors of the invention. Alphaviruses are known to have a wide host range. Sindbis virus, for example, infects cultured mammalian, reptilian, and amphibian cells, as well as some insect cells (Clark, H., *J. Natl. Cancer Inst.* 51:645 (1973); Leake, C., *J. Gen. Virol.* 35:335 (1977); Stollar, V. in THE TOGAVIRUSES, R. W. Schlesinger, Ed., Academic Press, (1980), pp. 583–621). Thus, numerous recombinant host cells can be used in the practice of the invention. BHK, COS, Vero, HeLa and CHO cells are particularly suitable for the production of heterologous proteins because they have the potential to glycosylate heterologous proteins in a manner similar to human cells (Watson, E. et al., *Glycobiology* 4:227, (1994)) and can be selected (Zang, M. et al., *Bio/Technology* 13:389 (1995)) or genetically engineered (Renner W. et al., *Biotech. Bioeng.* 47:476 (1995); Lee K. et al. *Biotech. Bioeng.* 50:336 (1996)) to grow in serum-free medium, as well as in suspension.

When recombinant host cells capable of expressing a gene of interest are intended to be inserted into an individual, these cells will generally be from either another individual of the same genus and species or the same individual into which the cells will be inserted. Cells may be obtained from an individual by any number of means including surgical means and tissue biopsy.

Introduction of the polynucleotide vectors into host cells can be effected by methods described in standard laboratory manuals (see, e.g., Sambrook, J. et al., eds., MOLECULAR CLONING, A LABORATORY MANUAL, 2nd. edition, Cold Spring Harbor Laboratory Press, Cold Spring Harbor, N.Y. (1989), Chapter 9; Ausubel, F. et al., eds., CURRENT PROTOCOLS IN MOLECULAR BIOLOGY, John H. Wiley & Sons, Inc. (1997), Chapter 16), including methods such as electroporation, DEAE-dextran mediated transfection, transfection, microinjection, cationic lipid-mediated transfection, electroporation, transduction, scrape loading, ballistic introduction, and infection. Methods for the introduction of exogenous DNA sequences into host cells are discussed in Felgner, P. et al., U.S. Pat. No. 5,580,859.

Non-infective packaged RNA sequences can also be used to infect host cells. These packaged RNA sequences can be introduced to host cells by adding them to the culture medium.

As noted supra, the vectors of the invention may also contain genetic elements which allow for chromosomal integration of vector sequences. Such elements are useful for the stable maintenance of heterologous sequences and include sequences which confer both site-specific and site-independent integration. Site-specific integration (e.g., homologous integration) and site-independent integration, sometimes referred to as "random integration" can be used to introduce heterologous sequences of interest into eucaryotic chromosomes. Descriptions and methods for inserting genetic material into eucaryotic chromosomes are available from numerous sources including Sambrook, J. et al., eds. (MOLECULAR CLONING, A LABORATORY MANUAL, 2nd. edition, Cold Spring Harbor Laboratory Press, Cold Spring Harbor, N.Y. (1989)).

Production of Polypeptides and RNA Molecules

The vectors and recombinant host cells of the invention may be used for the production of polypeptides and RNA molecules. Thus, the invention provides methods for the regulated expression of polypeptides or RNA molecules in host cells, comprising the step of introducing nucleic acid sequences of the present invention into host cells and regulating the temperature to either repress or induce the production of RNA molecules encoding sequences of interest.

Recombinant host cells which express a gene of interest will generally either express this gene in individuals (described in more detail infra) or in in vitro cultures.

When mammalian cells are used as recombinant host cells for the production of polypeptides and RNA molecules, these cells will generally be grown in tissue culture. Methods for growing cells in culture are well known in the art (see, e.g., Celis, J., ed., CELL BIOLOGY, Academic Press, $2^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

The selection of a host cell suited for a particular application will vary with a number of factors including the polypeptide or RNA molecule which is expressed. For example, when a glycoprotein is produced, it is generally desirable to express this protein in a cell type which will glycosylate the protein in a manner similar to that of the native protein.

In one aspect, the present invention provides methods for producing polypeptides and RNA molecules comprising introducing nucleic acid molecules of the invention into recombinant host cells and incubating these cells at a permissive temperature. In a related aspect, the invention provides purified polypeptides and RNA molecules produced according to the methods of the present invention.

Depending on the molecule which is expressed, the molecule may be obtained either from the culture supernatant or by lysing the recombinant host cells. When the expression product is a protein, it will often be possible to obtain the expression product from the culture supernatant. This will be so even when the protein does not have a naturally associated secretory signal. Codons encoding such a signal can be added to the vector sequences of the invention and will result in the expression of a fusion protein which will be secreted from the recombinant host cell. Nucleotide sequences encoding such leader sequences are known in the art and are publically available (see, e.g., pPbac and pMbac vectors, STRATAGENE 1997/1998 CATALOG, Catalog #211503 and #211504, Stratagene, 11011 North Torrey Pines Road, La Jolla, Calif. 92037, USA).

Host cells may also be infected with packaged or unpackaged RNA molecules which have either been transcribed from the DNA molecules of the invention or replicated from such transcribed molecules. Further, these host cells may be infected at a restrictive temperature and then later shifted to a permissive one to activate expression of the gene of interest. The gene product of interest may then be recovered and purified by any suitable means.

The protein expressed from the gene of interest can be recovered and purified from recombinant cell cultures by methods known in the art including ammonium sulfate precipitation, anion or cation exchange chromatography, phosphocellulose chromatography, hydrophobic interaction chromatography, affinity chromatography, hydroxylapatite chromatography, and high performance liquid chromatography. Methods for purifying proteins are described in numerous sources (see, e.g., Celis, J., ed., CELL BIOLOGY, Academic Press, $2^{nd}$ edition, (1998)).

Methods for purifying RNA molecules are also known in the art (see, e.g., Celis, J., ed., CELL BIOLOGY, Academic Press, $2^{nd}$ edition, (1998)). These methods include phenol/chloroform extraction, digestion with DNAses followed by precipitation of the undigested RNA molecules, and column chromatography (e.g., oligo dT column chromatography). Further, RNA molecules can be separated from other cellular material using the single-step guanidinium-thiocyanate-phenol-chloroform method described in Chomczynski and Sacchi, Anal. Biochem. 162:156–159 (1987).

A number of different bioprocess parameters can be varied in order to increase the amount of expression product produced during the cell culture process. The conditions under which the host cells are grown (e.g., medium composition, pH, oxygen concentration, agitation, and, for the case of anchorage-dependent cells, the surface provided and the carrier of that surface) prior to exposure to the nucleic acid molecules of the invention or induction of gene expression influence both the cell density achieved at a given time and the physiological state of the cells. These culture conditions will thus affect the expected cellular response to vector exposure or the induction signal (e.g., shifting to a permissive temperature). Further, the cell culture process-conditions mentioned above can be varied to maximize the production of expression product and, often, the characteristics (e.g., glycosylation pattern) of that expression product.

The overall cell culture process employing nucleic acid molecules of the invention for the production of expression product can be implemented in a variety of bioreactor configurations (e.g., stirred-tank, perfused, membrane enclosed, encapsulated cell, fluidized bed, and air-lift reactors) and scales (from laboratory T-flasks to thousands of liters), chosen to accommodate the requirements of the host cell line utilized (e.g., anchorage dependency, $O_2$ concentrations), to maximize the production of expression product, and to facilitate subsequent recovery and purification of expression product.

The invention is also directed to the production of proteins or RNA molecules of interest using mammalian cells grown in serum-free or protein-free culture media. For example, by long-term culture under conditions restricting serum access or selecting for suspension growth, CHO cell lines are selected which are able to grow in serum-free medium and/or in suspension (Zang. M. et al., Bio/Technology 13:389 (1995)). Further, by genetic modification of CHO K1 cells, a modified cell line designated CHO K1:cycE was obtained which grows as suspended single cells in protein-free culture media (Renner W. et al., Biotech. Bioeng. 47:476 (1995)). CHO mutants (e.g., LEC10 cells) have also been isolated which produce glycoproteins having different glycosylation patterns than those produced in parental CHO cells (Stanley, P., Glycobiology 2:99 (1992)). Alternatively, CHO cells capable of synthesize glycoproteins with correspondingly modified oligosaccharides may be obtained by genetically modifications which alter the activities of enzymes involved in oligosaccharide biosynthesis (Minch et al., Biotechnol. Prog. 11:348 (1995)).

Further, a number of different bioprocess parameters can be varied in order to alter the glycosylation pattern of polypeptide products produced by the recombinant host cells of the invention. These factors include medium composition, pH, oxygen concentration, lack or presence of agitation, and, for the case of anchorage-dependent cells, the surface provided. Thus, the glycosylation pattern of glycoproteins may be altered by choosing the host cell in which these proteins are expressed in and the conditions under which the recombinant host cells are grown.

As explained below, polypeptides and RNA molecules of interest may also be produce in genetically engineered, non-human animals.

Gene Therapy

The vectors of the invention are also useful for gene therapy. When the vectors of the present invention are introduced into cells for gene therapy, the methods and vectors used will generally provide for the stable transfer of vector sequences to the recombinant host cells. In such cases, vector sequences will be maintained in the host cell and will be transferred to cellular progeny. For example, the inclusion of long terminal repeats of retroviruses in gene transfer vectors has been found to confer stable maintenance of vectors sequences in recombinant host cells (Peng, L. et al. *J. Surg. Res.* 69:193–198 (1997); Qing, K. et al., *J. Virol.* 71:5663–5667 (1997)). Thus, chromosomal integration of vector sequences is one mechanism by which such sequences can be stably maintained in recombinant host cells. These sequence can integrate into host cell chromosomes either without regard to chromosomal location or at one or more specific chromosomal loci (e.g., homologous recombination). These recombinant host cells may then be cultured in vitro or introduced into an individual.

The invention provides methods for expressing a sequence of interest in an individual to produce a polypeptide or RNA of interest comprising introducing nucleic acid molecules of the invention into host cells of the individual and regulating the temperature of the recombinant host cells. For example, vectors of the invention which express a "hot" sensitive replicase and contain a sequence encoding a polypeptide or RNA of interest can be introduced into human keratinocytes, epithelial cells, or fibroblasts in vitro and then reintroduced into a human subject. In such an instance, expression of the polypeptide or RNA of interest occurs when the temperature of tissues containing these cells is lowered to a permissive temperature.

The present invention also provides methods for administering polypeptides or RNA molecules to individuals in need thereof comprising introducing nucleic acid molecules of the invention into host cells, introducing the resulting recombinant host cells into these individuals, and inducing expression of the polypeptides or RNA molecules of interest. Similarly, host cells nucleic acid molecules of the invention can be introduced into host cells of an individual in vivo.

Induction of gene expression in individuals occurs by changing the temperature from a restrictive one to a permissive one. When the individual undergoing gene therapy is a human, and it is desirable for expression of the gene of interest to be activated only at specific times, 37° C. will normally be a restrictive temperature and gene induction will result from raising or lowering the temperature to a permissive one. In a similar fashion, when it is desirable for expression of the gene of interest to be inactivated only at specific times, 37° C. will normally be a permissive temperature and gene inactivation will result from raising or lowering the temperature to a restrictive one.

The recombinant host cells introduced into an individual may be of any cell type that will at least be temporarily maintained in the individual or any cell type that will be maintained and at least temporarily retain and express nucleotide sequences of the invention. When the individual into which the recombinant host cells are introduced is a human, the host cells may be of any type which may be implanted in an area where the temperature may be altered between a permissive and a restrictive one by external means. For example, the recombinant host cells may be keratinocytes, epithelial cells, or fibroblasts which have been removed from an individual, transfected with a vector of the present invention, and reimplanted in an area near the surface where the skin temperature normally remains at or close to 37° C. (e.g., an axilla). In such an instance, gene expression can be activated by altering the temperature of tissues containing the recombinant keratinocytes or fibroblasts to a permissive one (e.g., by placing an ice pack or peltier element over the location containing the recombinant host cells). Thus, the induction of expression of the gene of interest requires that the temperature of only a portion of the individuals body (e.g., axilla, arm, leg, hand, foot, neck region, etc.) be changed from a restrictive one to a permissive one.

Recombinant host cells may also be implanted in mammals at locations below surface, cutaneous tissues. One advantage to introducing recombinant host cells in such regions is derived from the temperatures of these tissues being more stably maintained than with surface, cutaneous tissues and, thus, gene expression is less likely to be activated by factors such as changes in climatic conditions. While the locations of suitable regions will vary with a number of factors, including the individual and the individual's normal body temperature, suitable tissues will generally include skin, nervous, and muscle tissues.

In another aspect, the invention provides methods for administering a polypeptide or RNA molecule to an individual in need thereof comprising the in vivo introduction of nucleic acid molecules of the invention into host cells of the individual and inducing expression of heterologous polypeptides or RNA molecules encoded by these nucleic acid molecules. Methods for the in vivo introduction of alphaviral vectors to mammals tissues are described in Altman-Hamamdzic S. et al. (*Gene Ther.* 4:815–822 (1997)).

In a further aspect, methods are provided for administering a polypeptide or RNA molecule to an individual in need thereof by introducing RNA molecules to the cells of the individual. These RNA molecules may be obtained by a variety of methods including in vitro transcription and recombinant host cell expression. The RNA molecules may be introduced into cells of the individual either in vitro or in vivo. Methods for the introducing RNA sequences into host cells of individuals are described in Felgner, P. et al., U.S. Pat. No. 5,580,859.

The invention also provides non-infective, packaged RNA molecules encoding a temperature sensitive replicase useful as gene therapy vectors. These vectors have the advantages of being non-infectious, non-integrating, and express the gene of interest in a temperature-sensitive manner. Vectors of this type are useful for a variety of applications where a single administration of the gene product of interest is desired (e.g., vaccine administration).

The nucleic acid molecules of the invention are useful for the regulated expression of stably integrated heterologous sequences in individuals. In one application, keratinocytes or fibroblasts of a human individual afflicted with diabetes are removed by tissue biopsy, DNA molecules of the invention containing a sequence of interest encoding human insulin are introduced and stably integrated into these cells in vitro. These recombinant host cells are reimplanted in a location near the surface where body temperature is relatively stably maintained (e.g., an axilla). Prior to meal time, or some other time when insulin production is desired, the individual places an ice pack or a peltier element for a specified period of time over the location containing the recombinant host cells to induce expression of the heterologous insulin coding sequences. Further, a warm item may used by the individual to raise the temperature to a permissive one when a cold sensitive replicase is used.

The actual temperature of the item which is placed in contact with the skin will vary with the type of temperature-sensitive mutation used, the individual, the location of the recombinant host cells, the level of gene expression desired, and other factors.

Genetically Engineered, Non-Human Animals

Genetically engineered animals are currently used for the production of heterologous proteins (see, e.g., Jeng, S. et al., *J. Dairy Sci.* 80:3167–3175 (1997); Limonta J. et al., *Immunotechnology* 1:107–113 (1995)). These proteins are often harvested from bodily fluids such as blood, milk and urine (Meade, H. et al., *Nat. Biotechnol.* 16:21–22 (1998); Kerr, D. et al., *Nat. Biotechnol.* 16:75–79 (1998)).

The present invention also provides genetically engineered, non-human animal comprising cells which contain nucleic acid molecules of the present invention. These animals will generally have one or more DNA molecules of the invention stably integrated into their somatic and germ line cells. A number of methods are known in the art for producing animals having DNA molecules of the invention in their germ line cells (see, e.g., Hew, C. et al., U.S. Pat. No. 5,545,808; Jolicoeur, P., U.S. Pat. No. 5,574,206; Mintz, B., U.S. Pat. No. 5,550,316; Wagner, T. et al., U.S. Pat. No. 4,873,191). For example, DNA molecules can be introduced by microinjection into a fertilized, mammalian oocyte between the one-cell and eight-cell stage of embryological development. These oocytes are then implanted in a suitable female to produce founder animals which will stably transmit the heterologous transgene through the germ line to the next generation. Southern blot analysis is generally used to determine whether the genome of any particular individual carries the heterologous DNA sequence.

The genetically engineered animals may also contain nucleic acid molecules of the invention exclusively in somatic cells. Host cells containing these molecules may be implanted into the animal or nucleic acid molecules may be introduced into host cells of the animal in vivo.

Expression of the gene of interest in the cells of a genetically engineered animal may be induced by altering the body temperature of all or part of the animal from a restrictive one to a permissive one. Thus, the choice of the animal used will vary with a number of factors, including the restrictive and permissive temperatures of the replicase employed, the normal body temperature of the animal to be genetically engineered, and the gene of interest. These animals may be either warm-blooded or cold-blooded. For example, Hew, C. et al. (U.S. Pat. No. 5,545,808) describes the production of transgenic fish which express nucleotide sequences linked to an "anti-freeze" gene promoter. Expression of a sequence of interest in such an animal containing a nucleic acid molecule of the invention can be regulated by changing the water temperature the fish is kept in between restrictive and permissive temperatures.

When a warm-blooded animal contains a nucleic acid molecule of the present invention, the normal body temperature of the animal may be either a restrictive one or a permissive one. Further, in many instances expression of the gene of interest will either be induced or repressed in only a portion of the animal at any one time. For example, when the normal body temperature of a warm-blooded animal is a restrictive temperature and the temperature sensitive replicase is "hot" sensitive, the animal may be kept under conditions in which its extremities (e.g., feet, arms legs, etc.) or surface tissues are lowered to a permissive one.

When a warm-blooded animal having cells which contain a nucleic acid molecule of the invention has a normal body temperature which is a permissive one, the gene of interest will generally be expressed in cells in internal regions of the animal. Such animals will be particularly useful for expressing the gene of interest in mammary gland and urothelial tissues. Kerr, D. et al (*Nat. Biotechnol.* 16:75–79 (1998)), for example, describe the production of transgenic animals which express a foreign gene in the cells of their urothelium. These animals excrete the foreign gene product in their urine. Thus, the product of the gene of interest is readily collectable from such animals. Similarly, expression of the gene of interest in mammary gland tissues can result in the gene product being excreted into the animal's milk.

The present invention thus further provides genetically engineered, non-human animals which contain nucleic acid molecules of the invention in at least some of their cells. Also provided are genetically engineered, non-human animals which contain DNA molecules of the invention stably integrated into the genome of some or all the animal's cells. The invention also provides methods for producing genetically engineered, non-human animals comprising introducing cells containing nucleic acid molecules of the invention into these animals, introducing nucleic acid molecules of the invention into the cells of these animals in vivo, or introducing DNA molecules of the invention into germ line cells to produce transgenic animals containing the sequence of interest in their somatic and germ line cells.

Pharmaceutical Compositions

The invention further provides pharmaceutical compositions, comprising polynucleotides of the invention in solution with a physiologically acceptable carrier and in a therapeutically effective amount. The administration of these pharmaceutical compositions may, for example, result in expression of a polypeptide in tissues of an animal which is immunogenic and intended to function as a vaccination. Similarly, the sequence of interest may encode polypeptides or RNA molecules required for the treatment of an active affliction. The administration of a pharmaceutical composition of the invention will thus be intended to have a therapeutic effect in these instances.

The nucleic acid molecules and recombinant host cells of the invention will normally be administered to an individual in a pharmacologically acceptable carrier. A composition is said to be "pharmacologically acceptable" if its administration can be tolerated by a recipient individual. Further, the composition of the invention will be administered in a "therapeutically effective amount" (i.e., an amount that produces a desired physiological effect).

As would be understood by one of ordinary skill in the art, when the DNA molecules or recombinant host cells of the invention are administered to an individual, they may be in a composition which contains salts, buffers, adjuvants, or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1980)).

The therapeutic compositions of the present invention can be administered by various art known means but will normally be administered by injection, infusion or other suitable physical methods. The compositions may alternatively be administered intramuscularly, intravenously, or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

When recombinant host cells are administered to an individual, the number of cells or nucleic acid molecules required to provide a therapeutically effective amount will vary with such factors as the individual's condition, the proteins or RNA molecules intended to be expressed, and the size of the individual.

EXAMPLES

The following enzymes and reagents were used in the experiments described in the examples which follow: Pwo polymerase, dNTPs and restriction enzymes were obtained from Boehringer Mannheim (9115 Hague Road, Indianapolis, Ind. 46250). T4 DNA ligase, fetal calf serum (FCS), bacto-tryptone and yeast extract was obtained from Gibco BRL (P.O. Box 68, Grand Island, N.Y., 14072, USA). Bsp120 I was obtained from MBI Fermentas, Inc. (300 Pearl St. Buffalo, N.Y., 14202, USA). XL-1 Blue competent cells were obtained from Stratagene (11011 North Torrey Pines Road, La Jolla, Calif., 92037, USA). DNA purification kits and Taq polymerase were obtained from QIAGEN, Inc., (9259 Eton Avenue, Chatsworth, Calif., 91311, USA). HP-1 medium was obtained from Cell Culture Technologies (Glattbrugg, Switzerland). All standard chemicals were obtained from Fluka (980 South $2^{nd}$ St., Ronkonkoma, N.Y., 11779, USA), Sigma Chemical Co. (P.O. Box 14508, St. Louis, Mo. 63178, USA), Aldrich (1001 West St. Paul Ave. Milwaukee, Wis., 53233, USA) and all cell culture materials were obtained from Becton Dickinson & Co. (1 Becton Drive, Franklin Lakes, N.J., 07417, USA).

Example 1

Construction of the pCYTts Vector System

Manipulations and sequencing of DNA were carried out by standard procedures. The mutations in nsP2 were introduced by PCR using the following oligonucleotides:
oligo-nsp2 1: 5'-AACATTGAA<u>ATCGAT</u>ATTACAGGGG (SEQ ID NO:2),
oligo-nsp2 2: 5'-CGGGTTATG<u>GTCGAC</u>CGGGC (SEQ ID NO:3),
oligo-nsp2 3: 5'-GTGCCCTCCCCTGAG<u>TTTAAA</u>CAATTCAGGGCCGAACGCG (SEQ ID NO:4), and
oligo-nsp2 4: 5'-GAATTG<u>TTTAAA</u>CTCAGGAGGCACCCTCGTGG (SEQ ID NO:5), the single restriction sites used for first analysis and subsequent cloning (DraI, ClaI and SalI) are underlined. PCR reactions were performed using either oligo-nsp2 1 (SEQ ID NO:2) and oligo-nsp2 3 (SEQ ID NO:4) or oligo-nsp2 2 (SEQ ID NO:3) and oligo-nsp2 4 (SEQ ID NO:5). 100 pmol of each oligo was used and 5 ng of the template DNA (pSinRep5; Xiong, C. et al., Science 243:1188–1191 (1989)) was used in the 100 μl reaction mixture, containing 4 units of Taq or Pwo polymerase, 0.1 mM dNTPs and 1.5 mM $MgSO_4$. All DNA concentrations were determined photometrically using the GeneQuant apparatus (Pharmacia Biotech Inc., 800 Centennial Ave., Piscataway, N.J. 08854). The polymerase was added directly before starting the PCR reaction (starting point was 95° C.). The temperature cycles were as follows: 95° C. for 2 minutes, followed by 5 cycles of 95° C. (45 seconds), 58° C. (30 seconds), 72° C. (90 seconds) and followed by 25 cycles of 95° C. (45 seconds), 68° C. (30 seconds), 72° C. (90 seconds).

The two PCR fragment were purified using Qia spin PCR kit (QIAGEN, Inc., 9259 Eton Avenue, Chatsworth, Calif., 91311) and finally digested in an appropriate buffer using 20 units of SalI and DraI, respectively 20 units of ClaI and DraI. The digestion was performed for 12 hours at 37° C. The DNA fragments were gel-purified (Gene-Clean; Bio 101 Inc., 1070 Joshua Way, Vista, Calif., 92083, USA) and finally ligated into ClaI/SalI digested and gel-purified SinRep5 vector (Xiong, C. et al., Science 243:1188–1191 (1989). The correct sequence of the obtained vector was checked by DNA sequencing of the whole nsP2 gene.

The mutations in nsP4 were also introduced by PCR using the following oligonucleotides:
oligo-nsp4 1: 5'-GGTAGACGAGACAGTC<u>GCATGC</u>CTGGATAC (SEQ ID NO:6),
oligo-nsp4 2: 5'-GTATCCAG<u>GCATGC</u>GACTGTCTCGTCTACC (SEQ ID NO:7),
oligo-nsp4 3: 5'-CAGACCG<u>GTTAAC</u>GCCATAGCG TCG (SEQ ID NO:8), and
oligo-nsp4 4: 5'-CTCTATT<u>ACTAGT</u>ATGGACAGTTGG (SEQ ID NO:9), the singular restriction sites used for the first analysis and the final cloning step (SphI, HpaI and SpeI) are underlined. Two PCR reactions were carried out as described above using either oligo-nsp4 1 (SEQ ID NO:6) and oligo-nsp4 3 (SEQ ID NO:8) or oligo-nsp4 2 (SEQ ID NO:7) and oligo-nsp4 4 (SEQ ID NO:9).

Both PCR products were gel-purified and then used in assembly PCR to amplify the whole nsP4 gene. For the assembly PCR, 50 pmol of the outer primers (3 and 4) and about 10 ng of each PCR fragment was used. The reaction volume was 100 μl, containing 4 units of Taq or Pwo polymerase, 0.1 mM dNTPs and 1.5 mM MgSO4. The PCR conditions were as followed:

Ninety-five ° C. for 2 minutes, followed by 5 cycles of 92° C. (45 seconds), 58° C. (30 seconds), 72° C. (120 seconds) and followed by 25 cycles of 92° C. (45 seconds), 64° C. (30 seconds), 72° C. (120 seconds).

The obtained PCR fragment was purified as described above and the eluate was digested with 20 units of SpeI and HpaI in an appropriate buffer. The fragment was gel-purified and ligated into gel-purified SpeI/HpaI restricted SinRep5 vector. The correct sequence of the obtained vector was checked by DNA sequencing.

Over night digestion of SinRep5-nsP4mut and SinRep5-nsp2mut with SpeI/HpaI and gel purification of the nsp4 fragment and sinRep-nsp2mut vector. The nsp4mut fragment was ligated into the SinRep5-nsp2mut vector. The final step was cloning the nsp gene into the 987/SinRep5 vector (Bredenbeek, P. et al., J. Virol. 67:6439–6446 (1993)) using ClaI and HpaI as restriction endonucleases, the resulting vector was named pCYTts (FIG. 2 and FIG. 3A-3D (SEQ ID NO:1)).

pCYTts constructs: Five different genes were cloned into the pCYTts vector. Green fluorescent protein (GFP), secreted alkaline phosphatase (SEAP), β-interferon (β-INF), erythropoietin (EPO), and HIV gp160.

Example 2

Regulated Expression of GFP in Transient and Stable Expression

The pCYTts system was successfully used to express cytoplasmic proteins, as an example we used the green fluorescent protein (GFP) of the jellyfish *Aequorea Victoria* (Crameri et al., *Nat. Biotech.* 14:315–319 (1996)). GFP is ligated into pCYTts via XbaI and Bsp120 I (Fermentas). Clones with the correct insert were identified by restriction digest. The GFP expression was tested in both, transient and stable expression.

Transient transfection in BHK 21 cells was carried out using the $CaPO_4$ precipitation transfection protocol: 6 µg of plasmid DNA (pCYTts GFP) in 30 µl $H_2O$ was mixed with 30 µl of an 1 M $CaCl_2$ solution. After addition of 60 µl phosphate buffer (50 mM HEPES, 280 mM NaCl, 1.5 mM $Na_2HPO_4$, pH 7.05) the solution was vortexed for 5 seconds, followed by an incubation at room temperature for 25 seconds. The solution was immediately added to 2 ml HP-1 medium containing 2% FCS (2% FCS medium). The medium of a 80% confluent BHK21 cell culture in a 6-well plate was then replaced by the DNA containing medium. After an incubation for 5 hours at 37° C. in a $CO_2$ incubator, the DNA containing medium was replaced by 2 ml of 15% glycerol in 2% FCS medium. The glycerol containing medium was removed after a 30 second incubation phase and the cells were washed with 5 ml of HP-1 medium containing 10% FCS. Finally 2 ml of fresh HP-1 medium containing 10% FCS was added.

After transient transfection of BHK cells with pCYTtsGFP, the expression was tested at 37° C. No expression of GFP was detected using the methods described below. GFP was produced when the temperature was shifted down to 29° C. The GFP expressing cells survived for at least 5 days.

Stable transfection in BHK21 cells. The stable transfection is carried out essentially as described for the transient transfection, except, for the stable transfection linearized plasmid DNA was used. Twenty µg of pCYTtsGFP was incubated with 30 units of NaeI in an appropriate buffer for at least 4 hours at 37° C. The reaction was stopped by phenol/chloroform extraction, followed by an isopropanol precipitation of the linearized DNA. The restriction reaction was checked by gel electrophoresis using a 0.8% agarose gel, stained with ethidium bromide. For the transfection 5.4 µg of linearized pCYTtsGFP was mixed with 0.6 µg of circular pSVtrpB (selection plasmid) in 30 µl $H_2O$. Followed by the procedure described for transient transfection.

Stably transfected cells were selected and grown in selection medium (HP 1 medium, without tryptophane, supplemented with 300 µM indole and 5% dialyzed FCS) at 37° C. in a $CO_2$ incubator. When the mixed population had grown to confluency, the culture was divided into two parts and both parts were cultured for an additional 12 hours at 37° C. One part of the cells was then shifted to 30° C. to induce the expression of the gene of interest. The other part was kept at 37° C.

Detection of Gene Expression

Green fluorescent protein can be easily detected in a spectrofluorometer, due to its strong fluorescence. This is seen when GFP is located in the cytoplasm of the cell. GFP production was detected by fluorescence microscopy and quantified by whole cell spectrofluorophotometry (Spectrofluorophotometer, Shimadzu RF-5001PC). Detached cells were washed with 5 ml PBS (per liter: 0.132 g $CaCl_2.2H_2O$; 0.20 g KCl; 0.20 g $KH_2PO_4$; 0.10 g $MgCl_2.6H_2O$; 8 g NaCl; 1.15 g $Na_2HPO_4$; pH 7.2) and resuspended in 1 ml PBS. The excitation wavelength was 397 nm and the emission wavelength was 510 µm. To carry out the measurements in a linear range for fluorescence detection, the cells were diluted to obtain a fluorescence between 0.05 and 1.0 emission units.

To determine the optimal induction temperature, cultures of mixed populations of stable transfected cells were incubated for 48 hours at different temperatures in selection medium without FCS. Expression was induced when cultures were shifted to 34° C. or lower. The highest expression was detected at 29° C. (FIG. 4A). When stable transfected cells were induced at 30° C. for 4 hours and subsequently grown at 37° C. for 24 hours, green cells could be observed by fluorescence microscopy. This clearly showed that the expression of the gene of interest starts after 4 hours of induction (FIG. 6A).

Time Dependence

The kinetics of the system were determined photometrically at different time points after induction. GFP expression was detected as described above. Ten hours after induction a clear expression of GFP is detectable at 29° C. (FIG. 5A). When shifting the cells back to 37° C. after induction, new mRNA production should be blocked, however, the translation of the protein of interest should occur with a higher expression level. The cells were shifted after 4, 6, 8 or 10 hours after induction back to 37° C., 24 hours later the expression of GFP was detected as described above (FIG. 6A). Thus, transcription starts shortly after induction.

Long Term Stability of the Cell Line

To determine the long term expression of the gene of interest, stably transfected cells were cultured for at least 8 weeks at 37° C. The expression of GFP was tested by shifting the cells to 29° C. No difference was observed in the expression level of GFP between cells used directly after stable transfection and cells cultured for at least 4 weeks.

Example 3

Regulated Expression of SEAP in Transient and Stable Expression

The pCYTts system was successfully used to express secreted proteins, as an example we used the secreted alkaline phosphatase (SEAP) of human origin (CLONTECH Laboratories, Inc., 1020 East Meadow Circle, Palo Alto, Calif., 94303, USA). The SEAP coding sequence is ligated into pCYTts via XbaI and StuI. Clones with the correct insert were identified by restriction digest. SEAP expression was tested for both transient and stable expression.

Transient transfection in BHK21 cells was carried out using the $CaPO_4$ co-precipitation transfection protocol as described in Example 2.

Stable Transfection in BHK21 Cells

The stable transfection was carried out essentially as described for transient transfection, except that linearized plasmid DNA was used. Twenty µg of pCYTtsSEAP was incubated with 30 units of MluI in an appropriate buffer for at least 4 hours at 37° C. 10 µg of pSVneo was digested with 30 units of ScaI for at least 4 hours at 37° C. Both reactions were stopped by phenol/chloroform extraction, followed by an isopropanol precipitation of the linearized DNA. The restriction reactions were checked by gel electrophoresis using a 0.8% agarose gel, stained with ethidium bromide. For the transfection 5.88 µg of linearized pCYTtsSEAP is mixed with 0.12 µg of linearized pSVneo (selection plasmid) in 30 µl $H_2O$. Followed by the procedure described for the transient transfection.

Detection of Gene Expression

Transient and stable transfected cells containing pCYTts-SEAP were tested for SEAP expression after 3 days of induction by dot blotting. 2.5 µl of cell culture supernatant was spotted on a nitrocellulose membrane. After drying the membrane for 10 minutes at room temperature, the development reaction was carried out using alkaline phosphatase detection reagents (10 ml AP buffer (100 mM Tris/HCl, 100 mM NaCl, pH 9.5) with 50 µl NBT solution (7.7% Nitro Blue Tetrazolium (Sigma) in 70% dimethylformamide) and 37 µl of X-Phosphate solution (5% of 5-bromo-4-chloro-3-indolyl phosphate in dimethylformamide).

The SEAP activity was quantified in an colorimetric enzymatic activity test. 500 µl of culture supernatant containing SEAP was incubated at 65° C. for 5 minutes, and finally centrifuged (20,000 g; 20 seconds). To determine the SEAP activity 400 µl of the centrifuged supernatant were mixed with 500 µl of 2×SEAP buffer (20 mM L-homoarginine, 2 M diethanolamine, and 1 mM $MgCl_2.6H_2O$, pH 9.8) in a cuvette. The SEAP activity was followed in a spectrophotometer at 405 nm, after adding 100 µl nitrophenylphosphate (120 mM) (Sigma 104, Sigma) to the sample. The absorbance was measured every 30 second over a time period of 10 minutes. The obtained values at different time points were plotted versus the time and a plot with a linear slope was obtained.

In the mixed population the amount of SEAP molecules produced per cell was estimated to be around $10^7$ molecules per cell. To get a stable expression of SEAP, cloned cells were automatically sorted in a cell sorter and finally analyzed for SEAP activity. About one out of 20 clones showed SEAP expression. The SEAP expression was estimated to be one order of magnitude higher than in the mixed population.

Highest SEAP expression was detected at 29° C. (FIG. 4B). SEAP activity could be detected 15 hours after induction at 29° C. (FIG. 5B). However, expression of SEAP started much earlier, as shown in FIG. 6B. The SEAP expressing cells were shifted after 4, 6, 8 or 10 hours of induction back to 37° C., 24 hours later the expression of SEAP was detected as described above. SEAP expression could be detected as early as 6 hours after induction (FIG. 6B). Thus the SEAP expression also started shortly after induction.

Example 4

Regulated Expression of β-INF in Transient and Stable Expression

A β-interferon gene of human origin was used to demonstrate that the pCYTts system can be used to express antiviral, secreted proteins. β-interferon has antiviral activity and interferes with RNA replication. pCYTts systems tightly regulate the expression of genes even when these genes encode proteins which interfere with RNA replication.

The gene encoding β-interferon was generated as described in Prodromou, C. and Pearl, L. (*Protein Eng.* 5:827–829 (1992)). Primers were generated using the human β-interferon nucleotide sequences disclosed in GenBank reports V00534, J00218, K00616, and M11029. The β-interferon cDNA was ligated into pCYTts after restriction with XbaI and Bsp120I. Expression of β-interferon was tested in transient and stable expression systems.

Transient and stable (mixed population) expression of β-INF was determined by Western-blotting. 0.5 ml of culture medium was methanol/chloroform precipitated and the pellet was resuspended in SDS-PAGE sample buffer. Samples were heated for 5 minutes at 95° C. before being applied to 15% acrylamide gels. After SDS-PAGE, proteins were transferred to Protan nitrocellulose membranes (Schleicher & Schuell, Inc., 10 Optical Ave., Keene, N.H. 03431, USA). The membrane was blocked with 1% bovine albumin (Sigma) in TBS (10×TBS per liter: 87.7 g NaCl, 66.1 g Trizma hydrochloride (Sigma) and 9.7 g Trizma base (Sigma), pH 7.4) for 1 hour at room temperature, followed by an incubation with a mouse anti-human β-INF antibody (0.2 µg/ml, Research Diagnostics Inc., USA) for 1 hour. The blot was washed 3 times for 10 minutes with TBS containing 0.05% Tween20 (TBS-T), and incubated for 1 hour with a horseradish peroxidase-anti-mouse IgG conjugate (0.1 µg/ml, Amersham Life Science, England). After washing 2 times for 10 minutes with TBS-T and 2 times for 10 minutes with TBS, the development was carried using the ECL kit (Amersham).

Samples for the blot were taken after 3 or 5 days incubation at 29° C. Another part of the culture was kept at 37° C. and a sample was taken after 5 days. FIG. 8A shows that β-INF is produced after 3 days at 29° C. whereas incubation at 37° C. yields no detectable β-INF production.

Example 5

Regulated Expression of EPO in Transient Expression

The pCYTts system was successfully used to express pharmaceutically relevant, secreted proteins. As an example of such expression, we used a gene of human origin encoding erythropoietin (EPO). This gene was generated by PCR as described in Example 4. Primers were generated using the human EPO nucleotide sequences disclosed in GenBank report X02158. The gene encoding EPO was ligated into pCYTts following restriction with XbaI and Bsp120L (Fermentas). Clones with the correct insert were identified by restriction digest. EPO expression was tested in both transient and stable expression systems.

BHK21 cells were transiently transfected according to the $CaPO_4$ co-precipitation protocol, as described in Example 2.

EPO production was determined by western blotting, as described in Example 4. The detection was carried out by incubating the nitrocellulose membrane with 2 µg rabbit anti-human EPO antibody (Research Diagnostics Inc.) in 10 ml TBS-T for 1 hour, followed by 3 washes, each for 10 minutes, with TBS-T. Finally, the nitrocellulose membrane was incubated for 1 hour with alkaline phosphatase conjugated anti-rabbit IgG (Jackson ImmunoResearch Laboratories, Inc.) diluted 1:5000 in TBS-T. After washing 2 times for 10 minutes with TBS-T and 2 times for 10 minutes with TBS, the blot was developed by alkaline phosphatase staining as described in Example 3. Transiently transfected cells induced for 4 days at 29° C. produced detectable amounts of EPO (FIG. 8B).

Example 6

Regulated Expression of EPO in Stable Expression

In the pCYTts504EPO expression vector, the human erythropoietin (EPO) coding sequence (including its natural leader peptide for secretion into the growth medium) was fused in frame to the sequence coding for the Sindbis virus capsid protein (C-protein). The rationale of this construct was to include the translational enhancer located within the C-protein coding region that has been shown to lead to a 10- to 20-fold increased expression level compared to constructs lacking this enhancer (Frolov et al., *Proc. Natl. Acad. Sci. USA* 93:11371–11377 (1996)). The fusion gene is expressed from the subgenomic promoter of expression vector pCYTts. Upon co-translational release of the EPO precursor from the fusion protein, catalyzed by the autoproteolytic activity of the C-protein, EPO is directed to the secretory pathway by its N-terminal leader peptide.

For stable transfection, a 3:1 ratio of pCYTts504EPO (linearized by restriction cleavage with MluI) and the neomycin resistance-conferring plasmid 987BBneo (Bredenbeek et al., J. Virol. 67:6439–6446 (1993) (linearized by restriction cleavage with ScaI) were introduced into BHK21 cells using the calcium phosphate co-precipitation protocol described in Example 2. After 1 week incubation at 37° C. under selective conditions (HP-I medium supplemented with 10% FCS and 200 µg/ml G418 (neomycin)), single colonies were separated and further propagated under the same conditions.

To screen for EPO-secreting clones, cells were grown in 12-well plates at 37° C. to 80% confluency and incubated at 30° C. for further 4 days. Three µl of each culture supernatant were analyzed for secreted EPO by Dot Blot analysis using an anti-EPO rabbit IgG and an anti rabbit IgG-alkaline phosphatase conjugate. Among 27 clones investigated, one EPO-secreting clone was identified. A rough concentration of 2.5 mg EPO per liter of supernatant was estimated using an EPO ELISA Kit (Boehringer Mannheim). The identity of the secreted protein was further confirmed by Western Blot analysis. For that purpose, cells were grown to 80% confluency at 37° C. in a T-75 cell culture flask with 30 µl HP-1 medium (without FCS) supplemented with G418 (200 µg/ml) and then incubated at 30° C. for further 4 days. Twenty µl of the culture supernatant were separated on a 15% SDS polyacrylamide gel and blotted onto a nitrocellulose membrane. Using an anti-EPO rabbit IgG/anti-rabbit IgG-alkaline phosphatase conjugate system, a single protein was specifically detected, that showed the same electrophoretic mobility as an authentic EPO sample from a different source (apparent $M_r$ about 29 kDa) (FIG. 9). The resulting cell line was named 1C4.

Example 7

Production of Sindbis Virus Particles Containing EPO RNA

One µg of RNase-free vector (pDH-EB; Bredenbeek et al., J. Virol. 11:6439–6446 (1993)) was linearized by EcoRI digestion. Subsequently in vitro transcription was carried out using the SP6 in vitro transcription kit (InvitroscripCAP by Invitrogen, Invitrogen BV, NV Leek, Netherlands). The resulting 5'-capped mRNA was analyzed on reducing agarose-gels.

Five µg of in vitro transcribed mRNA were electroporated into 1C4 cell line (Example 6) according to Invitrogen's manual (Sindbis Expression system, Invitrogen BV, Netherlands). After 10 hours incubation at 37° C. the FCS containing medium was exchanged by HP-1 medium without FCS, followed by an additional incubation at 30° C. for 72 hours. The supernatant was passaged to a BHK 21 cell layer, incubated for 2 hours at 4° C. and finally discharged. The cells were washed 4 times with HP-1 buffer and incubated for 24 hours at 30° C. Three µl of the culture supernatant were analyzed for secreted EPO by Dot Blot analysis using an anti-EPO rabbit IgG and an anti rabbit IgG-alkaline phosphatase conjugate (FIG. 10).

Example 8

Regulated Expression of gp160 in Transient Expression

The pCYTts system was used to express gp160, the HIV envelope protein. The gp160 gene was amplified from pAbT4674 (ATCC 40829) and cloned in pCYTts via XbaI and Bsp120L. BHK21 cells were transiently transfected using lipofectamine (Life Technologies, Basel, Switzerland). 0.8 µg pCYTts gp160 DNA in 150 µl Dulbecco's Modified Eagle medium (DMEM, Life Technologies, Basel, Switzerland) was mixed with 150 µl DMEM containing 2.5 µl lipofectamine. The solution was incubated at room temperature for 15 minutes and added to a 80% confluent BHK cell layer in a 24-well plate. After incubation for 5 hours at 37° C. in a $CO_2$ incubator, the cells were washed and incubated for another 12 hours at 37° C. Cells were split and one part was incubated at 29° C. and one part was incubated at 37° C. for 5 days. Cells were harvested and lysed in SDS-PAGE sample buffer. Samples were heated for 5 minutes at 95° C. and applied to a 8% acrylamide gel. gp160 expression was analyzed by Western blotting as described in Example 4. The nitrocellulose membrane was incubated with rabbit anti-human gp160 antibody (kindly provided by Dr. Schawaller, Diamed AG, Switzerland), diluted 1:3000 in 10 ml TBS-T for 1 hour and subsequently washed three times for 10 minutes with TBS-T. Then the membrane was incubated for 1 hour with alkaline phosphatase conjugated goat anti-rabbit IgG (Jackson ImmunoResearch Laboratories, Inc.) diluted 1:5000 in 10 ml TBS-T. The membrane was washed two times with TBS-T for 10 minutes and two times for 10 minutes with TBS. Development was carried out as described in Example 3. Transiently transfected cells produced detectable amounts of gp160 (data not shown).

Example 9

Regulated Expression of GFP in Human Foreskin Fibroblasts

The pCYTts system was used to express green fluorescent protein in human foreskin fibroblasts. Cells were transfected using lipofectamine as described in Example 8. Twelve hours post-transfection one part of the cells was incubated at 37° C., the other part was incubated at 29° C. After 48 hours bright green cells were observed by fluorescence microscopy in the cultures incubated at 29° C., whereas at 37° C. no GFP expression was detected.

Example 10

A Multivector System with the Insert in Sense Direction

The regulatable vector system of the invention was used for the production of non-cytopathic viral particles. As the gene of interest we chose the structural proteins of Sindbis virus and as a marker protein we chose GFP. The cells were stably transfected with pCYTtsGFP, as described in Example 2. The stable transfected cells were transiently transfected with a defective helper construct (PDHBB; Bredenbeek et al., J. Virol. 11:6439–6446 (1993)), carrying the Sindbis virus structural proteins according to the protocol described in Example 2.

Transfected cells were grown overnight at 37° C. The cells were then shifted to 29° C. to induce viral gene expression. The viral particles formed contain packaged pCYTtsGFP RNA sequences, and GFP is expressed when the packaged viral particles infect new target cells. To perform the new infection, the medium was collected and centrifuged (1800 rpm; 3 minutes) after 4 days of expression. The supernatant was placed on 80% confluent BHK cell layers and incubated for 4 hours at 29° C. After the incubation phase the medium was discharged and the cells were washed 3 times with 5 ml HP-1 medium followed by incubation at 29° C. for an additional 24 hours. Finally, the expression level of the marker gene GFP was measured by fluorescence spectroscopy, as described in Example 2.

About 10% of the BHK cells initially produced GFP and after an additional 24 hours of incubation at 29° C. all cells of the expressed GFP. The conditioned medium of these cells was again harvested, centrifuged and placed onto a 80% confluent layer of BHK cells. After 48 hours of incubation at 29° C., 100% of these cells were found to express GFP.

As a control, the transfected cells were grown for 5 days at 37° C. after which conditioned medium was collected and centrifuged (1800 rpm, 3 minutes). The supernatant was placed onto an 80% confluent BHK cell layer. After 8 hours of incubation at 29 ° C., the medium removed and the cells were washed 3 times with 5 ml HP-1 medium and incubated at 29° C. for additional 24 hours. Finally, the expression level of GFP is determined. No GFP expressing cells could be detected (FIGS. 7A and 7B).

Example 11

A Multivector System with Insert in Antisense Direction

As a model system we tested the regulatable system with the production of viral particles. As the gene of interest we choose the structural proteins of Sindbis virus and as a marker protein we chose GFP. The cells were stably transfected with pCYTtsGFP, as described in Example 2.

The antisense helper vector was constructed as follows:

The structural proteins were obtained by digesting the pDHBB vector (Bredenbeek, P. et al., *J. Virol.* 67:6439–6446 (1993)) with EcoRI and BamHI. The fragment was purified by gel electrophoresis and cloned into EcoRI/BamHI digested pMPSVHE vector (Artelt, P. et al., *Gene* 68:213–219 (1988)). Since the EcoRI and BamHI restriction sites are in opposite orientations in these vectors, the structural protein fragment was cloned in an antisense orientation into pMPSVHE. The resulting vector was named pMPSV anti-DHBB.

The stable transfected cells were transiently transfected with pMPSV anti-DHBB as described in Example 10. Transfected cells were grown overnight at 37° C. The cells were then shifted to 29° C. to induce viral gene expression. After 4 days of induction, the conditioned medium was collected and centrifuged (1800 rpm; 3 minutes). The supernatant was placed on 80% confluent BHK cell layers and was incubated for 4 hours at 29° C. After the incubation phase the medium was discharged and the cells were washed 3 times with 5 ml HP-1 medium and incubated at 29° C. for additional 24 hours. Finally, the expression level of the marker gene GFP was measured by fluorescence spectroscopy, as described in Example 2.

About 1% of the BHK cells initially produced GFP and after an additional 120 hours incubation at 29° C. 30% of the cells express GFP. Thus, even antisense DNA fragments can be used within this invention to produce functional proteins.
Conclusions The expression system described in the preceding examples fulfills nearly all of the criteria for an ideal inducible gene expression system as described in Saez, E. et al., (*Curr. Opin. Biotechnol.* 8:608–616 (1997)). This system is very specific in that it is only switched on when the temperature is shifted to below 34° C. The basal expression, as shown in several experiments, is not detectable with the standard detection methods used in the preceding examples. Even with the very sensitive system of viral infection (FIG. 7A-7B and FIG. 9) no basal expression at 37° C. could be detected. This shows the high degree of regulatory stringency, because a functional replicase molecule would initiate an autocatalytic cycle of RNA replication and transcription which would result in a high expression level of the protein of interest.

Further, as shown in FIG. 6A-6B, gene expression starts rapidly after induction and stops quickly after the temperature is shifted back to a restrictive one. There is no problem with the bioavailability of the inducer, because temperature shifts to 29° C. rapidly disseminate and are non-toxic. Once a restrictive temperature has been reached, the duration of gene expression is only dependent on the stability of the mRNA encoding the protein or RNA of interest.

Compared with the tetracycline system, the system described in the preceding examples has the advantages that there is no detectable basal expression and the bioavailability of a temperature shift is much less harmful than the antibiotic tetracycline or the expression of the tTA protein. A further advantage of the herein described regulatable DNA vector system is that only one vector need be introduced into a host cell, because all relevant proteins needed for the expression and regulation can be encoded by this one vector. This is in contrast with the tetracycline system where two vectors must be transfected into the cells (Gossen, M. & Bujard, H., *Proc. Natl. Acad. Sci. USA* 89:5547–5551 ((1992)).

As already noted, the turning off of the pCYTts system is dependent on the stability of the replicase and the mRNA encoding the protein of interest. It has been shown that the half-life of the replicase is one half hour after expression (De Groot et al., *Proc. Natl. Acad. Sci. USA* 88:8967–8971 (1991)). The mRNA stability is therefore the limiting factor which determines how rapidly the system is switched off. SEAP mRNA, for example, was translated for about 10 hours after shifting to restrictive temperature (FIG. 6A-6B). This high stability has also been found for CAT mRNA (Xiong, C. et al., *Science* 243:1188–1191 (1989)), suggesting that mRNA derived from the Sindbis virus is very stable regardless of the protein encoded by this mRNA.

The system was tested in mixed population to prove that the expression system is independent of the site of integration and the copy number, as shown in FIG. 4A-4B and FIG. 5A-5B.

In conclusion, the pCYTts temperature regulatable gene expression system described in the preceding examples has significant advantages over the commonly used regulatable systems. Due to its very low level of basal expression, this system can be used for the expression of host toxic proteins, as shown with the expression of the HIV envelope protein gp160, which so far has been a difficult task with previous in vitro gene expression systems. Since the present system has also tested for the long term expression and the reinducibility, it is useful for gene therapy. Its potential use for gene therapy has been shown in the transient expression of GFP in human skin cells, which are easy accessible for temperature regulation.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A DNA molecule which encodes an RNA molecule comprising:
   (a) at least one cis-acting sequence element,
   (b) a first open reading frame which encodes a non-cytopathic temperature-sensitive Sindbis virus replicase, wherein the non-cytopathicity is conferred by a substitution of proline at position 726 of the non-structural protein 2 (nsP2) of the replicase with another naturally occurring amino acid, and
   (c) at least one nucleotide sequence selected from the group consisting of:
      (i) a second open reading frame encoding a protein, or portion thereof, wherein said second open reading frame is in a translatable format after one or more RNA-dependent RNA replication events;
      (ii) a sequence complementary to all or part of the second open reading frame of (i); and
      (iii) a sequence encoding an untranslated RNA molecule, or complement thereof;
   wherein said at least one nucleotide sequence of (c) is operably linked to a promoter which is recognized by said non-cytopathic, temperature-sensitive Sindbis virus replicase.

2. The DNA molecule of claim 1, which comprises only one nucleotide sequence of (c).

3. The DNA molecule of claim 1, wherein said second open reading frame is in a translatable format after one RNA-dependent RNA replication event.

4. The DNA molecule of claim 1, wherein said second open reading frame is in a translatable format after three RNA-dependent RNA replication events.

5. The DNA molecule of claim 1 which encodes an alphaviral replicase having replicase activity at 34° C. which is at least five fold lower than the replicase activity exhibited at 29° C.

6. The DNA molecule of claim 1, wherein the second open reading frame encodes a cytokine, a lymphokine, a tumor necrosis factor, an interferon, a toxic protein, or a prodrug converting enzyme.

7. The DNA molecule of claim 1, wherein the second open reading frame encodes human erythropoietin or human β-interferon.

8. A method of making a recombinant host cell comprising introducing the DNA molecule of claim 1 into a host cell in vitro.

9. An in vitro cell culture comprising a recombinant host cell comprising at least one DNA molecule of claim 1.

10. The cell culture of claim 9, wherein at least one of said DNA molecules is stably maintained in said host cell.

11. An RNA molecule comprising:
   (a) at least one cis-acting sequence element,
   (b) a first open reading frame which encodes a non-cytopathic temperature-sensitive Sindbis virus replicase, wherein the non-cytopathicity is conferred by a substitution of proline at position 726 of the non-structural protein 2 (nsP2) of the replicase with another naturally occurring amino acid, and
   (c) at least one nucleotide sequence selected from the group consisting of:
      (i) a second open reading frame encoding a protein, or portion thereof, wherein said second open reading frame is in a translatable format after one or more RNA-dependent RNA replication events;
      (ii) a sequence complementary to all or part of the second open reading frame of (i); and
      (iii) a sequence encoding an untranslated RNA molecule, or complement thereof;
   wherein said at least one nucleotide sequence of (c) is operably linked to a promoter which is recognized by said non-cytopathic, temperature-sensitive Sindbis virus replicase.

12. An alphaviral particle containing the RNA molecule of claim 11.

13. An in vitro cell culture comprising a recombinant host cell comprising the RNA molecule of claim 11.

14. A method for producing a protein or an untranslated RNA molecule in a recombinant host cell comprising:
   (a) introducing at least one DNA molecule of claim 1 into said host cells in vitro;
   (b) culturing said host cells under conditions suitable for expression of said protein or untranslated RNA molecule; and
   (c) recovering said protein or untranslated RNA molecule;
   wherein said protein or untranslated RNA molecule is encoded by said DNA molecule.

15. A method for producing a protein or an untranslated RNA molecule in a recombinant host cell comprising:
   (a) introducing at least one RNA molecule of claim 11 into said host cells in vitro;
   (b) culturing said host cells under conditions suitable for expression of said protein or untranslated RNA molecule; and
   (c) recovering said protein or untranslated RNA molecule;
   wherein said protein or untranslated RNA molecule is encoded by said RNA molecule.

16. The method of claim 15, wherein the protein is erythropoietin.

17. A method for producing alphaviral particles, said method comprising:

(a) introducing into a host cell in vitro at least one DNA molecule of claim 1 having one or more open reading frames which encode alphaviral structural proteins;

(b) growing host cells under culture conditions suitable for the production of alphaviral particles which contain an RNA transcription product of said DNA molecule; and (c) recovering said alphaviral particles.

18. A method for producing a protein encoded by RNA contained in an alphaviral particle produced by the method of claim 17 in a recombinant host cell comprising:

(a) infecting a host cell in vitro with the alphaviral particle;

(b) growing said host cell under culture conditions suitable for the production of said protein; and (c) recovering said protein.

19. The method of claim 18, wherein said protein is erythropoietin.

20. A method for regulating the expression of a protein or an untranslated RNA molecule in a recombinant host cell comprising:

(a) introducing at least one DNA molecule of claim 1 into said host cells in vitro;

(b) growing host cells under suitable culture conditions; and (c) changing the temperature of the host cell culture from:

(i) a permissive temperature to a restrictive temperature, or (ii) a restrictive temperature to a permissive temperature;

wherein said protein or untranslated RNA molecule is encoded by said DNA molecule.

21. A method for regulating the expression of a protein or an untranslated RNA molecule in a recombinant host cell comprising:

(a) introducing at least one RNA molecule of claim 11 into host cells in vitro;

(b) growing said host cells under suitable culture conditions; and (c) changing the temperature of the host cell culture from:

(i) a permissive temperature to a restrictive temperature, or (ii) a restrictive temperature to a permissive temperature;

wherein said protein or untranslated RNA molecule is encoded by said at least one RNA molecule of claim 11.

22. An isolated nucleic acid molecule comprising a polynucleotide having the nucleotide sequence of SEQ ID NO:1.

23. A DNA vector system comprising one or more polynucleotides which encode RNA molecules, said RNA molecules comprising:

(a) at least one cis-acting sequence element, (b) a first open reading frame having a nucleotide sequence encoding a non-cytopathic, temperature-sensitive Sindbis virus replicase, wherein the non-cytopathicity is conferred by a substitution of proline at position 726 of the nonstructural protein 2 (nsP2) of the replicase with another naturally occurring amino acid, and (c) at least one nucleotide sequence selected from the group consisting of:

(i) a second open reading frame encoding a protein, or portion thereof, wherein said second open reading frame is in a translatable format after one or more RNA-dependent RNA replication events;

(ii) a sequence complementary to all or part of the second open reading frame of (i); and (iii) a sequence encoding an untranslated RNA molecule, or complement thereof;

wherein said at least one nucleotide sequence of (c) is operably linked to a promoter which is recognized by said non-cytopathic, temperature-sensitive Sindbis virus replicase.

24. The DNA vector system of claim 23 which encodes an alphaviral replicase having replicase activity at 34° C. which is at least five fold lower than the replicase activity exhibited at 29° C.

25. The DNA vector system of claim 23, wherein the second open reading frame encodes a cytokine, a lymphokine, a tumor necrosis factor, an interferon, a toxic protein, or a prodrug converting enzyme.

26. The DNA vector system of claim 23, wherein the second open reading frame encodes human erythropoietin or human β-interferon.

27. A method of making a recombinant host cell comprising introducing at least one DNA vector system of claim 23 into a host cell in vitro.

28. An in vitro cell culture comprising a recombinant host cell comprising at least one DNA vector system of claim 23.

29. The cell culture of claim 28, wherein some or all of the polynucleotide sequences of claim 23 are stably maintained in said host cell.

30. A method for producing a protein or an untranslated RNA molecule in a recombinant host cell comprising:

(a) introducing at least one DNA vector system of claim 23 into host cells in vitro;

(b) growing said host cells under suitable culture conditions; and (c) recovering said protein or untranslated RNA molecule;

wherein said protein or untranslated RNA molecule is encoded by said at least one nucleotide sequence.

31. The method of claim 30, wherein said protein is erythropoietin.

32. A method for producing an alphaviral particle comprising an RNA encoding a non-cytopathic, temperature-sensitive Sindbis virus replicase, the method comprising:

(a) introducing at least one DNA vector system of claim 23 into host cells in vitro;

(b) growing said host cells under suitable culture conditions;

(c) producing an alphaviral particle comprising an RNA encoding a non-cytopathic, temperature-sensitive Sindbis virus replicase; and (d) recovering said alphaviral particle.

33. A method for producing a protein in a recombinant host cell comprising:

(a) infecting host cells in vitro with an alphaviral particle produced by the method of claim 32, wherein said alphaviral particle comprises an RNA encoding said non-cytopathic, temperature sensitive Sindbis virus replicase;

(b) growing said host cells under suitable culture conditions; and (c) recovering said protein;

wherein said protein is encoded by nucleic acid contained in said alphaviral particle.

34. The method of claim 33, wherein said protein is erythropoietin.

35. A method for regulating the expression of a protein or an untranslated RNA molecule in a recombinant host cell comprising:

(a) introducing at least one DNA vector system of claim 23 into host cells in vitro;

(b) growing said host cells under suitable culture conditions; and (c) changing the temperature of the host cell culture from:
  (i) a permissive temperature to a restrictive temperature, or
  (ii) a restrictive temperature to a permissive temperature;

wherein said protein or untranslated RNA molecule is encoded by the polynucleotides of said at least one DNA vector system.

36. A composition comprising one or more RNA molecules, said RNA molecules comprising:

(a) at least one cis-acting sequence element, (b) a first open reading frame having a nucleotide sequence encoding a non-cytopathic, temperature-sensitive Sindbis virus replicase, wherein the non-cytopathicity is conferred by a substitution of proline at position 726 of the nonstructural protein 2 (nsP2) of the replicase with another naturally occurring amino acid, and (c) at least one nucleotide sequence selected from the group consisting of:
  (i) a second open reading frame encoding a protein, or portion thereof, wherein said second open reading frame is in a translatable format after one or more RNA-dependent RNA replication events;
  (ii) a sequence complementary to all or part of the second open reading frame of (i); and
  (iii) a sequence encoding an untranslated RNA molecule, or complement thereof;

wherein said at least one nucleotide sequence of (c) is operably linked to a promoter which is activated by said non-cytopathic, temperature-sensitive Sindbis virus replicase.

37. The DNA molecule of claim 1, wherein the non-cytopathicity is conferred by a substitution of proline at position 726 of the nsP2 with serine.

38. The DNA molecule of claim 1, wherein temperature sensitivity is conferred by one or more mutations in the nsP4 gene of said replicase.

39. The DNA molecule of claim 1, wherein the non-cytopathicity is conferred by a substitution of proline at position 726 of the nsP2 with serine, and temperature sensitivity is conferred by one or more mutations in the nsP4 gene of said replicase.

40. The DNA vector system of claim 23, wherein the non-cytopathicity is conferred by a substitution of proline at position 726 of the nsP2 with serine.

41. The DNA vector system of claim 23, wherein temperature sensitivity is conferred by one or more mutations in the nsP4 gene of said replicase.

42. The DNA vector system of claim 23, wherein the non-cytopathicity is conferred by a substitution of proline at position 726 of the nsP2 with serine, and temperature sensitivity is conferred by one or more mutations in the nsP4 gene of said replicase.

43. The composition of claim 36, wherein the non-cytopathicity is conferred by a substitution of proline at position 726 of the nsP2 with serine.

44. The composition of claim 36, wherein temperature sensitivity is conferred by one or more mutations in the nsP4 gene of said replicase.

45. The composition of claim 36, wherein the non-cytopathicity is conferred by a substitution of proline at position 726 of the nsP2 with serine, and temperature sensitivity is conferred by one or more mutations in the nsP4 gene of said replicase.

46. A method for producing a protein or an untranslated RNA molecule in a recombinant host cell comprising:

(a) introducing at least one alphaviral particle of claim 12 into said host cells in vitro;

(b) culturing said host cells under conditions suitable for expression of said protein or untranslated RNA molecule; and (c) recovering said protein or untranslated RNA molecule;

wherein said protein or untranslated RNA molecule is encoded by said RNA molecule contained within said alphaviral particle.

* * * * *

SEQUENCE LISTING

<160> NUMBER OF SEQ ID NOS: 9

<210> SEQ ID NO 1
<211> LENGTH: 11282
<212> TYPE: DNA
<213> ORGANISM: Artificial Sequence
<220> FEATURE:
<223> OTHER INFORMATION: Description of Artificial Sequence:cDNA

<400> SEQUENCE: 1

| | | | | | |
|---|---|---|---|---|---|
| ctgacgcgcc | ctgtagcggc | gcattaagcg | cggcgggtgt | ggtggttacg | cgcagcgtga | 60 |
| ccgctacact | tgccagcgcc | ctagcgcccg | ctcctttcgc | tttcttccct | tcctttctcg | 120 |
| ccacgttcgc | cggctttccc | cgtcaagctc | taaatcgggg | gctcccttta | gggttccgat | 180 |
| ttagtgcttt | acggcacctc | gaccccaaaa | aacttgatta | gggtgatggt | tcacgtagtg | 240 |
| ggccatcgcc | ctgatagacg | gttttttcgcc | ctttgacgtt | ggagtccacg | ttctttaata | 300 |
| gtggactctt | gttccaaact | ggaacaacac | tcaaccctat | ctcggtctat | tcttttgatt | 360 |
| tataagggat | tttgccgatt | tcggcctatt | ggttaaaaaa | tgagctgatt | taacaaaaat | 420 |
| ttaacgcgaa | ttttaacaaa | atattaacgc | ttacaatttc | cattcgccat | tcaggctgcg | 480 |
| caactgttgg | gaagggcgat | cggtgcgggc | ctcttcgcta | ttacgccagc | tggcgaaagg | 540 |
| gggatgtgct | gcaaggcgat | taagttgggt | aacgccaggg | ttttcccagt | cacgacgttg | 600 |
| taaaacgacg | gccagtgagc | gcgcaattaa | ccctcactaa | agggaacaaa | agctggctag | 660 |
| tggatccagt | cttatgcaat | actcttgtag | tcttgcaaca | tggtaacgat | gagttagcaa | 720 |
| catgccttac | aaggagagaa | aaagcaccgt | gcatgccgat | tggtggaagt | aaggtggtac | 780 |
| gatcgtgcct | tattaggaag | gcaacagacg | ggtctgacat | ggattggacg | aaccactgaa | 840 |
| ttccgcattg | cagagatatt | gtatttaagt | gccctacctc | gataccgtcg | agattgacgg | 900 |
| cgtagtacac | actattgaat | caaacagccg | accaattgca | ctaccatcac | aatggagaag | 960 |
| ccagtagtaa | acgtagacgt | agaccccag | agtccgtttg | tcgtgcaact | gcaaaaaagc | 1020 |
| ttcccgcaat | ttgaggtagt | agcacagcag | gtcactccaa | atgaccatgc | taatgccaga | 1080 |
| gcattttcgc | atctggccag | taaactaatc | gagctggagg | ttcctaccac | agcgacgatc | 1140 |
| ttggacatag | gcagcgcacc | ggctcgtaga | atgttttccg | agcaccagta | tcattgtgtc | 1200 |
| tgccccatgc | gtagtccaga | agacccggac | cgcatgatga | aatacgccag | taaactggcg | 1260 |
| gaaaaagcgt | gcaagattac | aaacaagaac | ttgcatgaga | agattaagga | tctccggacc | 1320 |
| gtacttgata | cgccggatgc | tgaaacacca | tcgctctgct | ttcacaacga | tgttacctgc | 1380 |
| aacatgcgtg | ccgaatattc | cgtcatgcag | gacgtgtata | tcaacgctcc | cggaactatc | 1440 |
| tatcatcagg | ctatgaaagg | cgtgcggacc | ctgtactgga | ttggcttcga | caccacccag | 1500 |
| ttcatgttct | cggctatggc | aggttcgtac | cctgcgtaca | acaccaactg | ggccgacgag | 1560 |
| aaagtccttg | aagcgcgtaa | catcggactt | tgcagcacaa | agctgagtga | aggtaggaca | 1620 |
| ggaaaattgt | cgataatgag | gaagaaggag | ttgaagcccg | ggtcgcgggt | ttatttctcc | 1680 |
| gtaggatcga | cactttatcc | agaacacaga | gccagcttgc | agagctggca | tcttccatcg | 1740 |
| gtgttccact | tgaatggaaa | gcagtcgtac | acttgccgct | gtgatacagt | ggtgagttgc | 1800 |
| gaaggctacg | tagtgaagaa | aatcaccatc | agtcccggga | tcacgggaga | aaccgtggga | 1860 |
| tacgcggtta | cacacaatag | cgagggcttc | ttgctatgca | aagttactga | cacagtaaaa | 1920 |
| ggagaacggg | tatcgttccc | tgtgtgcacg | tacatcccgg | ccaccatatg | cgatcagatg | 1980 |

```
actggtataa tggccacgga tatatcacct gacgatgcac aaaaacttct ggttgggctc      2040
aaccagcgaa ttgtcattaa cggtaggact aacaggaaca ccaacaccat gcaaaattac      2100
cttctgccga tcatagcaca agggttcagc aaatgggcta aggagcgcaa ggatgatctt      2160
gataacgaga aaatgctggg tactagagaa cgcaagctta cgtatggctg cttgtgggcg      2220
tttcgcacta agaaagtaca ttcgttttat cgcccacctg aacgcagac ctgcgtaaaa       2280 gtcccagcct cttttagcgc ttttcccatg tcgtccgtat ggacgacctc tttgcccatg      2340
tcgctgaggc agaaattgaa actggcattg caaccaaaga aggaggaaaa actgctgcag      2400
gtctcggagg aattagtcat ggaggccaag gctgcttttg aggatgctca ggaggaagcc      2460
agagcggaga agctccgaga agcacttcca ccattagtgg cagacaaagg catcgaggca      2520
gccgcagaag ttgtctgcga agtggagggg ctccaggcgg acatcggagc agcattagtt      2580
gaaaccccgc gcggtcacgt aaggataata cctcaagcaa atgaccgtat gatcggacag      2640
tatatcgttg tctcgccaaa ctctgtgctg aagaatgcca aactcgcacc agcgcacccg      2700
ctagcagatc aggttaagat cataacacac tccggaagat caggaaggta cgcggtcgaa      2760
ccatacgacg ctaaagtact gatgccagca ggaggtgccg taccatggcc agaattccta      2820
gcactgagtg agagcgccac gttagtgtac aacgaaagag agtttgtgaa ccgcaaaacta     2880 taccacattg ccatgcatgg ccccgccaag aatacagaag aggagcagta caaggttaca      2940
aaggcagagc ttgcagaaac agagtacgtg ttttgacgtgg acaagaagcg ttgcgttaag    3000
aaggaagaag cctcaggtct ggtcctctcg ggagaactga ccaaccctcc ctatcatgag      3060
ctagctctgg agggactgaa gacccgacct gcggtcccgt acaaggtcga acaatagga       3120 gtgataggca caccggggtc gggcaagtca gctattatca agtcaactgt cacggcacga      3180
gatcttgtta ccagcggaaa gaaagaaaat tgtcgcgaaa ttgaggccga cgtgctaaga     3240 ctgagggta tgcagattac gtcgaagaca gtagattcgg ttatgctcaa cggatgccac       3300
aaagccgtag aagtgctgta cgttgacgaa gcgttcgcgt gccacgcagg agcactactt     3360
gccttgattg ctatcgtcag gccccgcaag aaggtagtac tatgcggaga ccccatgcaa     3420
tgcggattct tcaacatgat gcaactaaag gtacatttca atcaccctga aaaagacata     3480
tgcaccaaga cattctacaa gtatatctcc cggcgttgca cacagccagt tacagctatt     3540
gtatcgacac tgcattacga tggaaagatg aaaaccacga acccgtgcaa gaagaacatt     3600
gaaatcgata ttcaggggc cacaaagccg aagccagggg atatcatcct gacatgtttc     3660
cgcgggtggg ttaagcaatt gcaaatcgac tatcccggac atgaagtaat gacagccgcg     3720
gcctcacaag ggctaaccag aaaaggagtg tatgccgtcc ggcaaaaagt caatgaaaac     3780
ccactgtacg cgatcacatc agagcatgtg aacgtgttgc tcacccgcac tgaggacagg     3840
ctagtgtgga aaaccttgca gggcgaccca tggattaagc agcccactaa catacctaaa     3900 ggaaacttc aggctactat agaggactgg gaagctgaac acaagggaat aattgctgca     3960
ataaacagcc ccactccccg tgccaatccg ttcagctgca agaccaacgt tgctgggcg      4020 aaagcattgg aaccgatact agccacggcc ggtatcgtac ttaccggttg ccagtggagc     4080
gaactgttcc cacagtttgc ggatgacaaa ccacattcgg ccatttacgc cttagacgta     4140
atttgcatta gttttttcgg catggacttg acaagcggac tgttttctaa acagagcatc     4200
ccactaacgt accatcccgc cgattcagcg aggccggtag ctcattggga caacagccca     4260
ggaacccgca agtatgggta cgatcacgcc attgccgccg aactctcccg tagatttccg     4320
```

-continued

```
gtgttccagc tagctgggaa gggcacacaa cttgatttgc agacggggag aaccagagtt    4380
atctctgcac agcataacct ggtcccggtg aaccgcaatc ttcctcacgc cttagtcccc    4440
gagtacaagg agaagcaacc cggcccggtc aaaaaattct tgaaccagtt caaacaccac    4500
tcagtacttg tggtatcaga ggaaaaaatt gaagctcccc gtaagagaat cgaatggatc    4560
gccccgattg gcatagccgg tgcagataag aactacaacc tggctttcgg gtttccgccg    4620
caggcacggt acgacctggt gttcatcaac attggaacta atacagaaa ccaccacttt    4680
cagcagtgcg aagaccatgc ggcgacctta aaaacccttt cgcgttcggc cctgaattgt    4740
ttaaactcag gaggcaccct cgtggtgaag tcctatggct acgccgaccg caacagtgag    4800
gacgtagtca ccgctcttgc cagaaagttt gtcagggtgt ctgcagcgag accagattgt    4860
gtctcaagca atacagaaat gtacctgatt ttccgacaac tagacaacag ccgtacacgg    4920
caattcaccc cgcaccatct gaattgcgtg atttcgtccg tgtatgaggg tacaagagat    4980
ggagttggag ccgcgccgtc ataccgcacc aaaagggaga atattgctga ctgtcaagag    5040
gaagcagttg tcaacgcagc caatccgctg ggtagaccag gcgaaggagt ctgccgtgcc    5100
atctataaac gttggccgac cagttttacc gattcagcca cggagacagg caccgcaaga    5160
atgactgtgt gcctaggaaa gaaagtgatc cacgcggtcg gccctgattt ccggaagcac    5220
ccagaagcag aagccttgaa attgctacaa aacgcctacc atgcagtggc agacttagta    5280
aatgaacata acatcaagtc tgtcgccatt ccactgctat ctacaggcat ttacgcagcc    5340
ggaaaagacc gccttgaagt atcacttaac tgcttgacaa ccgcgctaga cagaactgac    5400
gcggacgtaa ccatctattg cctggataag aagtggaagg aaagaatcga cgcggcactc    5460
caacttaagg agtctgtaac agagctgaag gatgaagata tggagatcga cgatgagtta    5520
gtatggattc atccagacag ttgcttgaag ggaagaaagg gattcagtac tacaaaagga    5580
aaattgtatt cgtacttcga aggcaccaaa ttccatcaag cagcaaaaga catggcggag    5640
ataaaggtcc tgttccctaa tgaccaggaa agtaatgaac aactgtgtgc ctacatattg    5700
ggtgagacca tggaagcaat ccgcgaaaag tgcccggtcg accataaccc gtcgtctagc    5760
ccgcccaaaa cgttgccgtg cctttgcatg tatgccatga cgccagaaag ggtccacaga    5820
cttagaagca ataacgtcaa agaagttaca gtatgctcct ccaccccct tcctaagcac    5880
aaaattaaga atgttcagaa ggttcagtgc acgaaagtag tcctgtttaa tccgcacact    5940
cccgcattcg ttcccgcccg taagtacata gaagtgccag aacagcctac cgctcctcct    6000
gcacaggccg aggaggcccc cgaagttgta gcgacaccgt caccatctac agctgataac    6060
acctcgcttg atgtcacaga catctcactg gatatggatg acagtagcga aggctcactt    6120
ttttcgagct ttagcggatc ggacaactct attactagta tggacagttg gtcgtcagga    6180
cctagttcac tagagatagt agaccgaagg caggtggtgg tggctgacgt tcatgccgtc    6240
caagagcctg cccctattcc accgccaagg ctaaagaaga tggcccgcct ggcagcggca    6300
agaaaagagc ccactccacc ggcaagcaat agctctgagt ccctccacct ctcttttggt    6360
ggggtatcca tgtcccctcg gatcaattttc gacggagaga cggcccgcca ggcagcggta    6420
caaccctggg caacaggccc cacggatgtg cctatgtctt tcggatcgtt ttccgacgga    6480
gagattgatg agctgagccg cagagtaact gagtccgaac ccgtcctgtt tggatcattt    6540
gaaccgggcg aagtgaactc aattatatcg tcccgatcag ccgtatcttt tccactacgc    6600
aagcagagac gtagacgcag gagcaggagg actgaatact gactaaccgg ggtaggtggg    6660
tacatatttt cgacggacac aggccctggg cacttgcaaa agaagtccgt tctgcagaac    6720
```

-continued

```
cagcttacag aaccgacctt ggagcgcaat gtcctggaaa gaattcatgc cccggtgctc    6780
gacacgtcga agaggaaca actcaaactc aggtaccaga tgatgcccac cgaagccaac    6840
aaaagtaggt accagtctcg taaagtagaa atcagaaag ccataaccac tgagcgacta    6900
ctgtcaggac tacgactgta taactctgcc acagatcagc cagaatgcta aagatcacc    6960 tatccgaaac cattgtactc cagtagcgta ccggcgaact actccgatcc acagttcgct    7020
gtagctgtct gtaacaacta tctgcatgag aactatccga cagtagcatc ttatcagatt    7080
actgacgagt acgatgctta cttggatatg gtagacgaga cagtcgcatg cctggatact    7140
gcaaccttct gccccgctaa gcttagaagt tacccgaaaa acatgagta tagagccccg    7200 aatatccgca gtgcggttcc atcagcgatg cagaacacgc tacaaaatgt gctcattgcc    7260
gcaactaaaa gaaattgcaa cgtcacgcag atgcgtgaac tgccaacact ggactcagcg    7320
acattcaatg tcgaatgctt tcgaaaatat gcatgtaatg acgagtattg ggaggagttc    7380
gctcggaagc caattaggat taccactgag tttgtcaccg catatgtagc tagactgaaa    7440
ggccctaagg ccgccgcact atttgcaaag acgtataatt tggtcccatt gcaagaagtg    7500
cctatggata gattcgtcat ggacatgaaa agagacgtga agttacacc aggcacgaaa    7560 cacacagaag aaagaccgaa agtacaagtg atacaagccg cagaacccct ggcgactgct    7620
tacttatgcg ggattcaccg ggaattagtg cgtaggctta cggccgtctt gcttccaaac    7680
attcacacgc tttttgacat gtcggcggag gattttgatg caatcatagc agaacacttc    7740
aagcaaggcg acccggtact ggagacggat atcgcatcat tcgacaaaag ccaagacgac    7800
gctatggcgt taaccggtct gatgatcttg gaggacctgg gtgtggatca accactactc    7860
gacttgatcg agtgcgcctt tggagaaata tcatccaccc atctacctac gggtactcgt    7920
tttaaattcg ggcgatgat gaaatccgga atgttcctca cacttttgt caacacagtt    7980 ttgaatgtcg ttatcgccag cagagtacta gaagagcggc ttaaaacgtc cagatgtgca    8040
gcgttcattg gcgacgacaa catcatacat ggagtagtat ctgacaaaga aatggctgag    8100
aggtgcgcca cctggctcaa catggaggtt aagatcatcg acgcagtcat cggtgagaga    8160
ccaccttact tctgcggcgg atttatcttg caagattcgg ttacttccac agcgtgccgc    8220
gtggcggatc ccctgaaaag gctgtttaag ttgggtaaac cgctcccagc cgacgacgag    8280
caagacgaag acagaagacg cgctctgcta gatgaaacaa aggcgtggtt tagagtaggt    8340
ataacaggca ctttagcagt ggccgtgacg acccggtatg aggtagacaa tattacacct    8400
gtcctactgg cattgagaac ttttgcccag agcaaaagag cattccaagc catcagaggg    8460
gaaataaagc atctctacgg tggtcctaaa tagtcagcat agtacatttc atctgactaa    8520
tactacaaca ccaccacctc tagacgcgta gatctcacgt gagcatgcag gccttgggcc    8580
caatgatccg accagcaaaa ctcgatgtac ttccgaggaa ctgatgtgca taatgcatca    8640
ggctggtaca ttagatcccc gcttaccgcg ggcaatatag caacactaaa aactcgatgt    8700
acttccgagg aagcgcagtg cataatgctg cgcagtgttg ccacataacc actatattaa    8760
ccatttatct agcggacgcc aaaaactcaa tgtatttctg aggaagcgtg gtgcataatg    8820
ccacgcagcg tctgcataac ttttattatt tcttttatta atcaacaaaa ttttgttttt    8880
aacatttcaa aaaaaaaaaa aaaaaaaaaa aaaaaaaaaa aaaaagggaa ttcccaactt    8940
gtttattgca gcttataatg gttacaaata aagcaatagc atcacaaatt tcacaaataa    9000
agcatttttt tcactgcatt ctagttgtgg tttgtccaaa ctcatcaatg tatcttatca    9060
```

-continued

```
tgtctggatc cgtcgagacg cgtccaattc gccctatagt gagtcgtatt acgcgcgctt      9120
ggcgtaatca tggtcatagc tgtttcctgt gtgaaattgt tatccgctca caattccaca      9180
caacatacga gccggaagca taaagtgtaa agcctgggt gcctaatgag tgagctaact      9240
cacattaatt gcgttgcgct cactgcccgc tttccagtcg ggaaacctgt cgtgccagct      9300
gcattaatga atcggccaac gcgcggggag aggcggtttg cgtattgggc gctcttccgc      9360
ttcctcgctc actgactcgc tgcgctcggt cgttcggctg cggcgagcgg tatcagctca      9420
ctcaaaggcg gtaatacggt tatccacaga atcaggggat aacgcaggaa agaacatgtg      9480
agcaaaaggc cagcaaaagg ccaggaaccg taaaaaggcc gcgttgctgg cgttttccca      9540
taggctccgc cccctgacg agcatcacaa aaatcgacgc tcaagtcaga ggtggcgaaa      9600
cccgacagga ctataaagat accaggcgtt tcccctgga agctcctcg tgcgctctcc       9660 tgttccgacc ctgccgctta ccggatacct gtccgccttt ctcccttcgg aagcgtggc       9720 gctttctcaa tgctcacgct gtaggtatct cagttcggtg taggtcgttc gctccaagct      9780
gggctgtgtg cacgaacccc ccgttcagcc cgaccgctgc gccttatccg gtaactatcg      9840
tcttgagtcc aacccggtaa gacacgactt atcgccactg gcagcagcca ctggtaacag      9900
gattagcaga gcgaggtatg taggcggtgc tacagagttc ttgaagtggt ggcctaacta      9960
cggctacact agaaggacag tatttggtat ctgcgctctg ctgaagccag ttaccttcgg     10020
aaaaagagtt ggtagctctt gatccggcaa acaaaccacc gctggtagcg gtggtttttt     10080
tgtttgcaag cagcagatta cgcgcagaaa aaaaggatct caagaagatc ctttgatctt     10140
ttctacgggg tctgacgctc agtggaacga aaactcacgt taagggattt tggtcatgag     10200
attatcaaaa aggatcttca cctagatcct tttaaattaa aatgaagttt taaatcaat      10260 ctaaagtata tatgagtaaa cttggtctga cagttaccaa tgcttaatca gtgaggcacc     10320
tatctcagcg atctgtctat ttcgttcatc catagttgcc tgactccccg tcgtgtagat     10380
aactacgata cgggagggct taccatctgg ccccagtgct gcaatgatac cgcgagaccc     10440
acgctcaccg gctccagatt tatcagcaat aaaccagcca gccggaaggg ccgagcgcag     10500
aagtggtcct gcaactttat ccgcctccat ccagtctatt aattgttgcc gggaagctag     10560
agtaagtagt tcgccagtta atagtttgcg caacgttgtt gccattgcta caggcatcgt     10620
ggtgtcacgc tcgtcgtttg gtatggcttc attcagctcc ggttcccaac gatcaaggcg     10680
agttacatga tcccccatgt tgtgcaaaaa agcggttagc tccttcggtc ctccgatcgt     10740
tgtcagaagt aagttggccg cagtgttatc actcatggtt atggcagcac tgcataattc     10800
tcttactgtc atgccatccg taagatgctt ttctgtgact ggtgagtact caaccaagtc     10860
attctgagaa tagtgtatgc ggcgaccgag ttgctcttgc ccggcgtcaa tacgggataa     10920
taccgcgcca catagcagaa ctttaaaagt gctcatcatt ggaaaacgtt cttcggggcg     10980
aaaactctca aggatcttac cgctgttgag atccagttcg atgtaaccca ctcgtgcacc     11040
caactgatct tcagcatctt ttactttcac cagcgtttct gggtgagcaa aaacaggaag     11100
gcaaaatgcc gcaaaaaagg gaataagggc gacacgaaaa tgttgaatac tcatactctt     11160
cctttttcaa tattattgaa gcatttatca gggttattgt ctcatgagcg gatacatatt     11220
tgaatgtatt tagaaaaata aacaaatagg ggttccgcgc acatttcccc gaaaagtgcc     11280
ac                                                                   11282
```

<210> SEQ ID NO 2
<211> LENGTH: 25

<212> TYPE: DNA
<213> ORGANISM: Artificial Sequence
<220> FEATURE:
<223> OTHER INFORMATION: Description of Artificial Sequence:primer

<400> SEQUENCE: 2
aacattgaaa tcgatattac agggg                                              25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 3
cgggttatgg tcgaccgggc                                                    20

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 4
gtgccctccc ctgagtttaa acaattcagg gccgaacgcg                              40

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 5
gaattgttta aactcaggag gcaccctcgt gg                                      32

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 6
ggtagacgag acagtcgcat gcctggatac                                         30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 7
gtatccaggc atgcgactgt ctcgtctacc                                         30

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 8

-continued

```
cagaccggtt aacgccatag cgtcg                                              25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 9
ctctattact agtatggaca gttgg                                              25
```